(12) United States Patent
Ettinger et al.

(10) Patent No.: US 8,247,228 B2
(45) Date of Patent: *Aug. 21, 2012

(54) METHOD OF INDUCING MEMORY B CELL DEVELOPMENT AND TERMINAL DIFFERENTIATION

(75) Inventors: Catherine Rachel Ettinger, Bethesda, MD (US); Peter E. Lipsky, Rockville, MD (US); Warren J. Leonard, Bethesda, MD (US); Rosanne Spolski, Ellicott City, MD (US); Herbert C. Morse, III, Rockville, MD (US)

(73) Assignee: The United States of America, as represented by the Secretary of the Department of Health and Human Services, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/126,166

(22) Filed: May 23, 2008

(65) Prior Publication Data

US 2008/0305076 A1     Dec. 11, 2008

Related U.S. Application Data

(60) Division of application No. 11/197,221, filed on Aug. 3, 2005, now Pat. No. 7,378,276, which is a continuation-in-part of application No. PCT/US2004/039135, filed on Nov. 18, 2004.

(60) Provisional application No. 60/523,754, filed on Nov. 19, 2003.

(51) Int. Cl.
  *C12N 5/00*     (2006.01)
  *C12N 5/07*     (2010.01)
(52) U.S. Cl. ......... 435/377; 435/372; 435/325; 530/351
(58) Field of Classification Search .................. None
  See application file for complete search history.

(56) References Cited

U.S. PATENT DOCUMENTS

| | | | |
|---|---|---|---|
| 6,307,024 B1 | 10/2001 | Novak et al. | |
| 6,576,744 B1 | 6/2003 | Presnell et al. | |
| 7,749,697 B2 * | 7/2010 | Oleksiewicz et al. | 435/6.11 |
| 7,993,919 B2 * | 8/2011 | Leonard et al. | 435/377 |
| 2002/0128446 A1 | 9/2002 | Novak et al. | |
| 2002/0137677 A1 | 9/2002 | Sprecher et al. | |
| 2003/0003545 A1 | 1/2003 | Ebner et al. | |
| 2003/0108549 A1 | 6/2003 | Carter et al. | |
| 2003/0125524 A1 | 7/2003 | Novak et al. | |
| 2003/0134390 A1 | 7/2003 | Presnell et al. | |
| 2003/0138433 A1 | 7/2003 | Newell et al. | |
| 2005/0193434 A1 | 9/2005 | Leonard et al. | |

FOREIGN PATENT DOCUMENTS

| | | |
|---|---|---|
| WO | WO 99/61617 A1 | 12/1999 |
| WO | WO 01/77171 A2 | 10/2001 |
| WO | WO 03/028630 A2 | 4/2003 |
| WO | WO 03/040313 A2 | 5/2003 |
| WO | WO 03/052083 A2 | 6/2003 |
| WO | WO 03/082212 A2 | 10/2003 |
| WO | WO 2004/003156 A2 | 1/2004 |
| WO | WO 2005/052139 A2 | 6/2005 |

OTHER PUBLICATIONS

Peter Parham, The Immune System. 2005, 2nd Ed. Chapter 4. The development of B lymphocytes, pp. 99-122.*
Pollack et al.,"Development and use of palivizumab (Synagis): a passive immunoprophylactic agent for RSV." *Journal of Infection and Chemotherapy*, 8, 201-206 (2002).
Arai et al., *Ann. Rev. Biochem.*, 59, 783-836 (1990).
Aringer et al., Abstract: *J. Immunol.*, 170(12), 6057-6064 (2003).
Arpin et al., *J. Exp. Med.*, 186(6), 931-940 (1997).
Asao et al., *J. Immunol.*, 167, 1-5 (2001).
Brandt et al., Abstract: *Blood*, 102(12), 4090-4098 (2003).
Breitbart et al., Abstract: *J. Gerontol A. Biol. Sci. Med. Sci.*, 57, B304-B311 (2002).
Brenne et al., *Blood*, 99 (10), 3756-3762 (2002).
Calame, *Nat. Immunol.*, 2(12), 1103-1108 (2001).
Department of Microbiology and Immunology, USUHS, School of Medicine, 113-122 (2002).
Driver et al., *J. Immunol.*, 167, 1393-1405 (2001).
Ellmeier et al., *J. Exp. Med.*, 192(11), 1611-1623 (2000).
Ettinger et al., *J. Immunol.*, 176, 7867-7879 (2005).
Gause et al., *Immunology Lectures*, Department of Microbiology and Immunology, USUHS, 87-91, 93-99 (2002).
Gilboa, *Semin Oncol.*, 23(1), 101-107 (1996).
Guo et al., *Proc. Natl. Acad. Sci, USA*, 101(25), 9205-9210 (Jun. 22, 2004), Epub Jun. 14, 2004.
Hao et al., *J. Exp. Med.*, 194(8), 1151-1163 (2001).
Jankowski, "603423: PR Domain-Containing Protein 1: PRDM1," *Online Mendelian Inheritance in Man* (1999).
Kasaian et al., *Immunity*, 16, 559-569 (2002).
Kerkaert, "LAZ3 (Lymphoma Associated Zinc finger on chromosome 3)," *Atlas of Genetics and Cytogenetics in Oncology and Haematology*, http://www.infobiogen.fr/services/chromcancer/Genes/BCL61D20.html, 1998.
Kimchi-Sarfaty et al., *Science* 315(5811), 525-528 (2007).
Kishimoto et al., *Cell*, 76, 253-262 (1994).
Kovanen et al., *Immunol. Rev.* 202, 67-83 (2004).
Lee et al., *Proc. Natl. Acad. Sci. USA*, 96(16), 9136-9141 (Aug. 3, 1999).
Leonard, *Nat. Rev. Immununol.*, 1, 200-208 (2001).
McHeyzer-Williams et al., *J. Exp Med.*, 191(7), 1149-1165 (2000).
McKusick, "109565: B-Cell Lymphoma 6; BCL6," *Online Mendelian Inheritance in Man* (1993).
Mehta et al., *J. Immunol.*, 170, 4111-4118 (2003).
Mehta et al., *Immunol. Rev.*, 202, 84-95 (2004).
Mims et al., *Medical Microbiology, Third Edition*, Elsevier Science, 172-177 (2004).
Moroz et al., *J. Immunol.*, 173(2), 900-909 (Jul. 15, 2004).
Nutt et al., *Critical Reviews in Immunology*, 24 (4), 239-250 (2004).
Ozaki et al., *Journal of Immunology*, 173 (9), 5361-5371 (2004).

(Continued)

*Primary Examiner* — Dong Jiang
(74) *Attorney, Agent, or Firm* — Leydig, Voit & Mayer

(57) ABSTRACT

The invention provides a method for promoting differentiation of a mature naïve B cell or a B cell progenitor into a memory B cell or a plasma cell. The method comprises (a) contacting a population of cells comprising a mature naïve B cell or a B cell progenitor with an agent that activates at least one of JAK1, JAK3, STAT3, STAT5A or STAT5B; wherein the population of cells optionally is contacted with an antigen, and (b) isolating the memory B cell or plasma cell.

8 Claims, 19 Drawing Sheets

OTHER PUBLICATIONS

Ozaki et al., *Proc. Natl. Acad. Sci., USA*, 97 (21), 11439-11444, 2000.
Ozaki et al., *Science*, 298, 1630-1634 (2002).
Parrish-Novak et al., *J. Leukoc. Biol.*, 72 (5), 856-863 (2002).
Parrish-Novak et al., *Nature*, 408 (6808), 57-63 (2000).
Paul et al., *Cell*, 76, 241-251, 1994.
Riddell et al., *Nat. Med.*, 2(2), 216-223 (Feb. 1996).
Suto et al., *Blood*, 100 (13), 4565-4573 (2002).
Suzuki et al., *Int. Immunol.*, 12(2), 12-132 (2000).
Swissprot:BCL6_HUMAN, Accession No. P41182, Feb. 1, 1995.
Tangye et al., Abstract: *J. Immunol.*, 170, 686-694 (2003).
Ukai et al., *Mol. Carcinog*, 37, 110-119 (2003).
Voet, *Biochemistry John Wiley and Sons*, 126-128 (1990).
Vogelsang et al., *Blood*, 84(7), 2061-2067 (Oct. 1, 1994).
Vosshenrich et al., *Curr. Biol.*, 11(1), R175-R177 (2001).
Warnatz et al., *Blood*, 99(5), 1544-1551 (2002).
Weller et al., *PNAS*, 98(3), 1166-1170 (2001).
Zhang et al., Abstract: *Biochem. Biophys. Res. Commun.* 300(2), 291-296 (2003).

\* cited by examiner

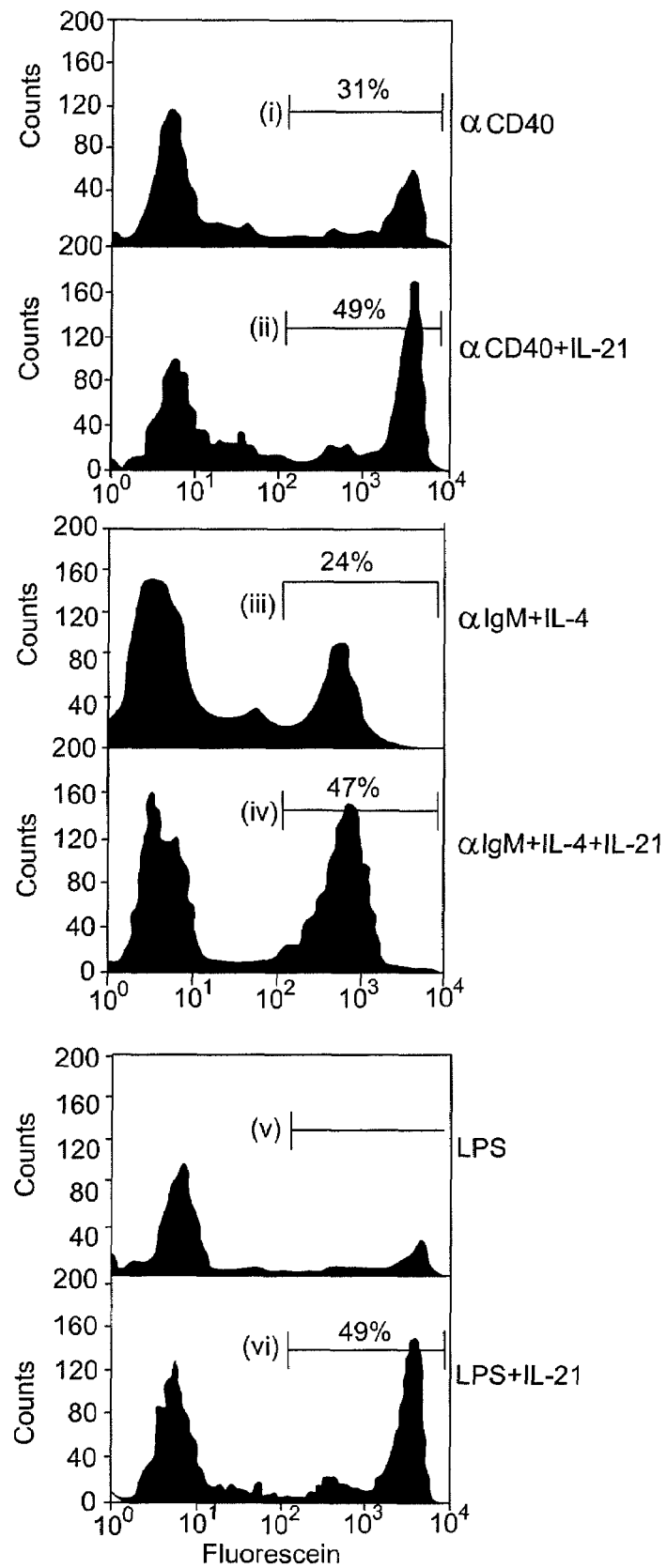

FIG. 1
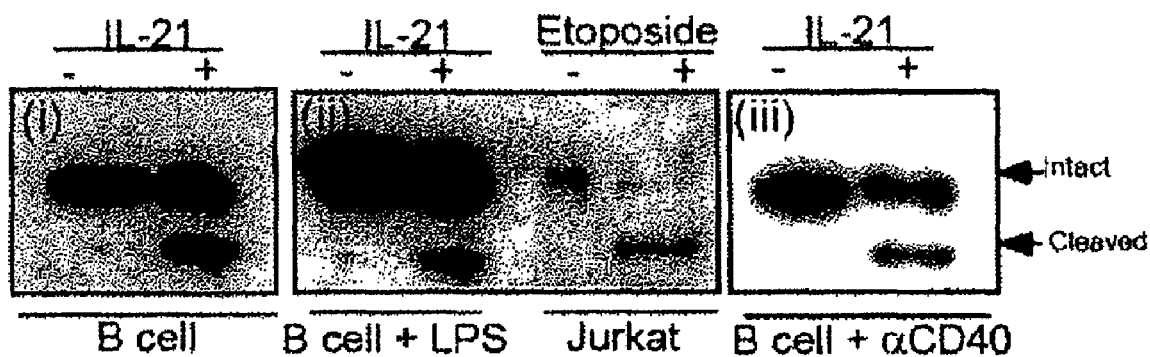
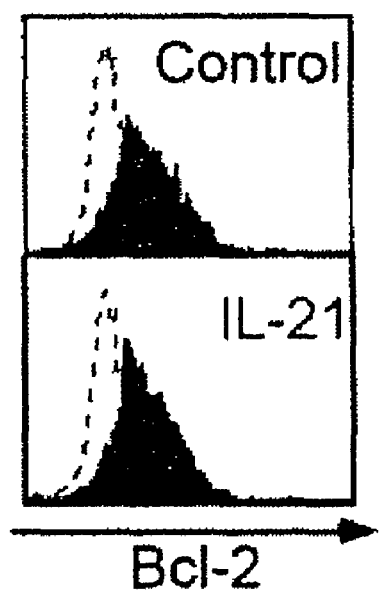
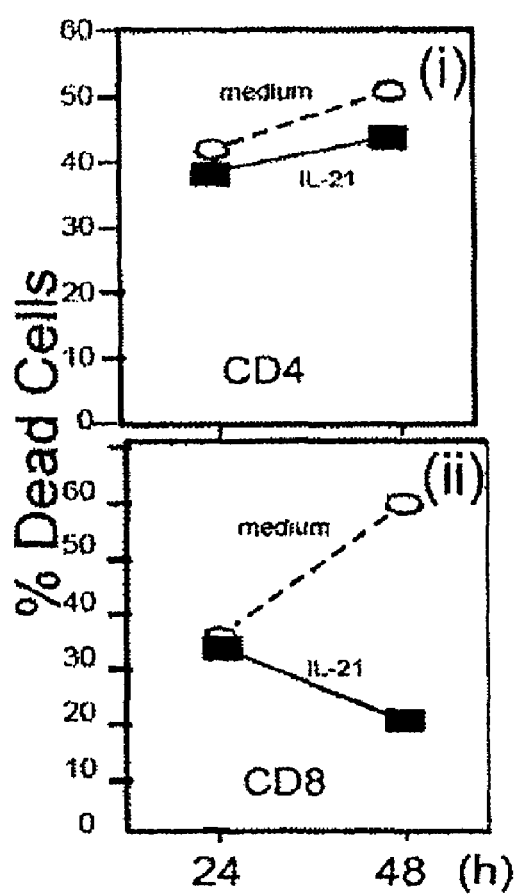

FIG. 6
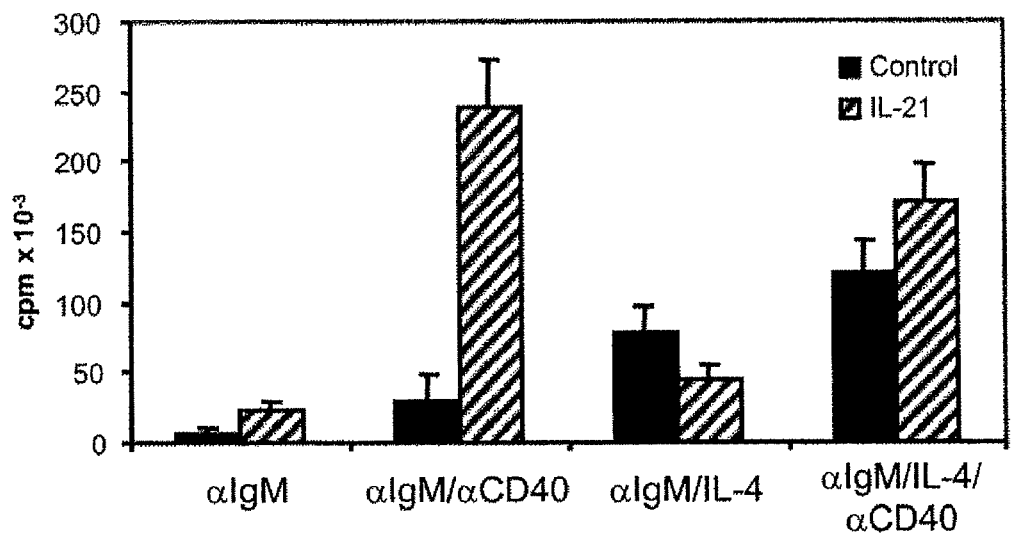
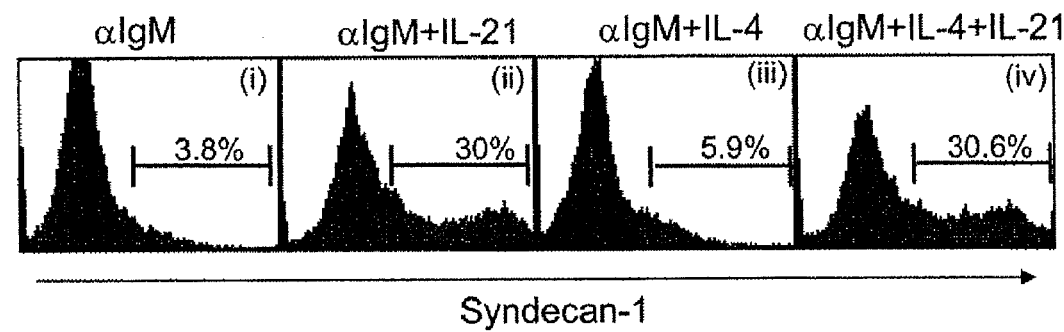
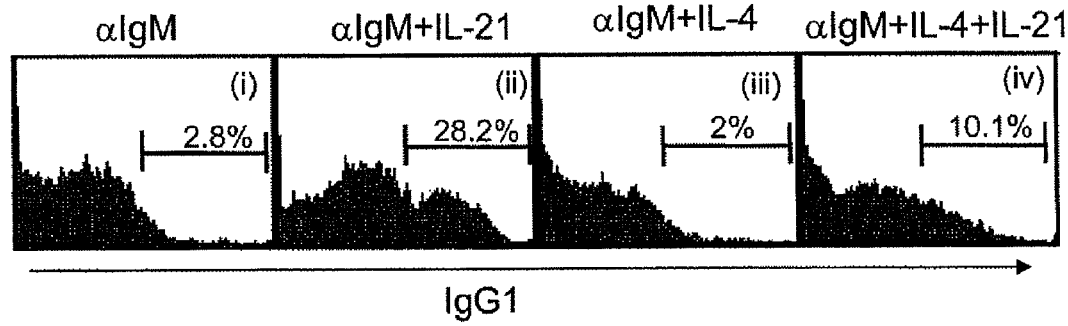

FIG. 10
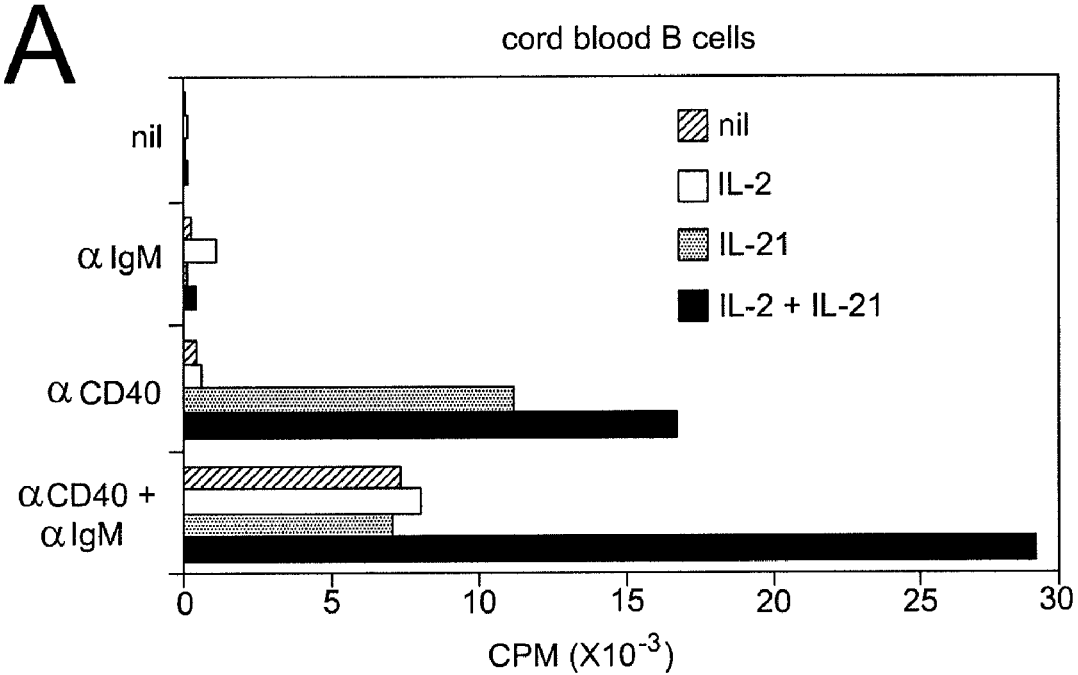
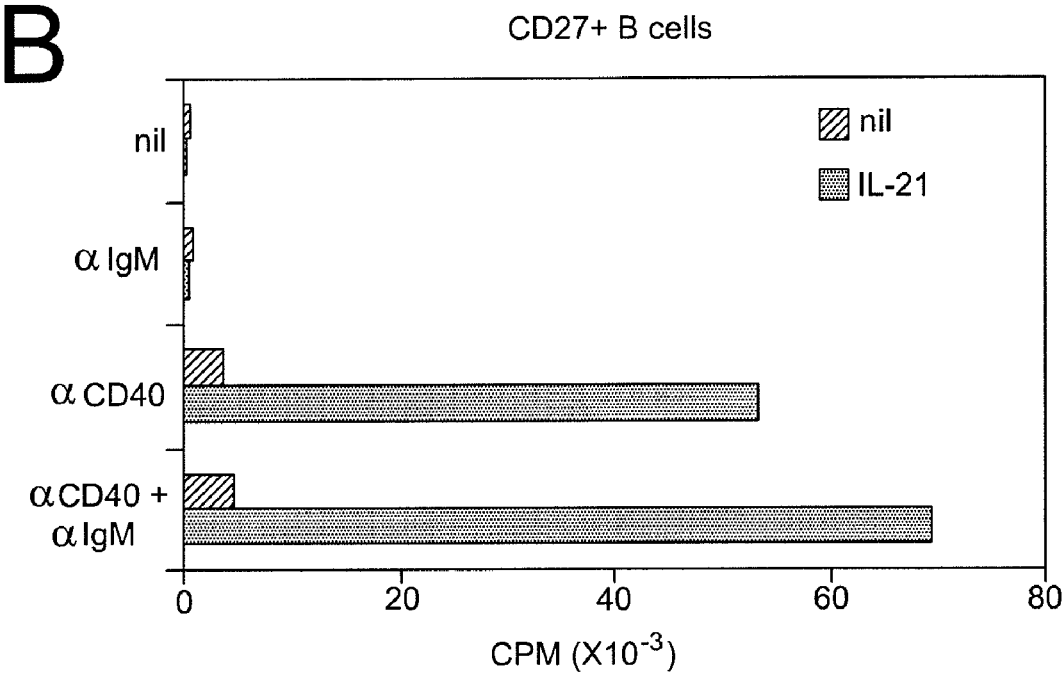

FIG. 13
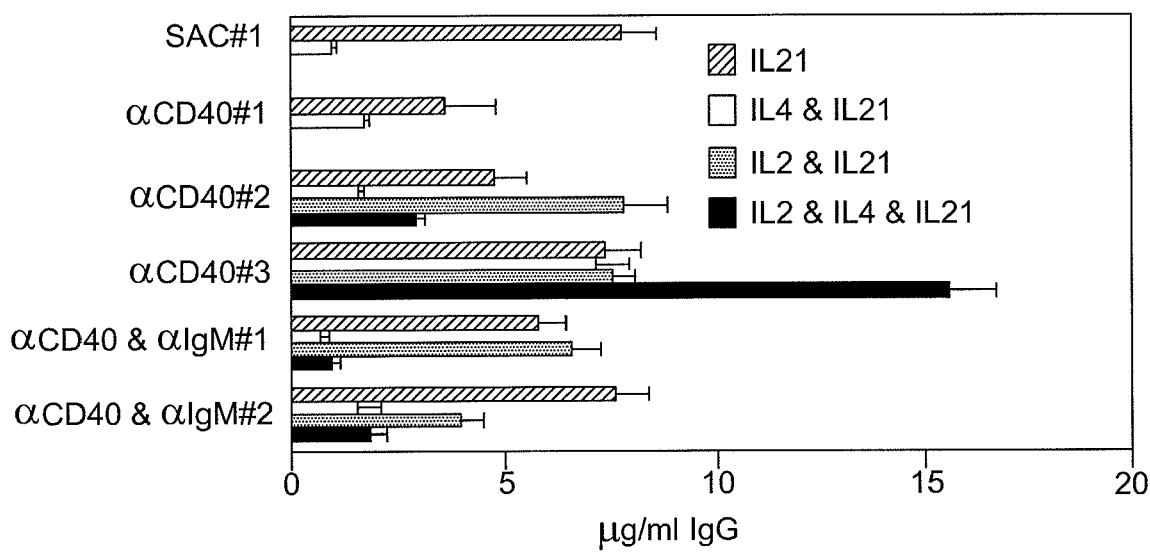
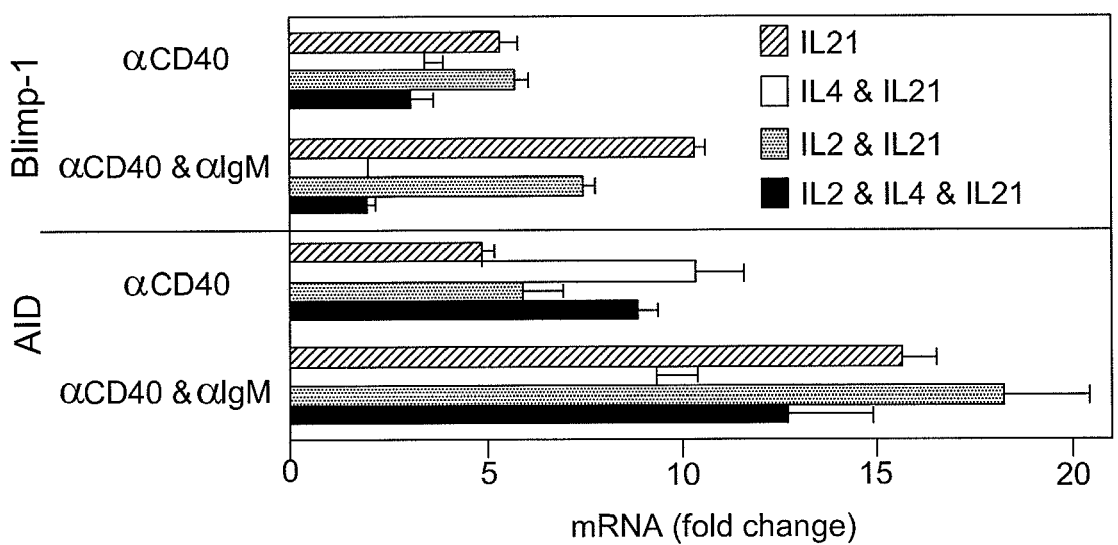

FIG. 14
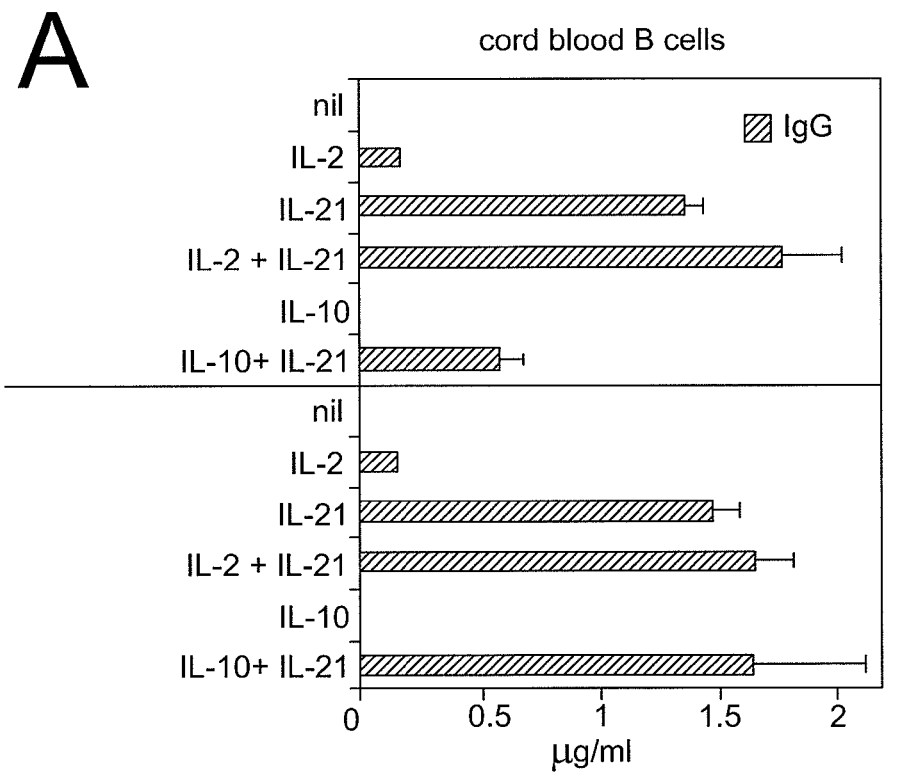
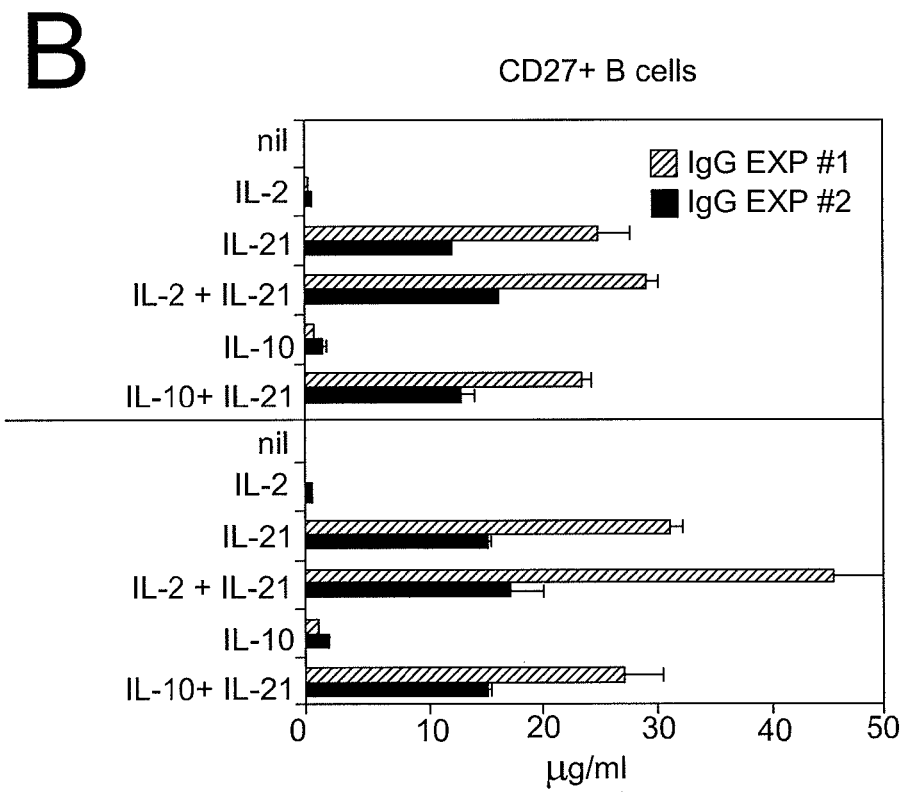

FIG. 18
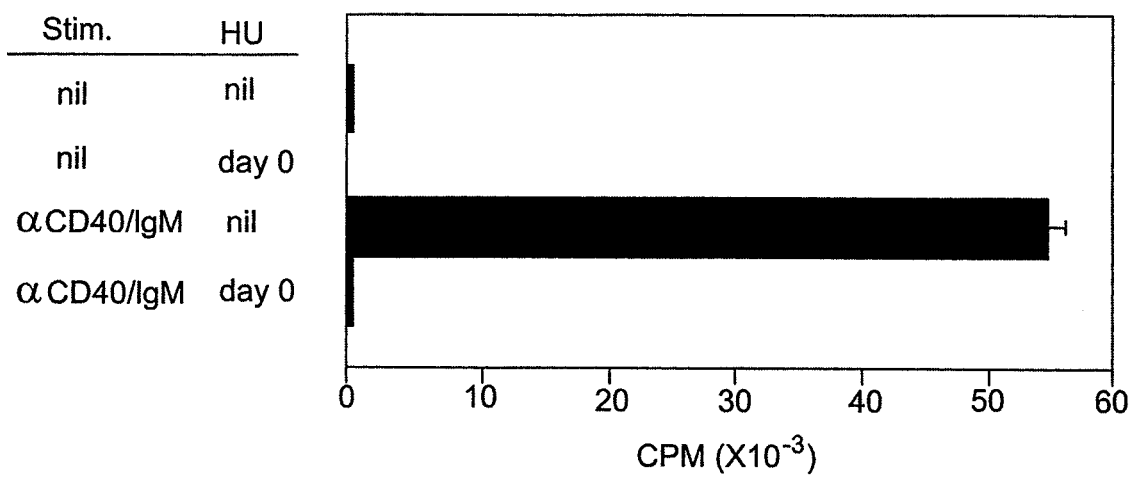
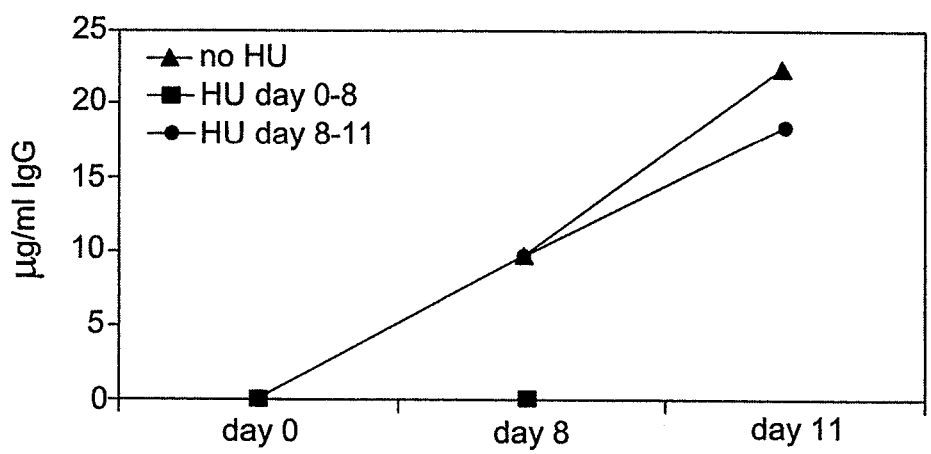

SEQUENCE LISTING

<160> NUMBER OF SEQ ID NOS: 17

<210> SEQ ID NO 1
<211> LENGTH: 160
<212> TYPE: PRT
<213> ORGANISM: Homo sapiens

<400> SEQUENCE: 1

Met Arg Ser Ser Pro Gly Asn Met Glu Arg Ile Val Ile Cys Leu Met
1               5                   10                  15

Val Ile Phe Leu Gly Thr Leu Val His Lys Ser Ser Gln Gly Gln
            20                  25                  30

Asp Arg His Met Ile Arg Met Arg Gln Leu Ile Asp Ile Val Asp Gln
            35                  40                  45

Leu Lys Asn Tyr Val Asn Asp Leu Val Pro Glu Phe Leu Pro Ala Pro
        50                  55                  60

Glu Asp Val Glu Thr Asn Cys Glu Trp Ser Ala Phe Ser Cys Phe Gln
65                  70                  75                  80

Lys Ala Gln Leu Lys Ser Ala Asn Thr Gly Asn Asn Glu Arg Ile Ile
                85                  90                  95

Asn Val Ser Ile Lys Lys Leu Lys Arg Lys Pro Pro Ser Thr Asn Ala
            100                 105                 110

Gly Arg Arg Gln Lys His Arg Leu Thr Cys Pro Ser Cys Asp Ser Tyr
        115                 120                 125

Glu Lys Lys Pro Pro Lys Glu Phe Leu Glu Arg Phe Lys Ser Leu Leu
130                 135                 140

Gln Lys Met Ile His Gln His Leu Ser Ser Arg Thr His Gly Ser Glu
145                 150                 155                 160

<210> SEQ ID NO 2
<211> LENGTH: 146
<212> TYPE: PRT
<213> ORGANISM: Mus musculus

<400> SEQUENCE: 2

Met Glu Arg Thr Leu Val Cys Leu Val Val Ile Phe Leu Gly Thr Val
1               5                   10                  15

Ala His Lys Ser Ser Pro Gln Gly Pro Asp Arg Leu Leu Ile Arg Leu
            20                  25                  30

Arg His Leu Ile Asp Ile Val Glu Gln Leu Lys Ile Tyr Glu Asn Asp
            35                  40                  45

Leu Asp Pro Glu Leu Leu Ser Ala Pro Gln Asp Val Lys Gly His Cys
        50                  55                  60

Glu His Ala Ala Phe Ala Cys Phe Gln Lys Ala Lys Leu Lys Pro Ser
65                  70                  75                  80

Asn Pro Gly Asn Asn Lys Thr Phe Ile Ile Asp Leu Val Ala Gln Leu
                85                  90                  95

Arg Arg Arg Leu Pro Ala Arg Arg Gly Gly Lys Lys Gln Lys His Ile
            100                 105                 110

Ala Lys Cys Pro Ser Cys Asp Ser Tyr Glu Lys Arg Thr Pro Lys Glu
        115                 120                 125

Phe Leu Glu Arg Leu Lys Trp Leu Leu Gln Lys Met Ile His Gln His
130                 135                 140

Leu Ser
145

```
<210> SEQ ID NO 3
<211> LENGTH: 30
<212> TYPE: DNA
<213> ORGANISM: Artificial
<220> FEATURE:
<223> OTHER INFORMATION: Oligonucleotide probe/primer

<400> SEQUENCE: 3
cagtccacag taaggaagtg aaattaattt                                        30

<210> SEQ ID NO 4
<211> LENGTH: 20
<212> TYPE: DNA
<213> ORGANISM: Artificial
<220> FEATURE:
<223> OTHER INFORMATION: Oligonucleotide probe/primer

<400> SEQUENCE: 4
gaaaattcct agaaagcata                                                   20

<210> SEQ ID NO 5
<211> LENGTH: 22
<212> TYPE: DNA
<213> ORGANISM: Artificial
<220> FEATURE:
<223> OTHER INFORMATION: Oligonucleotide probe/primer

<400> SEQUENCE: 5
acagaggccg agtttgaaga ga                                                22

<210> SEQ ID NO 6
<211> LENGTH: 19
<212> TYPE: DNA
<213> ORGANISM: Artificial
<220> FEATURE:
<223> OTHER INFORMATION: Oligonucleotide probe/primer

<400> SEQUENCE: 6
aaggatgcct cggcttgaa                                                    19

<210> SEQ ID NO 7
<211> LENGTH: 19
<212> TYPE: DNA
<213> ORGANISM: Artificial
<220> FEATURE:
<223> OTHER INFORMATION: Oligonucleotide probe/primer

<400> SEQUENCE: 7
ccctgggatt ccggcgctg                                                    19

<210> SEQ ID NO 8
<211> LENGTH: 21
<212> TYPE: DNA
<213> ORGANISM: Artificial
<220> FEATURE:
<223> OTHER INFORMATION: Oligonucleotide probe/primer

<400> SEQUENCE: 8
aaacgcaaga gggatgaagg t                                                 21

<210> SEQ ID NO 9
<211> LENGTH: 19
<212> TYPE: DNA
<213> ORGANISM: Artificial
<220> FEATURE:
<223> OTHER INFORMATION: Oligonucleotide probe/primer
```

-continued

```
<400> SEQUENCE: 9
aacaggtctc cccgcatct                                              19

<210> SEQ ID NO 10
<211> LENGTH: 21
<212> TYPE: DNA
<213> ORGANISM: Artificial
<220> FEATURE:
<223> OTHER INFORMATION: Oligonucleotide probe/primer

<400> SEQUENCE: 10
cacttccggg ccgggacttc c                                           21

<210> SEQ ID NO 11
<211> LENGTH: 26
<212> TYPE: DNA
<213> ORGANISM: Artificial
<220> FEATURE:
<223> OTHER INFORMATION: Oligonucleotide probe/primer

<400> SEQUENCE: 11
tcagagtatt cggattctag ctgtga                                      26

<210> SEQ ID NO 12
<211> LENGTH: 18
<212> TYPE: DNA
<213> ORGANISM: Artificial
<220> FEATURE:
<223> OTHER INFORMATION: Oligonucleotide probe/primer

<400> SEQUENCE: 12
tgcagcgtgt gcctcttg                                               18

<210> SEQ ID NO 13
<211> LENGTH: 27
<212> TYPE: DNA
<213> ORGANISM: Artificial
<220> FEATURE:
<223> OTHER INFORMATION: Oligonucleotide probe/primer

<400> SEQUENCE: 13
tgcaacgaat gtgactgccg tttctct                                     27

<210> SEQ ID NO 14
<211> LENGTH: 20
<212> TYPE: DNA
<213> ORGANISM: Artificial
<220> FEATURE:
<223> OTHER INFORMATION: Oligonucleotide probe/primer

<400> SEQUENCE: 14
ttcaccacca tggagaaggc                                             20

<210> SEQ ID NO 15
<211> LENGTH: 20
<212> TYPE: DNA
<213> ORGANISM: Artificial
<220> FEATURE:
<223> OTHER INFORMATION: Oligonucleotide probe/primer

<400> SEQUENCE: 15
ggcatggact gtggtcatga                                             20

<210> SEQ ID NO 16
<211> LENGTH: 26
<212> TYPE: DNA
```

```
<213> ORGANISM: Artificial
<220> FEATURE:
<223> OTHER INFORMATION: Oligonucleotide probe/primer

<400> SEQUENCE: 16
tgcatcctgc accaccaact gcttag                                          26

<210> SEQ ID NO 17
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (3)..(3)
<223> OTHER INFORMATION: X  is any amino acid

<400> SEQUENCE: 17

Trp Ser Xaa Trp Ser
1               5
```

METHOD OF INDUCING MEMORY B CELL DEVELOPMENT AND TERMINAL DIFFERENTIATION

CROSS REFERENCE TO RELATED APPLICATIONS

The present application a divisional of U.S. application Ser. No. 11/197,221, filed Aug. 3, 2005, which issued as U.S. Pat. No. 7,378,276, which is a Continuation-In-Part application and claims priority to and benefit of PCT Application No. PCT/US/2004/039135, filed Nov. 18, 2004, which claims priority to and benefit of U.S. Provisional Application No. 60/523,754, filed Nov. 19, 2003. The disclosures of these documents are incorporated herein by reference for all purposes.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 6,091 Byte ASCII (Text) file named "702810ST25.TXT," created on May 23, 2008.

FIELD

This application relates to the field of immunology, specifically to the use of IL-21 to induce differentiation of immature B cells into memory B cells and plasma cells.

BACKGROUND

Cytokines exert their respective biochemical and physiological effects by binding to specific receptor molecules. Receptor binding then stimulates specific signal transduction pathways (Kishimoto et al., *Cell* 76:253-262, 1994). The specific interactions of cytokines with their receptors can be the primary regulators of a wide variety of cellular processes including activation, proliferation, and differentiation of cells (Arai et al., *Ann. Rev. Biochem.* 59:783-836, 1990; Paul and Seder, *Cell* 76:241-251, 1994).

Interleukin-21 (IL-21) is a type I cytokine whose receptor is expressed on T, B, and NK cells. IL-21 was isolated from a cDNA library derived from activated CD3 (+) T cells (Parrish-Novak et al., *Nature* 408 57-63, 2000). The IL-21 cDNA encodes a secreted protein of 131 amino acids protein most closely related to IL-2 and IL-15. The IL-21 gene has been mapped to human chromosome 4q26-q27 near the IL-2 gene.

IL-21 mRNA is expressed in activated CD4+ but not in activated CD8+ T cells. In addition, IL-21 expression was not detected in B cells and monocytes (Parrish-Novak et al., *Nature* 408:57-63, 2000). IL-21 has also been shown to stimulate proliferation of naïve (CD45RA+) cells, but not memory (CD45RO+) T cells, mediated by engagement of CD3. IL-21 has also been shown to stimulate the proliferation of bone marrow progenitor to cells and to enhance the expression of the NK-cell marker CD56 in the presence of IL-15 (for review, see Horst Ibelgaufts' *COPE: Cytokines Online Pathfinder Encyclopedia*, available on the internet). In vitro, IL-21 can act as a co-mitogen for anti-CD3-induced thymocyte and peripheral T cell proliferation (Parrish-Novak et al., *Nature* 408:57-63, 2000), augment NK cell expansion and differentiation from human CD34+ cells when cultured with IL-15 and Flt-3 ligand, and can also activate NK-cytolytic activity (Parrish-Novak et al., *Nature* 408:57-63, 2000; Kasaian et al., *Immunity* 16:559, 2002).

The IL-21 receptor has been isolated and was found to be expressed by CD23+ B cells, B cell lines, a T cell leukemia line, and NK cell lines. The receptor gene has been mapped to human chromosome 16p12 (see Parrish-Novak et al., *Nature* 408:57-63, 2000; Ozaki et al., *Proc. Natl. Acad. Sci. USA* 97:11439-11444, 2000). The receptor (538 amino acids) is most closely related to human IL-2 receptor beta chain, and contains a WSXWS (SEQ ID NO: 17) motif in the extracellular region, typical of type-1 cytokine receptors (see Ozaki et al., *Proc. Natl. Acad. Sci. USA* 97:11439-11444, 2000; Parrish-Novak et al., *Nature* 408:57-63, 2000; and *Nat. Rev. Immunol.* 1:200-208). The common cytokine receptor gamma chain, an indispensable subunit of the functional receptor complexes for IL-2, IL-4, IL-7, IL-9, and IL-15 has been shown also to be part of the IL-21 receptor complex. The functional signaling complex signals in part through the activation of Jak1 and Jak3 as well as Stat1, Stat3, and Stat5 (see Asao et al., *J. Immunol.* 167:1-5, 2000; Ozaki et al., *Proc. Natl. Acad. Sci. USA* 97:11439-11444, 2000). However, the specific effects of IL-21 on the differentiation and populations of B cells and the activity of specific B cell populations have not previously been elucidated.

SUMMARY

A method is disclosed herein for inducing differentiation of mature B cells and B cell progenitors into memory B cells and/or plasma cells. The method involves contacting a population of cells including mature memory cells, naïve B cells and/or B cell progenitors with IL-21 and any appropriate costimulation agent, and isolating memory B cells and/or plasma cells. In one embodiment, the B cell progenitor is an immature B cell.

A method is also disclosed for enhancing an immune response. The method includes contacting a population of cells including mature memory cells, naïve B cells and/or B cell progenitors with IL-21 in the presence of any appropriate costimulation, and isolating memory B cells and/or plasma cells. The memory B cells and/or the plasma cell are then introduced into a subject to enhance the immune response.

In an embodiment, the method includes isolating a population of cells comprising mature memory cells, naïve B cells and/or B cell progenitors from a subject; contacting the population of cells with a composition comprising IL-21 or an agonist thereof (and any appropriate costimulation agent) ex vivo, thereby inducing differentiation of memory B cells and/ or plasma cells. The memory B cells, the plasma cells, or both are then isolated and introduced into a subject.

A method is also disclosed for treating a subject with a condition comprising an immunodeficiency characterized by a specific deficiency of memory B cells and/or plasma cells. The method includes administering IL-21 or an agonist thereof to the subject with such a deficiency, thereby ameliorating a sign or symptom of the deficiency.

A method is disclosed for identifying an agent with an effect on the differentiation of memory B cells and/or plasma cells. The method includes: contacting a population of B cell progenitors with an effective amount of IL-21 and an agent of interest; and detecting an effect of the agent on memory B cell differentiation, plasma cell differentiation, or both.

The foregoing and other features and advantages will become more apparent from the following detailed description of several embodiments, which proceeds with reference to the accompanying figures.

BRIEF DESCRIPTION OF THE FIGURES

FIGS. 1A-D are sets of digital images and graphs demonstrating that IL-21 is pro-apoptotic for B cells, but is anti-apoptotic for T cells, particularly CD8$^+$ T cells. FIG. 1A is a scatter plot of a FACS analysis showing that IL-21 augments DNA fragmentation (measured by TUNEL staining, Roche Applied Science, IN) in B cells stimulated with anti-CD40, anti-IgM+IL-4, or LPS. Upper, middle, and lower panels correspond to cells treated with anti-CD40±IL-21 for 15 hours, anti-IgM+IL-4±IL-21 for 48 hours, and LPS±IL-21 for 15 hours, respectively. FIG. 1B is a set of digital images showing caspase activation by IL-21 as indicated by PARP cleavage. Purified B cells were activated with LPS or anti-CD40±IL-21, for 6 hours or left untreated as controls. Clarified cell lysates (50 µg) were run on SDS gels and Western blotted with an anti-PARP Ab (Cell Signaling Technology, MA). The uncleaved and cleaved forms of PARP are also shown in Jurkat T cells treated with etoposide as a positive control. FIG. 1C is a set of scatter plots of FACS data demonstrating Bcl-2 levels were equivalent in untreated and IL-21-treated B cells. FIG. 1D is a set of graphs showing IL-21 preferentially increases survival of CD8$^+$ T cells.

FIG. 2A is a digital image of a Northern blot showing expression of IL-21 mRNA in IL-21 TG mice. Total RNA (10 µg) from bone marrow or spleen from WT or IL-21 TG mice was Northern blotted with human IL-21 cDNA (upper panel) or control pHe7 (lower panel) probes. TG line #8 showed approximately 30 fold higher IL-21 mRNA expression than the other two lines. FIG. 2B is a FACS plot demonstrating the lower apparent numbers of mature (M), follicular (FO), and marginal zone (MZ) B cells in IL-21 TG than in WT mice based on CD21/CD23 and 35 IgM/CD21 splenic expression patterns. T1, transitional B cells-1; T2, transitional B cells-2; NF, newly formed B cells. FIG. 2C is a FACS plot similar to the one shown in FIG. 2B except that cells were from IL-21 vector or saline injected B6 WT mice. Mice were analyzed at day 7.

FIG. 3A is a scatter plot obtained from a flow cytometric analysis of B cell populations. AA4.1/B220 staining of splenocytes from WT or TG mice (i and ii). CD23 profiles are shown for AA4.1$^{high}$ (iii and iv) and AA4.1$^{low}$ splenocytes (v and vi). IgM/IgD profiles are shown for AA4.1$^{high}$ (vii and viii) and AA4.1$^{low}$ (ix and x) splenocytes. FIG. 3B is a plot showing that L-21 potently decreases CD23 expression, whereas it is induced by IL-4. Shown are purified splenic B cells stimulated with LPS or anti-CD40 that were additionally treated with medium, IL-4, or IL-21 for 10 hours. The numbers are the mean fluorescent intensities of viable cells. FIG. 3C is a set of bar graphs showing the cellularity in mice following murine IL-21 injection. Shown are total cell numbers±S.D. (from more than 10 animals) for splenocytes as well as B cells (defined by B220) that were AA4.1$^{high}$ (immature B cells) and AA4.1$^{low}$ (resting mature B cells and post-switch cells).

FIG. 5A is a scatter plot showing annexin V staining of B220+ mature splenic B cells from TG line #5 mice (panel i) or IL-21 vector injected mice (panel ii). FIG. 5B is a set of plots showing reversed CD4:CD8 ratio in IL-21 TG mice (panel ii versus i) and IL-21 vector-injected mice (iv versus iii). FIG. 5C is a set of bar graphs showing that serum IgG (left) and IgM (right) levels (mean±SD) in WT and two IL-21 TG lines; 4 mice were analyzed in each group. FIG. 5D is a scatter plot showing increased surface IgG1$^+$ B cells in IL-21 TG mice. Splenocytes from IL-21 TG mice (line #5) and WT littermates were stained with anti-IgG1 and analyzed by flow cytometry. FIG. 5E is a bar graph showing ovalbumin specific Ig in WT versus IL-21 TG mice (line #5) immunized with 100 µg of ovalbumin/alum. Data are mean±S.D. Three mice were analyzed in each group and a representative mean±S.D. of 3 experiments is shown.

FIGS. 6A-C are graph and showing the effects of IL-21 on anti-IgM induced B cell proliferation, death, and differentiation. FIG. 6A is a bar graph showing that IL-21 potently increased proliferation of B cells stimulated with anti-IgM+ anti-CD40. Purified B cells from B6 WT mice were cultured with anti-IgM in the presence or absence of IL-21, IL-4, and anti-CD40 for 48 hours and were then pulsed with $^3$H-thymidine for the last 10 hours. Results depict the average proliferative response of 3 mice analyzed in a representative experiment. FIGS. 6B and 6C are plots obtained from a flow cytometric analysis of B cells cultured for 48 hours as above and analyzed for expression of syndecan-1 (FIG. 6B) and surface IgG1 (FIG. 6C). Data are representative of 3 similar experiments.

FIG. 7A is a set of plots showing that IL-21 induces syndecan-1 expression (left panel), but diminishes MHC II and CD23 expression (middle and right panels, respectively) in Bcl-1 cells. FIG. 7B is a set of bar graphs showing that IL-21 induces Blimp-1 (left panel) and Bcl-6 (middle panel) expression but decreases expression of Pax5 (right panel) mRNA, as evaluated by real-time PCR in Bcl-1 cells. The effect of the combination of IL-2 and IL-5 on expression of each gene is also shown. FIG. 7C is a digital image showing Induction of Blimp-1 protein, as evaluated by Western blotting in purified splenic B cells treated with the combination of anti-IgM plus IL-21 but not with anti-IgM alone. FIG. 7D is a digital image showing IL-21-mediated induction of Blimp-1 and Bcl-6 DNA binding activities as evaluated by EMSAs. Splenic B cells were isolated treated with anti-IgM with or without IL-21 as described in the Experimental Procedures, and then Blimp-1 and Bcl-6 DNA binding activities were evaluated using specific DNA probes. An antibody to Bcl-6 supershifted the Bcl-6 band, whereas an antibody to Stat3, which can bind the same probe (Reljic et al., *J. Exp. Med.* 192:1841-1847, 2000), did not supershift the Bcl-6 band.

FIGS. 10A and B are bar graphs, demonstrating that IL-21 induces class switch recombination and plasma cell differentiation from both naïve and memory B cells. B cells were positively-selected from cord blood, or negatively-selected from peripheral blood and further purified into CD20⁺ CD27⁺ memory B cells by cell sorting. All cells were cultured with anti-IgM, anti-CD40, both stimuli, or neither in the presence or absence of IL-2 and/or IL-21. B cell populations were stimulated as indicated and proliferative responses were measured by ³[H]-thymidine incorporation after 3 days in culture of either (FIG. 10A) CD27⁻ naïve or (FIG. 10B) CD27⁺ memory B cells. The purity of the cord blood and CD20⁺ CD27⁺ memory B cells at day 0 was measured. Neither cord blood B cells nor CD20⁺ CD27⁺ memory cells contained identifiable plasma cells before culture. After 6 days of culture, the cells were stained and analyzed for IgD and CD38 expression by CD19⁺ cells. No difference was observed in proliferation or change in phenotype of cord blood B cells isolated by negative vs. positive selection. Data are representative of results from one of six experiments for purified CD27⁻ cord blood B cells and one of five similar experiments for CD27+ sorted peripheral blood B cells.

In FIGS. 11A and B, IgM levels were not measured in any cultures containing anti-IgM. Data are mean concentration (±SD) from one of seven and six representative experiments, for (FIGS. 11A and B) respectively, and one representative experiment of four cord blood and three with CD27− and CD27+ adult peripheral B cells (FIG. 11C).

FIGS. 13A-B are bar graphs, showing that IL-4 inhibits IL-21-induced plasma cell differentiation. Purified peripheral B cells were isolated and cultured with the stimuli and cytokines indicated. Before culture the B cells contained 78% naïve B cells, 20% IgD⁻ B cells and 0.4% plasma cells. Cell surface expression of IgD and CD38 by CD19⁺ B cells following 6-7 days of culture was determined. IgG was quantified from culture supernatants following 7-11 days of incubation and data are shown as a mean concentration (±SEM) (FIG. 13A). mRNA was isolated and Blimp-1 and AID expression was determined following 3 days of culture (FIG. 13B). All data in (FIG. 13B) were normalized to β-2M mRNA and shown as fold change compared to cultures incubated with only IL-2 and IL-4. Data are shown as a mean fold change (±SEM). Data are representative of results from cultures of two similar experiments with SAC, three with αIgM, five with αCD40, seven with αIgM & αCD40, (FIG. 13A) two with SAC, and eight with αIgM and αCD40. For anti-CD40 stimulation, three of six experiments are shown in which four resulted in IL-4-induced suppression of IgG production and two did not which was not time dependent (FIG. 13A). The data in FIG. 13B are representative of four similar experiments.

FIGS. 14A and B are bar graphs, showing that IL-10 does not synergize with IL-21 in the differentiation of plasma cells and IgG production. Purified naïve cord blood B cells or CD27⁺ memory peripheral blood B cells were cultured with the stimuli and cytokines indicated for 6 days for cord blood B cells and 7 days for CD27⁺ peripheral blood B cells. At the end of the incubation period, cells were stained and analyzed for IgD and CD38 expression by CD19⁺ cells. Data are representative of results from one of three similar experiments. Cell supernatants were removed at end of culture and total IgG determined by ELISA (FIG. 14A). Data are shown as a mean concentration (±SD). Neither cord blood nor CD20⁺ CD27⁺ memory B cells contained plasma cells before culture.

FIGS. 18A and B are a bar graph and line graph, respectively illustrating that Ig production from IL-21-induced plasma cells is resistant to hydroxyurea. Purified peripheral blood B cells were isolated and (A) cultured in the presence of IL-21 with or without anti-CD40 and anti-IgM and with or without hydroxyurea (HU, 1×10$^{-2}$M) as indicated. Following 3 days of culture, proliferation was determined by incubating the cells for 16 hrs with $^3$[H]-thymidine. Purified peripheral blood B cells were isolated and cultured with or without IL-21 in the presence of anti-CD40 and anti-IgM and hydroxyurea was added (or not) on the days indicated. The cultures were analyzed for IgD and CD38 expression by CD19+B cells after 8 or 11 days in culture as indicated. (B) Supernatants from IL-21, anti-IgM and anti-CD40-stimulated cultures in were analyzed for IgG content. HU was added where indicated. Data are representative of results from multiple experiments.

SEQUENCE LISTING

Figure 2:
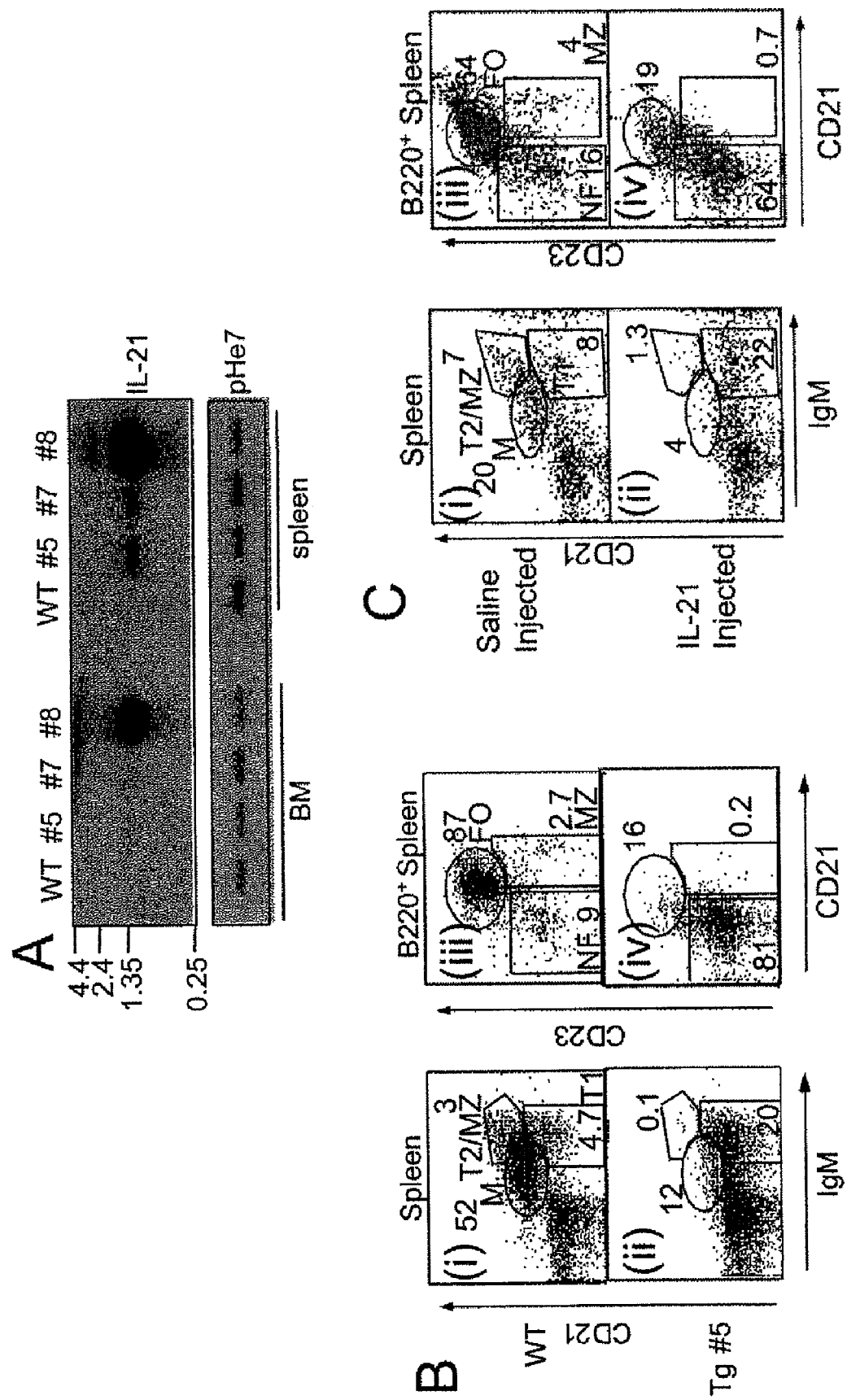
FIGS. 2A-C are sets of digital images and scatter plots showing the effect of IL-21 on B cell populations.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NO: 1 is the amino acid sequence of human IL-21.
SEQ ID NO: 2 is the amino acid sequence of murine IL-21.
SEQ ID NOs: 4-16 are the nucleic acid sequences of oligonucleotides used in the experimental studies described in the Examples.

DETAILED DESCRIPTION

Within the B cell lineage, IL-21 is important for IgG 1 production and cooperates with IL-4 for the production of other antibody classes in vivo (Ozaki et al., *Science* 298: 1630-1634, 2002; Suto et al., *Blood* 100:4565-4573).

IL-21R$^{-/-}$ mice have markedly diminished IgG1 but greatly elevated IgE levels in response to antigen, and IL-21R$^{-/-}$IL-4$^{-/-}$ double knockout mice have a severely impaired IgG and IgE response. In vitro, IL-21 can enhance the proliferative response of human and murine B cells stimulated with antibodies to CD40, but it inhibits B cell proliferation in response to anti-IgM+IL-4 or LPS (Parrish-Novak et al., *Nature* 408: 57-63, 2000), and correspondingly can augment B cell death (Mehta et al. *J. Immunol.* 170:4111, 2003; see also U.S. Provisional Patent Application No. 60/393,215; U.S. Provisional Patent Application No. 60/449,056; PCT Application No. PCT/US 03/20370, all of which are incorporated by reference in their entirety).

As disclosed herein, whereas IL-21 induces death of resting mature B cells, it promotes the differentiation of B cells activated in a T cell dependent manner into memory and plasma cells. IL-21 exerts these differential effects on B cell fate depending on the signaling context. Thus, IL-21 serves as a master regulator of B cell maturation and terminal differentiation into memory B cells and plasma cells.

IL-21 has been identified in a number of species, and any of these can be employed in the methods described herein. Preferably, an IL-21 is selected that binds to an IL-21 receptor expressed on the target B cell progenitor or mature B cell. Similarly, IL-21 polypeptide variants, especially conservative variants having only a small number of, such as 1 or 2 or 3, amino acid substitutions, relative to a naturally occurring IL-21 can be employed in the methods described herein. Additionally, IL-21 analogs, regardless of their amino acid composition, including subsequences and fragments of IL-21 are favorably employed in the methods described herein, provided that the IL-21 analog retains at least partial functional activity of an IL-21. That is, analogs that are IL-21 agonists, which bind to the IL-21 receptor and produce a physiological effect produced by binding of a native IL-21 to its cognate receptor, can be utilized in the same manner as an IL-21 polypeptide in the methods described herein.

The present disclosure provides methods for inducing differentiation of memory B cells and plasma cells from B cell progenitors and mature B cells, in quantities suitable for isolation of memory B cells and plasma cells. A population of cells including B cell progenitors and/or mature, antigen specific IgD expressing, B cells are contacted with a composition including IL-21. Following exposure to an effective amount of IL-21, B cell progenitors and mature B cells preferentially differentiate into memory B cells and plasma cells. The resulting enrichment for memory B cells and plasma cells permits isolation these B cell classes with increased efficiency.

For example, a population of bone marrow derived cells or peripheral blood cells including a wide variety of cell types including B cell progenitors and mature B cells can be exposed to an IL-21 containing composition, thereby inducing differentiation of B cell progenitors and mature B cells into memory B cells and/or plasma cells. Optionally, B cell progenitors and/or mature B cells can be isolated prior to treating them with IL-21. The methods described herein are applicable to B cells derived from a variety of species, particularly mammals, including humans.

Also described are methods for inducing differentiation of B cell progenitors into memory B cells and plasma cells by contacting a population of progenitor cells with an agent that activates at least one member of the JAK/STAT signaling pathway, for example JAK1, JAK3, STAT5A and/or STAT5B. Activation of this signaling pathway induces differentiation of memory B cells and plasma cell, which can be isolated from the population of treated cells. IL-21 is an exemplary agent that activates the JAK/STAT signaling pathway, thereby inducing differentiation of B cells into memory B cells and plasma cells.

As disclosed herein, IL-21 preferentially promotes differentiation of B cells into mature subsets with desirable functional attributes. Thus, IL-21 is of use to enhance an immune response in a subject, including a human subject. Although these methods have widespread applicability to enhance the efficacy of an immune response in a subject, these methods can also be employed more particularly to ameliorate immunodeficiencies, especially a deficiency characterized by reduction in number or function of memory B cells and/or plasma cells. For example, the methods described herein for enhancing an immune response can be used to treat a subject with a post-transplantation B cell deficiency.

An immune response in a subject can be enhanced by contacting a population of cells including mature B cells and/or B cell progenitors with a composition containing IL-21 to induce differentiation of the mature B cells or B cell progenitors into memory B cells and/or plasma cells. The differentiated mature B cells and plasma cells are then isolated and introduced into a subject to enhance an immune response.

For example, the cells can be contacted with IL-21 by administering a composition containing IL-21 directly to the subject, such as a human subject. In this case, the IL-21 is administered in a pharmaceutically acceptable formulation, such as a formulation containing IL-21 and a pharmaceutically acceptable carrier or excipient. Alternatively, the cells can be contacted with IL-21 ex vivo.

In some cases, the population of cells including mature B cells and/or B cell progenitors, such as immature B cells, is isolated. For example, mature B cells and/or B cell progenitors can be isolated from peripheral blood or bone marrow.

Optionally, the cells can also be contacted with an antigen, such as an antigen derived from a pathogen (e.g., a bacterial antigen, a viral antigen, or an antigen from a parasite).

Thus, the present disclosure provides methods for treating a subject with a condition characterized by a specific deficiency of memory B cells and/or plasma cells by administering to the subject a therapeutically effective amount of IL-21 or an agonist thereof, thereby ameliorating a sign or symptom of the deficiency. For example, the methods described herein can be used to ameliorate the symptoms of an immunodeficiency, such as an acquired immunodeficiency, e.g., a post bone marrow transplantation deficiency. Such an immunodeficiency can be characterized by a reduction in the number and/or function of memory B cells and plasma cells. Administering a therapeutically effective amount of IL-21 increases the number and/or the proportion of at least one of memory B cells and plasma cells.

In an embodiment, the IL-21 is administered by treating a population of cells including one or more of mature B cells and B cell progenitors ex vivo. Optionally, the memory B cells and/or plasma cells induced to differentiate ex vivo are isolated and introduced into the subject. The treated population of cells can be returned to the same subject, or can be introduced into a different subject, that is, the cells can be introduced as an autologous transfer or as a heterologous transfer.

Based on the identification of IL-21 as an agent that preferentially induces differentiation of memory B cells and plasma cells, methods have been developed for identifying agents that exert a physiological effect on the differentiation of these mature B cell subsets from B cell progenitors. Accordingly, methods for identifying agents with a physiological effect on the differentiation of memory B cells and plasma cells are described herein. Such methods involve contacting an isolated population of cells (including B cell progenitors, such as immature B cells) that has been exposed to IL-21 with an agent, and detecting a physiological effect of the agent on memory B cell differentiation, plasma cell differentiation, or both. For example, the effect detected can be inhibition of differentiation of one or more of memory B cells and plasma cells. Typically, screening methods for identifying agents with a physiological effect on differentiation of memory B cells and plasma cells involve contacting each of a plurality of populations of cells (or subsets of a population of cells) with a different agent. The different agents are usually members of a library of compositions.

Also disclosed are methods for identifying an agent that inhibits an activity of IL-21. The methods involve contacting a cell with at least one agent and detecting a decrease in the production or activity of at least one of Blimp-1, AID and Bcl-6 relative to a control cell. Optionally, the cell is contacted with IL-21. In one example, the method is utilized to identify antibodies that specifically bind to Blimp-1, AID or Bcl-6. Commonly, the control cell is a cell that is not contacted with the agent.

These and other features of the disclosure will be apparent upon review of the following detailed description and examples.

I. Abbreviations $\beta$-2M: $\beta$-2 microglobulin
$\gamma_C$: common cytokine receptor gamma ($\gamma$) chain
Ab: antibody
AID: activation induced cytidine deaminase
Bcl-6: B cell lymphoma 6
BCR: B-cell receptor
Blimp-1: B-lymphocyte induced maturation protein 1
CD40L: CD40 ligand
CSR: class switch recombination
FACS: fluorescence activated cell sorting or scanning
Hr: hour
IL-4: interleukin-4
IL-21: interleukin-21
IL-21R: interleukin 21 receptor
Ig: immunoglobulin
JAK: Janus Activated Kinase
LPS: lippopolysaccharide
FO: lymphoid follicles
FZ: follicular zone
MZ: marginal zone
M: mature
NF: newly formed
PARP: poly(ADP ribose) polymerase
SAC: *Staphylococcus aureus* Cowan I
SCID: severe combined immunodeficiency disease
S.D.: standard deviation
SH2: SRC homology-2
SMH: somatic hypermutation
STAT: Signal Transducer and Activator of Transcription
TG: transgenic
TUNEL: TdT-dependent dUTP-biotin nick end labeling
µg: microgram
WT: wild-type II. Terms Unless otherwise explained, all technical and scientific terms used herein have the same meaning as commonly understood by one of ordinary skill in the art to which this disclosure belongs. For example, definitions of common terms in molecular biology can be found in Benjamin Lewin, *Genes V*, published by Oxford University Press, 1994 (ISBN 0-19-854287-9); Kendrew et al. (eds.), *The Encyclopedia of*

*Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." For example, "comprising A or B" means including A or B, or both A and B, unless clearly indicated otherwise. The abbreviation, "e.g." is derived from the Latin exempli gratia, and is used herein to indicate a non-limiting example. Thus, the abbreviation "e.g." is synonymous with the term "for example."

In order to facilitate review of the various embodiments of this disclosure, the following explanations of specific terms are provided:

Agent: Any polypeptide, compound, small molecule, organic compound, salt, polynucleotide, or other molecule of interest.

Agonist: An agent that has affinity for and stimulates physiologic activity at cell receptors normally stimulated by naturally occurring substances, thus triggering a biochemical response. An IL-21 and/or IL-21 receptor agonist has affinity for the IL-21 receptors and stimulates an activity induced by the binding of IL-21 with its receptor. In contrast, an "antagonist" is an agent that has affinity for and blocks or inhibits activity of a cell receptor normally stimulated by a naturally occurring substance. Accordingly, an IL-21/IL-21 receptor antagonist binds to the IL-21 receptor and inhibits an activity normally induced by IL-21.

Animal: Living multi-cellular vertebrate organisms, a category that includes, for example, mammals, primates, and birds.

Antibody: Immunoglobulin molecules and immunologically active portions of immunoglobulin molecules, i.e., molecules that contain an antigen binding site which specifically binds (immunoreacts with) an antigen. In one embodiment the antigen is the IL-4 or IL-21. In another embodiment, the antigen is the IL-4 or the IL-21 receptor.

A naturally occurring antibody (e.g., IgG) includes four polypeptide chains, two heavy (H) chains and two light (L) chains inter-connected by disulfide bonds. However, the antigen-binding function of an antibody can be performed by fragments of a naturally occurring antibody. Thus, these antigen-binding fragments are also intended to be designated by the term antibody. Examples of binding fragments encompassed within the term antibody include (i) an Fab fragment consisting of the VL, VH, CL and CH1 domains; (ii) an Fd fragment consisting of the VH and CH1 domains; (iii) an Fv fragment consisting of the VL and VH domains of a single arm of an antibody, (iv) a dAb fragment (Ward et al., *Nature* 341:544-6, 1989) which consists of a VH domain; (v) an isolated complimentarity determining region (CDR); and (vi) an F(ab')$_2$ fragment, a bivalent fragment comprising two Fab fragments linked by a disulfide bridge at the hinge region. Furthermore, although the two domains of the Fv fragment are coded for by separate genes, a synthetic linker can be made that enables them to be made as a single protein chain (known as single chain Fv (scFv); Bird et al. *Science* 242: 423-6, 1988; and Huston et al., *Proc. Natl. Acad. Sci. USA* 85:5879-83, 1988) by recombinant methods. Such single chain antibodies are also included.

Antibodies can be fragmented using conventional techniques and the fragments screened for utility in the same manner as described for whole antibodies. An antibody is further intended to include bispecific and chimeric molecules that specifically bind the target antigen. Antibodies can be derived from any species, such as fully human antibody. Antibodies can be chimeric, such as a humanized mouse monoclonal antibody.

"Specifically binds" refers to the ability of individual antibodies to specifically immunoreact with an antigen, such as Il-4, Il-21, the IL-4 receptor, or the IL-21 receptor, or Bcl-6 or Blimp-1. The binding is a non-random binding reaction between an antibody molecule and an antigenic determinant of the target cytokine or receptor. The desired binding specificity is typically determined from the reference point of the ability of the antibody to differentially bind the target cytokine or receptor and an unrelated antigen, and therefore distinguish between two different antigens, particularly where the two antigens have unique epitopes. An antibody that specifically binds to a particular epitope is referred to as a "specific antibody".

B Cell: A subset of lymphocytes, that is, white blood cells (leukocytes). Mature B cells differentiate into plasma cells, which produces antibodies, and memory B cells. A "B cell progenitor" is a cell that can develop into a mature B cell. B cell progenitors include stem cells, early pro-B cells, late pro-B cells, large pre-B cells, small pre-B cells, and immature B cells and transitional B cells. Generally, early pro-B cells (that express, for example, CD43 or B220) undergo immunoglobulin heavy chain rearrangement to become late pro B and pre B cells, and further undergo immunoglobulin light chain rearrangement to become an immature B cells. Immature B cells include T1 and T2 B cells. For example, in mice, immature B cells include T1 B cells that are AA41$^{hi}$CD23$^{lo}$ cells. Another example of a mouse immature B cell is a T2 B that is an AA41$^{hi}$CD23$^{hi}$ cell. In humans, immature B cells (for example, immature peripheral transitional B cells) include CD38$^{hi}$, IgD$^+$, CD10$^+$, CD24$^{hi}$, CD44$^{lo}$, CD23$^{lo}$ and CD1$^{lo}$ cells. Thus, immature B cells include B220 (CD45R) expressing cells wherein the light and the heavy chain immunoglobulin genes are rearranged. In one embodiment, immature B cells express CD45R, class II, IgM, CD19 and CD40. Immature B cells do not exhibit surrogate light chain expression, but do express Ig αβ and RAG. Immature B cells can develop into mature B cells, which can produce immunoglobulins (e.g., IgA, IgG or IgM). Mature B cells have acquired surface IgM and IgD, are capable of responding to antigen, and express characteristic markers such as CD21 and CD23 (CD23$^{hi}$CD21$^{hi}$ cells). B cells can be activated by agents such as lippopolysaccharide (LPS) or IL-4 and antibodies to IgM. Common biological sources of B cells and B cell progenitors include bone marrow, peripheral blood, spleen and lymph nodes. Plasma cells are terminally differentiated B cells that are the predominant antibody-secreting cells. Memory B cells are small, long-lived B lymphocytes produced following antigen stimulation. Typically, memory B cells express high affinity antigen specific immunoglobulin (B cell receptor) on their cell surface.

Bcl-6: A sequence-specific DNA binding transcriptional repressor. Bcl-6 is a 706-amino-acid nuclear zinc finger protein. Bcl-6 is implicated in the formation of germinal centers and Th2 mediated responses. The Bcl-6 locus is the breakpoint cluster region in B cell lymphomas. The Bcl-6 locus is of 30 kilobases in length containing at least a Bcl-6 gene which codes for a protein. Therefore, the Bcl-6 locus contains both the 5' and 3' flanking region of the coding sequences of the Bcl-6 gene. Antibodies to this protein stain the germinal center cells in lymphoid follicles, the follicular cells and interfollicular cells in follicular lymphoma, some extrafollicular T cells, diffuse large B cell lymphomas, and Burkitt's lymphoma, and the majority of the Reed-Sternberg cells in nodular lymphocyte predominant Hodgkin's disease. Bcl-6 expression is seen in approximately 45% of CD30+ anaplastic large cell lymphomas but is absent in other peripheral T cell lymphomas. The amino acid sequence of Bcl-6 is available on the internet, for example it can be found as EMBL Accession No. Z21943, GENBANK® Accession No. U00115, or as SwissProt database as Accession No. P41182.

Blimp-1: A protein that acts as a repressor of beta-interferon gene expression. The protein binds specifically to the PRDI (positive regulatory domain I element) of the beta-IFN gene promoter. Transcription of this gene increases upon virus induction. Two alternatively spliced transcript variants that encode different isoforms have been reported. The sequence of Blimp-1 can be found on the internet, for example it can be found as GENBANK® Accession No. NP_001189.

CD45: An antigen also known as Leukocyte common antigen or T200. CD45 is a tyrosine phosphatase that augments signaling through antigen receptor of B and T cells. There are multiple isoforms of CD45 (such as CD45RO, CD45RA, CD45RB, CD45 RC and CD45RO) that result from alternative splicing. CD45RO Lacks the A, B, and C exons of CD45, while CD45RA, CD45RB, and CD45RC contain the A, B and C exons respectively. CD45RO, CD45RA, and CD45RB are expressed on B cells. Expression of $CD45R^C$ is restricted to T cells. Mouse B cells are characterized by expression of an isoform of CD45 designated CD45R or B220, uniquely detected by the monoclonal antibody 6B2.

Costimulation: An event or stimulus in addition to antigen binding involved in proliferation or activation of lymphocytes. A costimulation agent is any agent that is capable of promoting proliferation or activation of a lymphocyte. Costimulation agents include lymphocyte specific molecules, such as molecules expressed on the lymphocyte cell surface or soluble forms, or functional agonists thereof, that in combination with binding of antigen or another ligand (such as an antibody that specifically binds to an immunoglobulin) to a cell surface antigen receptor, are capable of inducing proliferation of a lymphocyte. Costimulation agents can also include non-specific lymphocyte activating agents, such as LPS and *Staphylococcus aureus* Cowan I antigen (SAC). Exemplary B cell costimulation agents include agents that bind to CD40 on the surface of a B cell, such as CD40 ligand or anti-CD40 antibody. Exemplary T cell costimulation agents include agents that bind to CD28 and/or CTLA-4, such as B7 and B7.2.

In certain examples disclosed herein, an antibody that specifically binds to CD40 expressed on the surface of a B cell is used as a costimulation agent. In other examples, a polyclonal activators, such as LPS or SAC is used as a costimulation agent (for example, in the absence of antigen). Thus, in certain examples, a B cell progenitor (such as an immature B cell or a transitional B cell), a naïve mature B cell, a memory cell, or a population of cells including at least one of these cell types, is contacted with IL-21 in the presence of a costimulation agent. The costimulation agent can be administered from an exogenous source or can be provided by one or more cells in a mixed population of cells, either in vitro or in vivo.

Cytokine/Interleukin (IL): A generic name for a diverse group of soluble proteins and peptides which act as humoral regulators at nano- to picomolar concentrations and which, either under normal or pathological conditions, modulate the functional activities of individual cells and tissues. These proteins also mediate interactions between cells directly and regulate processes taking place in the extracellular environment. Many growth factors and cytokines act as cellular survival factors by preventing programmed cell death. Cytokines and interleukins include both naturally occurring peptides and variants that retain full or partial biological activity. Although specific cytokines/interleukins are described in the specification, they are not limited to the specifically disclosed peptides.

Deletion: The removal of a sequence of nucleic acid, such as DNA.

DNA (deoxyribonucleic acid): DNA is a long chain polymer which comprises the genetic material of most living organisms (some viruses have genes comprising ribonucleic acid, RNA). The repeating units in DNA polymers are four different nucleotides, each of which comprises one of the four bases, adenine, guanine, cytosine, and thymine bound to a deoxyribose sugar to which a phosphate group is attached. Triplets of nucleotides, referred to as codons, in DNA molecules code for amino acid in a polypeptide. The term codon is also used for the corresponding (and complementary) sequences of three nucleotides in the mRNA into which the DNA sequence is transcribed.

Electroporation: A method of inducing or allowing a cell to take up macromolecules by applying electric fields to reversibly permeabilize the cell walls. Various methods and apparatuses used are further defined and described in: U.S. Pat. No. 4,695,547; U.S. Pat. No. 4,764,473; U.S. Pat. No. 4,882,281; U.S. Pat. No. 4,946,793; U.S. Pat. No. 4,906,576; U.S. Pat. No. 4,923,814; and U.S. Pat. No. 4,849,089.

Eukaryotic cell: A cell having an organized nucleus bounded by a nuclear membrane. These include simpler organisms such as yeasts, slime molds, and the like, as well as cells from multicellular organisms such as invertebrates, vertebrates, and mammals. A eukaryotic cell can be, for example, an endothelial cell, a smooth muscle cell, an epithelial cell, a hepatocyte, a cell of neural crest origin, a tumor cell, a hematopoetic cell, an immunologic cell, (e.g., a T cell, a B cell, a monocyte, a macrophage, a dendritic cell), a fibroblast, a keratinocyte, a neuronal cell, a glial cell, an adipocyte, a myoblast, a myocyte, a chondroblast, a chondrocyte, an osteoblast, an osteocyte, an osteoclast, a secretory cell, an endocrine cell, an oocyte, and a spermatocyte. These cell types are described in standard histology texts, such as McCormack, *Introduction to Histology*, © 1984 by J. P. Lippincott Co.; Wheater et al., eds., *Functional Histology*, 2nd Ed., © 1987 by Churchill Livingstone; Fawcett et al., eds., *Bloom and Fawcett: A Textbook of Histology*, © 1984 by William and Wilkins.

Gene: A functional DNA sequence. For example, a gene can include control and/or coding sequences necessary for the production of an RNA or a polypeptide, such as a protein. Where a gene encodes a polypeptide, the polypeptide can be encoded by a full-length coding sequence or by any portion (or subsequence) of a full length coding sequence, so long as at least a part of the functional activity of the polypeptide is retained.

Heterologous or foreign gene: A gene that is introduced into the genome of a cell or organism, such as a multicellular animal, by experimental manipulations and can include polynucleotide sequences found in that cell or organism so long as the introduced gene contains some modification (e.g., a point mutation, the presence of a selectable marker gene, a non-native regulatory sequence, or a native sequence integrated into the genome at a non-native location, etc.) relative to the naturally-occurring gene. More broadly, a heterologous or foreign nucleic acid is any nucleic acid regardless of its functional attributes that does not originate in the cell or organism in which it is located, or does not exist in association with the nucleic acids in which it is associated upon introduction into the cell or organism.

Interleukin (IL)-4: IL-4 is a protein produced mainly by a subpopulation of activated T cells (CD4+TH2 cells), which also secrete IL-5 and IL-6. IL-4 is 129 amino acids (20 kDa) that is synthesized as a precursor containing a hydrophobic secretory signal sequence of 24 amino acids. IL-4 is glycosylated at two arginine residues (positions 38 and 105) and contains six cysteine residues involved in disulfide bond formation. Some glycosylation variants of IL-4 have been described that differ in their biological activities. A comparison of murine and human IL-4 shows that both proteins only diverge at positions 91-128.

The human IL-4 gene contains four exons and has a length of approximately 10 kb. It maps to chromosome 5q23-31, while the murine gene maps to chromosome 11. At the nucleotide level the human and the murine IL-4 gene display approximately 70% homology.

The biological activities of IL-4 are species-specific; mouse IL-4 is inactive on human cells and human IL-4 is inactive on murine cells. IL-4 promotes the proliferation and differentiation of activated B cells, the expression of class II MHC antigens, and of low affinity IgE receptors in resting B cells. In addition, IL-4 is known to enhance expression of class II MHC antigens on B cells. This cytokine also can promote the B cells' capacity to respond to other B cell stimuli and to present antigens for T cells.

The classical detection method for IL-4 is a B cell costimulation assay measuring the enhanced proliferation of stimulated purified B cells. IL-4 can be detected also in bioassays, employing IL4-responsive cells (e.g., BALM-4, BCL1, CCL-185, CT.4S, amongst others). A specific detection method for human IL-4 is the induction of CD3 in a number of B cell lines with CD23 detected either by flow-through cytometry or by a fluorescence immunoassay. An alternative and entirely different detection method is RT-PCR (for review see: Boulay and Paul, *Current Opinion in Immunology* 4:294-8, 1992; Paul and Ohara, *Annual Review of Immunology* 5:429-59, 1987).

IL-21: A cytokine cloned from a cDNA library derived from activated CD3+ T cells (Parrish-Novak et al., *Nature* 408:57-63, 2000). The IL-21 cDNA encodes a secreted protein of 131 amino acids protein most closely related to IL-2 and IL-15. The IL-21 gene has been mapped to human chromosome 4q26-q27 near the IL-2 gene.

IL-21 mRNA has been demonstrated to be expressed in activated CD4+ cells, but not in other T cells, B cells, or monocytes (Parrish-Novak et al., *Nature* 408:57-63, 2000). However, it has been demonstrated that IL-21 stimulates proliferation of B cells that are stimulated by cross-linking of the CD40 antigen and proliferation of B cells stimulated by IL-4 in addition to anti-IgM. IL-21 has also been shown to stimulate proliferation of naïve (CD45RA (+)) cells, mediated by engagement of CD3. IL-21 has also been shown to stimulate the proliferation of bone marrow progenitor to cells and to enhance the expression of the NK cell marker CD56 in the presence of IL-15. (For review, see Horst Ibelgaufts' *COPE: Cytokines Online Pathfinder Encyclopedia*, available on the internet).

The IL-21 receptor has been isolated and was found to be expressed by CD23+B cells, B cell lines, a T cell leukemia line, and NK cell lines. The receptor gene has been mapped to human chromosome 16p12 (see Parrish-Novak et al., *Nature* 408:57-63, 2000; Ozaki et al., *Proc. Natl. Acad. Sci. USA* 97:11439-11444, 2000).

The receptor, which is 538 amino acids in length, is most closely related to human IL-2 beta receptor, and contains a WSXWS motif in the extracellular region, typical of type-1 cytokine receptors.

Immunoglobulins: A class of proteins found in plasma and other body fluids that exhibits antibody activity and binds with other molecules with a high degree of specificity; divided into five classes (IgM, IgG, IgA, IgD, and IgE) on the basis of structure and biological activity. The IgG class has been further divided into the IgG1, IgG2a, IgG2b, IgG4 and IgG4 subtypes. Immunoglobulins and certain variants thereof are known and many have been prepared in recombinant cell culture (e.g., see U.S. Pat. No. 4,745,055; U.S. Pat. No. 4,444,487; WO 88/03565; EP 256,654; EP 120,694; EP 125, 023; Faoulkner et al., *Nature* 298:286, 1982; Morrison, *J. Immunol.* 123:793, 1979; Morrison et al., *Ann Rev. Immunol* 2:239, 1984).

A native (naturally occurring) immunoglobulin is each is made up of four polypeptide chains. There are two long chains, called the "heavy" or "H" chains which weigh between 50 and 75 kilodaltons and two short chains called "light" or "L" chains weighing in at 25 kilodaltons. They are linked together by what are called disulfide bonds to form a "Y" shape molecule. Each heavy chain and light chain can be divided into a variable region and a constant region. An Fc region includes the constant regions of the heavy and the light chains, but not the variable regions.

Isolated or purified: An isolated biological component (such as a nucleic acid, peptide or protein disclosed herein) has been substantially separated, produced apart from, or purified away from other biological components in the cell of the organism in which the component naturally occurs, such as other chromosomal and extrachromosomal DNA and RNA, and proteins. Nucleic acids, peptides and proteins that have been isolated include nucleic acids and proteins purified by standard purification methods. The term also embraces nucleic acids, peptides, and proteins prepared by recombinant expression in a host cell as well as chemically synthesized nucleic acids. Isolated or purified compositions can be produced, for example, by standard purification techniques, or by recombinant techniques. In some embodiments, a preparation of a polypeptide is purified such that the protein represents at least 50%, for example at least 70%, of the total polypeptide content of the preparation.

An "isolated" cell is a cell that has been purified from the other cellular components of a tissue. Cells can be isolated by mechanical and/or enzymatic methods. In several embodiments, an isolated population of cells includes greater than about 80%, about 85%, about 90%, about 95%, or greater than about 99% of the cells of interest. In another embodiment, an isolated population of cells is one in which no other cells of a different phenotype can be detected. In a further embodiment, an isolated population of cells is a population of cells that includes less than about 20%, about 15%, about 10%, about 5%, or less than about 1% of a cells of a different phenotype than the cells of interest.

Janus Activated kinase (JAK)/Signal Transducer and Activator of Transcription (STAT): JAKs are cytoplasmic tyrosine kinases that are either constitutively associated with cytokine receptors or recruited to receptors after ligand binding. In either case, stimulation with the ligand results in the catalytic activation of receptor-associated JAKs. This activation results in the tyrosine phosphorylation of cellular substrates, including the JAK-associated cytokine receptor chains. Some of these phosphoylated tyrosines can serve as coding sites for STAT proteins, which bind to the phsphotyrosines by their SRC-homology 2 (SH2) domains. STAT proteins are also phosphylated on a conserved tyrosine residue, resulting in their dimerization and acquisition of high-affinity DNA-binding activity, which facilitates their action as nuclear transcription factors.

The JAK/STAT pathway is one of the most rapid cytoplasmic to nuclear signaling mechanisms. There are a total of four JAK (JAK1-3 and tyrosine kinase 2) and seven STAT proteins (STAT1-4, STAT5A, STAT5b and STAT6). JAKs are relatively large cytoplasmic kinases of about 1,100 amino acids in length, and range in size from about 116 kDa to about 140 kDa. Binding of IL-21 activates a JAK/STAT signaling pathway. Specifically IL-21 activates JAK1 and JAK3, which then phosphorylate cellular substrates, including one of the IL-21 receptor chains. This allows recruitment of STAT 5A and STAT5B proteins to the phosphorylated receptor by their SH2 domains, which in turn, are also phosphorylated. The STAT proteins can dimerize, translocate to the nucleus, and bind DNA. Binding of the STAT proteins to the DNA results in transcription being activated (for review see Leonard, *Nature Reviews* 1: 200-208, 2001).

Lineage specific marker: A marker that is expressed by a specific population of cells. In one embodiment, the cells are cells of a blood vessel, other than endothelial cells, such as smooth muscle cells. In another embodiment, the cells are a population of immune cells, such as lymphocytes. In one specific, non-limiting example, the marker is a B cell specific marker, such as B220. In another specific, non-limiting example, the marker is a T cell specific marker, such as CD3, CD4, or CD8.

Mammal: This term includes both human and non-human mammals. Similarly, the terms "subject," "patient," and "individual" include human and veterinary subjects.

Memory and Plasma B Cells: After a B cell progenitor (e.g., a pre-committed small lymphocyte) is stimulated by an antigen, it differentiates into a blast cell, which differentiates into an immature plasma cell that can differentiate into either a mature plasma cell or a memory B cell. A mature plasma cell secretes immunoglobulins in response to a specific antigen.

A memory B cell is a B cell that undergoes isotype switching and somatic hypermutation that are generally found during a secondary immune response (a subsequent antigen exposure following a primary exposure) but can also be detected during a primary antigen response. Generation of memory B cells generally requires helper T cells. The development of memory B cells takes place in germinal centers (GC) of lymphoid follicles where antigen-driven lymphocytes undergo somatic hypermutation and affinity selection, presumably under the influence of helper T cells.

Neutralizing amount: An amount of an agent sufficient to decrease the activity or amount of a substance to a specified level, for example, to an undetectable level, using a standard method.

Nucleic acid: A biological polymer, a polynucleotide, consisting of deoxyribonucleotides and/or ribonucleotides, for example, a DNA or an RNA polymer. The term nucleic acid also includes polymers comprising both deoxyribonucleotides and ribonucleotides, and/or synthetic analogues thereof.

Oligonucleotide: A linear polynucleotide sequence of up to about 200 nucleotides in length, for example a polynucleotide (such as DNA or RNA) which is at least 6 nucleotides, for example at least 12, 15, 20, 30, 50, 100 or even 200 nucleotides long.

Operably linked: A first nucleic acid sequence is operably linked to a second nucleic acid sequence when the first nucleic acid sequence is placed in a functional relationship with the second nucleic acid sequence. For instance, a coding sequence is operably linked to a promoter if the promoter affects the transcription or expression of the coding sequence. Generally, operably linked DNA sequences are contiguous and, where necessary, for example, to join two protein coding regions, in the same reading frame.

Pharmaceutically acceptable carriers (excipients): The pharmaceutically acceptable carriers useful with the methods described herein are conventional. *Remington's Pharmaceutical Sciences*, by E. W. Martin, Mack Publishing Co., Easton, Pa., 15th Edition (1975), describes compositions and formulations suitable for pharmaceutical delivery of the cytokines and cells disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polynucleotide: A biological polymer in which the monomers are nucleotides, such as ribonucleotides, deoxyribonucleotides or a combination thereof. Optionally, a polynucleotide can include one or more nucleotide analog. The term polynucleotide encompasses a nucleotide polymer of any length. Therefore, a polynucleotide includes molecules that are at least 15, 25, 50, 100, or 200 (oligonucleotides) and also nucleotides as long as a full-length cDNA, e.g., several kilobases or longer. The term polynucleotide sequence refers to the sequential array of nucleotides in a polynucleotide. Typically, a polynucleotide sequence is represented as a series of letters (a, c, g, and t or u) each of which represents a deoxyribonucleotide or a ribonucleotide (that is, adenine, cytosine, guanine, thymine and uracil, respectively).

Polypeptide: A biological polymer in which the monomers are amino acid residues that are joined together through amide bonds. When the amino acids are alpha-amino acids, either the L-optical isomer or the D-optical isomer can be used, the L-isomers being preferred in nature. The term polypeptide or protein as used herein encompasses any amino acid sequence and includes, but is not limited to, modified sequences such as ADP-ribosylated proteins, ribosyl-proteins, and glycoproteins. The term polypeptide is specifically intended to cover naturally occurring proteins, such as IL-21, as well as polypeptides (e.g., IL-21) that are recombinantly or synthetically produced.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);

5) Isoleucine (I), Leucine (L), Methionine (M), Valine (V); and

6) Phenylalanine (F), Tyrosine (Y), Tryptophan (W).

Any cDNA sequence variant will preferably introduce no more than twenty, and preferably fewer than ten amino acid substitutions into the encoded polypeptide. For example, an IL-21 variant polypeptide can have as many as ten or five amino acid substitutions, but often will have no more than three, or two or one amino acid substitutions. In some instances, an IL-21 polypeptide will have 1, or 2, or 3, or more, conservative amino acid substitutions. Variant amino acid sequences can, for example, be 80%, 90% or even 95% or 98% identical to the native amino acid sequence. Programs and algorithms for determining percentage identity can be found at the NCBI website.

Sample (Biological sample): Includes biological samples containing fluids, tissues, cells, and subcomponents thereof, such as DNA, RNA, and proteins. For example, common samples in the context of the present invention include bone marrow, spleen, lymph node, blood, e.g., peripheral blood (but can also include any other source from which B cells or B cell progenitors can be isolated, including: urine, saliva, tissue biopsy, surgical specimens, fine needle aspirates, autopsy material, and the like).

Sequence identity: For any sequences disclosed herein, the similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are. Homologues of an IL-2 receptor polypeptide or a gene encoding an IL-21 receptor polypeptide, will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. USA* 85:2444, 1988; Higgins and Sharp, *Gene* 73:237, 1988; Higgins and Sharp, *CABIOS* 5:151, 1989; Corpet, et al., *Nucleic Acids Research* 16:10881, 1988; and Pearson and Lipman, *Proc. Natl. Acad. Sci. USA* 85:2444, 1988. Altschul et al., *Nature Genet.*, 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Specific binding agent: An agent that binds substantially only to a defined target. Thus an IL-21 receptor specific binding agent is an agent that binds substantially to an IL-21 receptor. In one embodiment, the specific binding agent is a monoclonal or polyclonal antibody that specifically binds the IL-21 receptor.

The term "specifically binds" refers with respect to an antigen, such as the IL-21 receptor, to the preferential association of an antibody or other ligand, in whole or part, with a cell or tissue bearing that antigen and not to cells or tissues lacking that antigen. It is, of course, recognized that a certain degree of non-specific interaction may occur between a molecule and a non-target cell or tissue. Nevertheless, specific binding can be distinguished as mediated through specific recognition of the receptor or antigen. Specific binding results in a much stronger association between the antibody (or other ligand) and cells bearing the antigen than between the bound antibody (or other ligand) and cells lacking the antigen. Specific binding typically results in greater than 2-fold, preferably greater than 5-fold, more preferably greater than 10-fold and most preferably greater than 100-fold increase in amount of bound antibody or other ligand (per unit time) to a cell or tissue bearing IL-21 receptor as compared to a cell or tissue lacking IL-21 receptor. Specific binding to a protein under such conditions requires an antibody that is selected for its specificity for a particular protein. A variety of immunoassay formats are appropriate for selecting antibodies or other ligands specifically immunoreactive with a particular protein. For example, solid-phase ELISA immunoassays are routinely used to select monoclonal antibodies specifically immunoreactive with a protein. See Harlow & Lane, *Antibodies, A Laboratory Manual*, Cold Spring Harbor Publications, New York (1988), for a description of immunoassay formats and conditions that can be used to determine specific immunoreactivity.

Substantially purified: The term substantially purified indicates that the subject is substantially free of other molecular or cellular constituents with which it is naturally associated. Thus, a substantially purified polypeptide as is a polypeptide that is substantially free of other proteins, lipids, carbohydrates or other materials with which it is naturally associated, for example, in a cell. In one embodiment, the polypeptide is at least 50%, for example at least 80% free of other proteins, lipids, carbohydrates or other materials with which it is naturally associated. In another embodiment, the polypeptide is at least 90% free of other proteins, lipids, carbohydrates or other materials with which it is naturally associated. In yet another embodiment, the polypeptide is at least 95% free of other proteins, lipids, carbohydrates or other materials with which it is naturally associated. A substantially purified population of cells (such as B cells, B cell progenitors, mature B cells, memory B cells, plasma cells, etc.) is substantially free of other cellular components of the tissue in which it is naturally found, such as bone marrow, peripheral blood, spleen, lymph node, etc. For example, a substantially pure population of B cells (e.g., a B cell progenitor, an immature B cell, a mature B cell, a memory B cell, a plasma cell, etc.) is at least 50%, for example at least about 80% or alternatively at least about 90% free of other cellular components. In an embodiment, the population of B cells is at least about 95% free of other cells. For example, a population of purified B cells, obtained from a tissue such as peripheral blood, is substantially free of red blood cells, T cells, platelets, and other cells typically found in peripheral blood.

Subject: Living multicellular vertebrate organisms, a category that includes both human and veterinary subjects for example, mammals, birds and primates.

Supernatant: The culture medium in which a cell is grown. The culture medium can include material from the cell, such as materials produced within the cell and/or secreted by the cell, such as cytokines and interleukins.

Therapeutically Effective Amount: An amount sufficient to achieve a desired biological effect, for example an amount that is effective to induce the differentiation of memory B or plasma cells. In particular examples, it is an amount of an agent, such as IL-21, effective to induce B cell differentiation in a subject, such as in a subject to whom it is administered (for example a subject with a deficiency of memory B cells or plasma cells). In another particular example, a therapeutically effective amount is an amount of IL-21 that alters a sign or a symptom of a disorder in a subject, such as a subject with a deficiency of memory B cells or plasma cells.

An effective amount of an agent such as IL-21 can be administered in a single dose, or in several doses, for example daily, during a course of treatment. However, the effective amount of IL-21 will be dependent on the subject being treated, the severity and type of the condition being treated, and the manner of administration. The methods disclosed herein have equal application in medical and veterinary settings. Therefore, the general term "subject being treated" is understood to include all organisms (e.g., humans, apes, dogs, cats, horses, and cows) that require an increase in the desired biological effect, such as an enhanced immune response.

Transgene: A heterologous nucleic acid ("foreign gene") that is placed into an organism by introducing the nucleic acid into embryonic stem (ES) cells, newly fertilized eggs or early embryos. In one embodiment, a transgene is a polynucleotide sequence that encodes a polypeptide, for example a sequence that encodes a marker polypeptide that can be detected using methods known to one of skill in the art. In another embodiment, the transgene encodes a therapeutic polypeptide that can be used to alleviate or relieve a symptom of a disorder. In yet another embodiment, the transgene encodes a therapeutically effective oligonucleotide, for example an antisense oligonucleotide, wherein expression of the oligonucleotide inhibits expression of a target nucleic acid sequence. In a further embodiment, the transgene encodes an antisense nucleic acid or a ribozyme. In yet another embodiment, a transgene is a stop cassette.

In other embodiments, a transgene contains native regulatory sequences operably linked to the transgene (e.g., the wild-type promoter, found operably linked to the gene in a wild-type cell). Alternatively, a heterologous promoter can be operably linked to the transgene. In yet another embodiment, a viral LTR can be used to express the transgene.

Transgenic Cell: Transformed cells that contain heterologous or foreign, DNA.

Transgenic Animal: An animal, for example, a non-human animal such as a mouse, that has a heterologous nucleic acid or foreign gene introduced into one or more of its cells. A transgene can be inserted into the genome of an animal by random integration or by targeted insertion. For example, DNA can be integrated in a random fashion by injecting it into the pronucleus of a fertilized ovum. In this case, the DNA can integrate anywhere in the genome, and multiple copies often integrate in a head-to-tail fashion. There is no need for homology between the injected DNA and the host genome.

Targeted insertion is accomplished by introducing the DNA into embryonic stem (ES) cells and selecting for cells in which the DNA has undergone recombination with homologous genomic sequences. For this to occur, there often are several kilobases of sequence identity or similarity between the heterologous and genomic DNA, and positive selectable markers are often included. In addition, negative selectable markers are often used to select against cells that have incorporated DNA by non-homologous recombination (random insertion).

Vector: A means by which a nucleic acid molecule can be replicated or manipulated, e.g., introduced into a cell. A vector can include nucleic acid sequences that permit it to replicate in the cell, such as an origin of replication. A vector can also include one or more marker or therapeutic transgenes and other genetic elements known in the art. Common vectors include viral vectors, phage vectors (e.g., adenoviral vectors, retroviral vectors, and Herpes viral vectors), bacterial vectors (such as plasmid vectors) and artificial chromosomes.

Wild-type: The term "wild-type" refers to a gene or gene product which has the characteristics of that gene or gene product when isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and/or functional properties (i.e. altered characteristics) when compared to the wild-type gene or gene product. It is noted that naturally-occurring mutants can be isolated; these are typically identified by the fact that they have altered characteristics when compared to the wild-type gene or gene product.

IL-21 Polypeptides and Polynucleotides

IL-21 polypeptides and polynucleotides encoding these polypeptides are used in the methods disclosed herein. A nucleic acid sequence and polypeptide sequence for murine IL-21 is available at the NCBI website as GENBANK® Accession No. NM021782 and GENBANK® Accession No. AF254070. A nucleic acid and polypeptide sequence of human IL-21 is available at the NCBI website as GENBANK® Accession No. NM021803 and GENBANK® Accession No. AF254069. These GENBANK® entries are incorporated by reference herein.

In one specific, non-limiting example, a human IL-21 polypeptide has the following amino acid sequence

```
                                                (SEQ ID NO: 1)
MRSSPGNMERIVICLMVIFLGTLVHKSSSQGQDRHMIRMRQLID

IVDQLKNYVNDLVPEFLPAPEDVETNCEWSAFSCFQKAQLKSANTGNNER

IINVSIKKLKRKPPSTNAGRRQKHRLTCPSCDSYEKKPPKEFLERFKSLL

QKMIHQHLSSRTHGSE
```

In another specific, non-limiting example, a murine IL-21 has an amino acid sequence set forth as

```
                                                (SEQ ID NO: 2)
MERTLVCLVVIFLGTVAHKSSPQGPDRLLIRLRHLIDIVEQLKIYENDLD

PELLSAPQDVKGHCEHAAFACFQKAKLKPSNPGNNKTFIIDLVAQLRRRL

PARRGGKKQKHIAKCPSCDSYEKRTPKEFLERLKWLLQKMIHQHLS
```

Furthermore, sequence of human IL-21 is shown as SEQ ID NO: 1 in U.S. Published Patent Application No. 2003/0003545, which is incorporated herein, by reference. A representative clone containing all or most of the sequence for IL-21 (designated HTGED19) was deposited with the American Type Culture Collection ("ATCC") on Mar. 5, 1998, and was given the ATCC Deposit Number 209666 (see, e.g., U.S. Published Patent Application No. 2003/0003545).

IL-21 polypeptides (including variant polypeptides and IL-21 polypeptide analogs, such as IL-21 agonists), can be composed of amino acids joined to each other by peptide bonds or modified peptide bonds, such as, peptide isosteres, and can contain amino acids other than the 20 gene-encoded amino acids. The IL-21 polypeptides can be modified by either natural processes, such as posttranslational processing, or by chemical modification techniques which are well known in the art. Modifications can occur anywhere in the IL-21 polypeptides, including the peptide backbone, the amino acid side-chains and the amino or carboxyl termini. IL-21 polypeptides can be branched, for example, as a result of ubiquitination, and they can be cyclic, with or without branching. Cyclic, branched, and branched cyclic IL-21 polypeptides can result from post-translation natural processes or can be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination.

Variants of IL-21, or polynucleotides encoding these variants, can also be used in the methods disclosed herein. U.S. Published Patent Application No. 2003/0003545 discloses polynucleotide or polypeptide differing from the IL-21 polynucleotides or polypeptides, but retaining essential properties thereof. Generally, variants are overall closely similar, and, in many regions, identical to the IL-21 polynucleotide or polypeptide. For example, a variant of an IL-21 polynucleotide is a polynucleotide having a nucleotide sequence at least, for example, a polynucleotide can be at least 90% "identical" to a reference IL-21 nucleotide sequence, such as at least 95%, 96%, 97%, 98% or 99% identical to a reference IL-21 sequence. Thus, the nucleotide sequence of the polynucleotide is identical to the reference sequence except that the polynucleotide sequence can include up to five point mutations per each 100 nucleotides of the reference nucleotide sequence encoding the IL-21 polypeptide.

IL-21 variants have been described that contain alterations in the coding regions, non-coding regions, or both. In one specific, non-limiting example, polynucleotide variants of IL-21 contain alterations which produce silent substitutions, additions, or deletions, but do not alter the properties or activities of IL-21, such as a variant produced by the degeneracy of the genetic code. Moreover, variants in which 5-10, 1-5, or 1-2 amino acids are substituted, deleted, or added in any combination have been described (see, U.S. Published Patent Application No. 2003/0003545). Using known methods of protein engineering and recombinant DNA technology, variants can be generated to improve or alter the characteristics of the IL-21 polypeptides. For instance, one or more amino acids can be deleted from the N-terminus or C-terminus of the secreted protein without substantial loss of biological function (see, U.S. Published Patent Application No. 2003/0003545). In several examples, one, two, three, four or five amino acids are deleted from the N-terminus, the C-terminus, or both.

One of skill in the art can readily produce polynucleotide sequences encoding this polypeptide, and can use genetic engineering to operably link promoters to the polynucleotides sequences, and produce vectors encoding this polypeptide using standard laboratory techniques (see, for example, Sambrook et al., *Molecular Cloning: a Laboratory Manual*, Cold Spring Harbor Press, 1989).

Polynucleotides encoding an IL-21, including variants and analogs of IL-21, such as IL-21 agonists and antagonists, are also of use in the methods disclosed herein. These polynucleotides include DNA, cDNA and RNA sequences which encode an IL-21 or a variant or analog thereof. It is understood that all polynucleotides encoding an IL-21 are also included herein, as long as they encode a polypeptide that has an activity of IL-21 (that is, are agonist polypeptides), such as the ability to induce apoptosis of a B cell. Such polynucleotides include naturally occurring, synthetic, and intentionally manipulated polynucleotides. For example, a polynucleotide encoding IL-21 can be subjected to site-directed mutagenesis. The polynucleotides include sequences that are degenerate as a result of the genetic code, but encode IL-21. There are 20 natural amino acids, most of which are specified by more than one codon. Therefore, all degenerate nucleotide sequences are of use in the methods disclosed herein as long as the amino acid sequence of the IL-21 encoded by the nucleotide sequence is functionally unchanged.

DNA sequences encoding an IL-21 can be expressed in vitro by DNA transfer into a suitable host cell. Methods of stable transfer, meaning that the foreign DNA is continuously maintained in the host, are known in the art.

Polynucleotide sequences encoding an IL-21, including IL-21 variants and analogs, can be inserted into an expression vector, such as a plasmid, virus or other vehicle known in the art that has been manipulated by insertion or incorporation of the IL-21 sequences. Polynucleotide sequences which encode an IL-21 can be operatively linked to expression control sequences. In one embodiment, an expression control sequence operatively linked to a coding sequence is ligated such that expression of the coding sequence is achieved under conditions compatible with the expression control sequences.

The polynucleotide encoding an IL-21, such as human IL-21, can be inserted into an expression vector that contains a promoter sequence which facilitates the efficient transcription of the inserted genetic sequence by the host. The expression vector typically contains an origin of replication, a promoter, as well as specific genes that allow phenotypic selection of the transformed cells. Vectors suitable for use include, but are not limited to, the T7-based expression vector for expression in bacteria (Rosenberg et al., *Gene* 56:125, 1987), the pMSXND expression vector for expression in mammalian cells (Lee and Nathans, *J. Biol. Chem.* 263:3521, 1988) and baculovirus-derived vectors for expression in insect cells. The DNA segment can be present in the vector operably linked to regulatory elements, for example, a promoter (e.g., T7, metallothionein I, or polyhedrin promoters).

Polynucleotide sequences encoding IL-21 can be expressed in either prokaryotes or eukaryotes. Hosts can include microbial, yeast, insect and mammalian organisms. Methods of expressing DNA sequences having eukaryotic or viral sequences in prokaryotes are well known in the art. For example, biologically functional viral and plasmid DNA vectors capable of expression and replication in a host are known in the art. Such vectors are used to incorporate a DNA sequence encoding an IL-21. Transfection of a host cell with recombinant DNA can be carried out by conventional techniques and are well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, methods of transfection of DNA as calcium phosphate co-precipitates, conventional mechanical procedures such as microinjection, electroporation, insertion of a plasmid encased in liposomes, or virus vectors can be used. Eukaryotic cells can also be cotransformed with a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982).

Isolation and purification of microbial expressed IL-21 polypeptide, or fragments thereof, can be carried out by conventional means including preparative chromatography, affinity column chromatography, and immunological separations involving monoclonal or polyclonal antibodies, and used in the methods disclosed herein.

Methods of Inducing B Cell Differentiation

Methods are provided herein for expanding and/or inducing differentiation of a B cell progenitor, (such as an immature B cell), and/or a mature naïve or memory B cell into a memory B cell or a plasma cell. For example, the methods include inducing differentiation of a B cell progenitor or a naïve mature B cell into a memory cell or a plasma cell. The methods also include inducing differentiation of a memory cell into a plasma cell, as well as inducing expansion of memory cells. The methods involve contacting an immature, naïve or memory B cell with a therapeutically effective amount of an agent that activates JAK1, JAK3, STAT5A or STAT5B and isolating a plasma cell and/or a memory cell, thereby producing differentiated plasma cells and/or memory B cells. In one embodiment, the agent is an IL-21 polypeptide or an IL-21 agonist. The B cell progenitors (e.g., immature B cells, such as transitional B cells), naïve B cells and/or memory B cells can be included in a mixed population of cells, or can be a purified or enriched populations of cells. The cells can be from any mammal. In one example, the cells are human cells.

In one embodiment, a B cell progenitor (e.g., an immature B cell, such as a transitional B cell), naïve B cell, and/or memory cell is contacted with IL-21 or an IL-21 agonist in vitro. Thus, in order to induce differentiation, a population of cells including the B cell progenitor, naïve B cell and/or memory B cell is isolated from a subject and then contacted with an effective amount of IL-21 polypeptide or an agonist thereof. The immature B cells, naïve mature B cells and/or memory cells can be purified populations of cells, or can be included in a mixed population of cells that are isolated from the subject, such as bone marrow derived cells, cord blood cells or peripheral blood cells.

In another embodiment, a population of cells including immature, naïve or memory B cells is obtained from a subject, contacted with a therapeutically effective amount of IL-21 or an agonist thereof, and plasma cells and/or memory cells are isolated. Typically, a substantially pure population of plasma cells and/or memory B cells are isolated. Optionally, a mixed population is isolated. Typically, where a mixed population of cells is isolated, it is enriched for plasma cells and/or memory B cells. The isolated plasma cells and/or memory cells are then introduced into the same subject (autologous) or another subject (heterologous).

In another embodiment, in order to enhance an immune response, a population of cells including a B cell progenitor, (such as an immature B cell or transitional B cell), a naïve B cell, or a memory B cell is contacted with IL-21 or an agonist thereof. Memory B cells and/or plasma cells are isolated and the memory B cells and/or the plasma cells are introduced into a subject. The subject can be any mammalian subject, such as, but not limited to, a human subject. The population of cells including the B cell progenitor, naïve mature B cell or memory cell can be further contacted with an antigen. The antigen can be any antigen of interest, including, but not limited to, antigens from a virus, bacteria, or parasite. In one embodiment, the B cell progenitors, naïve B cells or memory B cells are contacted with IL-21 and an antigen, either sequentially or simultaneously.

Fluorescence activated cell sorting (FACS) can be used to sort (isolate) cells, such as various populations of immature and mature B cells or differentiated plasma cells or memory cells, by contacting the cells with an appropriately labeled antibody. In one embodiment, several antibodies (such as antibodies that bind CD19, IgD, CD38, CD27 and/or IgM) and FACS sorting can be used to produce substantially purified populations of immature B cells, plasma cells and or memory B cells. These methods are known in the art, and exemplary protocols are described below.

A FACS employs a plurality of color channels, low angle and obtuse light-scattering detection channels, and impedance channels, among other more sophisticated levels of detection, to separate or sort cells. Any FACS technique can be employed as long as it is not detrimental to the viability of the desired cells. (For exemplary methods of FACS see U.S. Pat. No. 5,061,620).

However, other techniques of differing efficacy can be employed to purify and isolate desired populations of cells. The separation techniques employed should maximize the retention of viability of the fraction of the cells to be collected. The particular technique employed will, of course, depend upon the efficiency of separation, cytotoxicity of the method, the ease and speed of separation, and what equipment and/or technical skill is required.

Separation procedures include magnetic separation, using antibody-coated magnetic beads, affinity chromatography, cytotoxic agents, either joined to a monoclonal antibody or used in conjunction with complement, and "panning," which utilizes a monoclonal antibody attached to a solid matrix, or another convenient technique. Antibodies attached to magnetic beads and other solid matrices, such as agarose beads, polystyrene beads, hollow fiber membranes and plastic petri dishes, allow for direct separation. Cells that are bound by the antibody can be removed from the cell suspension by simply physically separating the solid support from the cell suspension. The exact conditions and duration of incubation of the cells with the solid phase-linked antibodies will depend upon several factors specific to the system employed. The selection of appropriate conditions, however, is well within the skill in the art.

The unbound cells then can be eluted or washed away with physiologic buffer after sufficient time has been allowed for the cells expressing a marker of interest (e.g., CD45) to bind to the solid-phase linked antibodies. The bound cells are then separated from the solid phase by any appropriate method, depending mainly upon the nature of the solid phase and the antibody employed.

Antibodies can be conjugated to biotin, which then can be removed with avidin or streptavidin bound to a support, or fluorochromes, which can be used with a fluorescence activated cell sorter (FACS), to enable cell separation.

For example, cells expressing CD45 are initially separated from other cells by the cell-surface expression of CD45. In one specific, non-limiting example, $CD45^+$ cells are positively selected by magnetic bead separation, wherein magnetic beads are coated with CD45 reactive monoclonal antibody. The $CD45^+$ cells are then removed from the magnetic beads.

Release of the CD45+ cells from the magnetic beads can effected by culture release or other methods. Purity of the isolated CD45+ cells is then checked with a FACSCAN®. flow cytometer (Becton Dickinson, San Jose, Calif.), for example, if so desired. In one embodiment, further purification steps are performed, such as FACS sorting the population of cells released from the magnetic beads. In one example, this sorting can be performed to detect expression of CD19, CD44, CD21, CD62L, and CD10 to detect or isolate immature B cells. In another example, mature B cells can be isolated and/or detected on the basis of expression of CD19, IgD, CD38, CD27, CD21, and/or CD23.

In a further specific, non-limiting example, the immature B cell is in vivo. Thus, a therapeutically effective amount of IL-21 or an agonist thereof is administered to the subject, in order to induce differentiation of the immature B cell into a plasma cell or a memory cell. The subject can be any subject of interest, including subjects with a deficiency of memory B cells, plasma cells, or both. In one embodiment, the subject has a specific immunodeficiency, such as a deficiency that results in a reduction in number or function of memory B cells, and or plasma cells. In one example, the subject has a B cell deficiency after bone marrow transplantation, e.g., after allogeneic bone marrow transplantation. In other examples, the subject has transient hypgammaglobulinemia of childhood, Hyper-IgM syndrome, X-linked agammagloulinemia, common variable immunodeficiency, ataxia teleangiectasia, or a selective IgA or IgG subclass deficiency.

An IL-21 polypeptide or an agonist thereof can be administered by any means known to one of skill in the art (see Banga, "Parenteral Controlled Delivery of Therapeutic Peptides and Proteins," in *Therapeutic Peptides and Proteins*, Technomic Publishing Co., Inc., Lancaster, Pa., 1995) such as by intramuscular, subcutaneous, or intravenous injection, but even oral, nasal, or anal administration is contemplated. In one embodiment, administration is by subcutaneous or intravascular injection. To extend the time during which the peptide or protein is available to stimulate a response, the peptide or protein can be provided as an implant, an oily injection, or as a particulate system. The particulate system can be a microparticle, a microcapsule, a microsphere, a nanocapsule, or similar particle. (see, e.g., Banga, supra).

Nucleic acid based therapy to induce the production of memory B cells or plasma cells is also disclosed herein. Such therapy would achieve its therapeutic effect by introduction of a therapeutically effective amount of a polynucleotide encoding the IL-21 into a subject to achieve expression of IL-21. Without being bound by theory, IL-21 expressed following treatment with a therapeutic polynucleotide induces differentiation of an immature B cell into memory B cells and/or plasma cells. Delivery of the therapeutic polynucleotide can be achieved using a recombinant expression vector such as a chimeric virus or a colloidal dispersion system, or targeted liposomes.

Various viral vectors which can be utilized for nucleic acid based therapy as taught herein include adenovirus or adenoassociated virus, herpes virus, vaccinia, or an RNA virus such as a retrovirus. In one embodiment, the retroviral vector is a derivative of a murine or avian retrovirus, or a human or primate lentivirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). In one embodiment, when the subject is a human, a vector such as the gibbon ape leukemia virus (GaLV) is utilized. A number of additional retroviral vectors can incorporate multiple genes. All of these vectors can transfer or incorporate a gene for a selectable marker so that transduced cells can be identified and generated. By inserting a nucleic acid encoding IL-21 into the viral vector, along with another gene which encodes the ligand for a receptor on a specific target cell, for example, the vector is now target specific. Retroviral vectors can be made target specific by attaching, for example, a sugar, a glycolipid, or a protein. In one specific, non-limiting example, targeting is accomplished by using an antibody to target the retroviral vector.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include, but are not limited to, Q2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for a polynucleotide encoding IL-21 is a colloidal dispersion system. Colloidal dispersion systems include macromolecule complexes, nanocapsules, microspheres, beads, and lipid-based systems including oil-in-water emulsions, micelles, mixed micelles, and liposomes. One colloidal dispersion system is a liposome. Liposomes are artificial membrane vesicles which are useful as delivery vehicles in vitro and in vivo. It has been shown that large unilamellar vesicles (LUV), which range in size from 0.2-4.0 microns, can encapsulate a substantial percentage of an aqueous buffer containing large macromolecules. RNA, DNA and intact virions can be encapsulated within the aqueous interior and be delivered to cells in a biologically active form (Fraley et al., *Trends Biochem. Sci.* 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the nucleic acid of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino et al., *Biotechniques* 6:682, 1988).

The composition of the liposome is usually a combination of phospholipids, particularly high-phase-transition-temperature phospholipids, usually in combination with steroids, especially cholesterol. Other phospholipids or other lipids can also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidyl-glycerols, where the lipid moiety contains from 14-18 carbon atoms, particularly from 16-18 carbon atoms, and is saturated. Illustrative phospholipids include, for example, phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system can be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

For administration to a subject, a therapeutically effective dose of a pharmaceutical composition containing nucleic acid encoding IL-21, an IL-21 polypeptide or an IL-21 agonist, can be included in a pharmaceutically acceptable carrier. Optionally, other agents can be included in the pharmaceutical composition. For example, an antigen can also be administered in conjunction with the nucleic acid encoding IL-21, IL-21 polypeptide, or IL-21 agonist, either simultaneously or sequentially. In another example, an additional cytokine can be included.

The pharmaceutical compositions are prepared and administered in dose units. Solid dose units are tablets, capsules and suppositories. For treatment of a patient, depending on activity of the compound, manner of administration, nature and severity of the disorder, age and body weight of the patient, different daily doses are necessary. Under certain circumstances, however, higher or lower daily doses can be appropriate. The administration of the daily dose can be carried out both by single administration in the form of an individual dose unit or else several smaller dose units and also by multiple administrations of subdivided doses at specific intervals.

The pharmaceutical compositions are in general administered topically, intravenously, subcutaneously, intramuscularly, orally or parenterally or as implants, but even rectal use is possible in principle. Suitable solid or liquid pharmaceutical preparation forms are, for example, granules, powders, tablets, coated tablets, (micro)capsules, suppositories, syrups, emulsions, suspensions, creams, aerosols, drops or injectable solution in ampoule form and also preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of present methods for drug delivery, see Langer, *Science* 249:1527-1533, 1990.

A therapeutically effective dose of a pharmaceutical composition containing nucleic acid encoding IL-21, or an IL-21 polypeptide, can be delivered locally or systemically. A therapeutically effective dose is the quantity of an IL-21, or a nucleic acid encoding an IL-21, that cures or at least partially arrests the symptoms of the deficiency of memory B cells or plasma cells. Amounts effective for this use will, of course, depend on the severity of the disease and the weight and general state of the patient. Typically, dosages used in vitro can provide useful guidance in the amounts useful for in situ administration of the pharmaceutical composition, and animal models can be used to determine effective dosages for treatment of particular disorders. Various considerations are described, e.g., in Gilman et al., eds., *Goodman And Gilman's: The Pharmacological Bases of Therapeutics,* 8th ed., Pergamon Press, 1990; and *Remington's Pharmaceutical Sciences,* 17th ed., Mack Publishing Co., Easton, Pa., 1990, each of which is herein incorporated by reference.

Screening

A method is disclosed herein for identifying an agent with a physiological effect on differentiation of a memory B cells and/or a plasma cell. The method includes contacting a population of cells including B cell progenitors, such as substantially purified immature B cells, naïve B cells or memory cells with an effective amount of IL-21 and an agent of interest, and determining the effect of the agent on memory B cell and/or plasma cell differentiation. For example, the effect on differentiation of plasma cells can be evaluated by measuring antibody production, or by detecting one or more markers that characterize plasma cells. Similarly, the effect on production of memory cells can be evaluated using one or more markers that characterize memory cells. In one embodiment, the agent inhibits the differentiation of the memory B cell and/or the plasma cell as compared to a control. In another embodiment, the agent stimulates the differentiation of the memory B cells/and or the plasma cell as compared to a control.

Suitable controls include populations of cells not contacted with IL-21 and not contacted with the agent, cells contacted with IL-21 in the absence of the agent, or a standard value. Agents identified by the assay can be selected for further study if, for example, they show a statistically different result from a control. For example, a student's T-test is used to compare the values obtained in the assay with the control values. A statistically significant result is then considered to be one in which $p<0.05$.

The agent can be any agent of interest. In one embodiment, therapeutic agents that are derived from combinatorial chemical libraries, are screened in high throughput assays. Agents identified from the library are further characterized and/or detected using appropriate methods.

In the event that the agent is a nucleic acid, any of a variety of procedures can be used to further characterize the nucleic acid (such as a gene of interest). For example, nucleic acid agents identified from the library are further evaluated, detected, cloned, sequenced, and the like, either in solution or after binding to a solid support, by any method usually applied to the detection of a specific DNA sequence, such as PCR, oligomer restriction (Saiki et al., *Biol. Technology* 3:1008-1012, 1985), allele-specific oligonucleotide (ASO) probe analysis (Conner et al., *Proc. Natl. Acad. Sci. USA* 80:278, 1983), oligonucleotide ligation assays (OLAs) (Landegren et al., *Science* 241:1077, 1988), and the like. In addition, any of a variety of procedures can be used to clone genes of interest when the test composition is expressed as a gene product in a combinatorial library (as opposed to a chemical composition). One such method entails analyzing a shuttle vector library of DNA inserts (derived from a cell which expresses the composition) for the presence of an insert which contains the gene. For example, cells are transfected with the vector, and then assayed for expression of the product of interest. The preferred method for cloning these genes entails determining the amino acid sequence of the composition protein, for example by purifying the desired protein and analyzing it with automated sequencers.

The proteins can be extracted and purified from the culture media or a cell by using known protein purification techniques, such as extraction, precipitation, ion exchange chromatography, affinity chromatography, gel filtration and the like. The therapeutic proteins can be isolated by affinity chromatography.

A method is also disclosed herein for identifying an agent that inhibits an activity of IL-21. The method includes contacting a cell with an agent and determining if the agent inhibits Bcl-6, Blimp-1 and/or AID. The identification of an agent as inhibiting Bcl-6, Blimp-1 and/or AID identifies the agent being of use to inhibit the activity of IL-21. In one embodiment, the agent inhibits one or more of Bcl-6, Blimp-1 and AID as compared to a control. Suitable controls are cells not contacted with the agent, such as cells contacted with an agent that is known not to be an IL-21 receptor antagonist, or a cell contacted with a buffer in the absence of a test agent. Suitable controls also include untreated cells or a standard value.

Bcl-6 is described in U.S. Pat. No. 6,174,997, herein incorporated by reference. In one embodiment, the agent is an antisense molecule that specifically binds Bcl-6. Exemplary antisense molecules are described, for example, in U.S. Pat. No. 6,140,125. The agent can also be an antibody that specifically binds Bcl-6. Exemplary antibodies are described in U.S. Pat. No. 5,882,858.

Blimp-1 is described in U.S. Pat. No. 6,586,579, herein incorporated by reference. In one embodiment, the agent is an antisense molecule that specifically binds a nucleic acid encoding Blimp-1, or an antibody that specifically binds Blimp-1 protein. Thus, as disclosed herein, these antisense agents or antibodies can be used to inhibit an activity of IL-21. Similarly, antisense molecules that bind specifically to a nucleic acid encoding AID, or an antibody that specifically binds AID protein can be utilized to inhibit an activity of IL-21.

As discussed above, the agent can be any agent of interest. The agent can be a chemical compound, nucleic acid, antibody, or any small molecule that affects transcription of Bcl-6, Blimp-1 and/or AID, or affects an activity of Bcl-6 polypeptide, or Blimp-1 polypeptide and/or AID polypeptide. As described above, upon detection an agent can be further characterized by suitable methods.

Methods of detecting the inhibition of Blimp-1 or Bcl-6 expression and/or are known in the art. For example, the expression of Blimp-1 or Bcl-6 can be analyzed by detecting the presence of mRNA encoding Blimp-1 or Bcl-6. For example, Blimp-1 expression can be evaluated by detecting an RNA encoding Blimp-1 exemplified by the sequences represented by GENBANK® Accession Nos. U08185 or AF084199, or a homolog thereof. Bcl-6 expression can be evaluated by detecting an RNA encoding Bcl-6 exemplified by the sequences represented by GENBANK® Accession Nos. NM009744 or U00115, or a homolog thereof. Similarly, AID expression can be evaluated by detecting an RNA encoding AID, exemplified by sequences represented by GENBANK® Accession Nos. ABA40430 and ABA40431. One of skill in the art can readily measure the presence of a specific mRNA, using techniques such as, but not limited to Northern blot, Dot blots, reverse transcriptase polymerase chain reaction (RT-PCR), or real-time PCR. The expression of Blimp-1 or Bcl-6 can also be analyzed by detecting the presence of Blimp-1 or Bcl-6 proteins. Exemplary Blimp-1 proteins that can be detected include those represented by GENBANK® Accession Nos. AAA19252, AAC33300, and homologs thereof. Exemplary Bcl-6 proteins that can be detected include those represented by GENBANK® Accession Nos. AAB17432, AAC50054, and homologs thereof. For example, assays such as immunohistochemical assays, radioimmune assays, or ELISA assays can be used to detect Blimp-1 or Bcl-6 proteins.

An activity of Blimp-1 or Bcl-6 can also be measured. For example, Blimp-1 or Bcl-6 DNA binding activity can be measured using assays known to those of skill in the art, such as, but not limited to, electrophoretic mobility shift assays. If an agent decreases the amount of Bcl-6 or Blimp-1 mRNA, decreases the amount of Bcl-6 or Blimp-1 protein, or decreases the activity of Blimp-1 or Bcl-6 as compared to a control, then the agent is of use in inhibiting an activity of IL-21. One of skill in the art can readily determine a significant decrease in these parameters, such as a 25%, a 50%, a 75%, 80%, 85%, 90%, 95%, or 99% decrease, using standard statistical methods. Similarly, a decrease in the expression or activity of AID can also be measured by those of skill in the art.

Hybridoma Technology

Although numerous protocols, reagents and fusion partners are available for producing mouse B cell hybridomas, there are very limited resources available for producing monoclonal antibodies from human B cells. For example, there are relatively few human B cell fusion partners (e.g., LICR-2 (HMY2), HK-128, and SPAZ-4 cells), which can be successfully fused to non-transformed B cells, although these fusion partners can be fused to EBV-transformed or malignant human B cells. In addition, human B cells have been differentiated into plasma cells and plasma blasts, especially of known specificity, only with low efficiency. Mitogens such as pokeweed mitogen or PMA have been used to activate human B cells in the presence of various cytokine cocktails in attempts to generate stimulated human B cells that will fuse but this has met with limited success. Activated T cells have also been used in attempts to generate B cell hybridomas (Bergman et al., *J Immunology* 156:3118-3132, 1996).

IL-21 not only induces human B cells to intensely proliferate (which is required for successful fusion of hybridomas) but also induce the differentiation of human naïve and memory B cells into antibody-producing plasma cells. Thus, IL-21 can be used to activate B cells (e.g., in combination with anti-CD40 and/or anti-IgM and anti-CD40) to generate B cells that will successfully fuse with the available fusion partners. For example, naïve human B cells can be primed in vitro. Alternatively, naïve human B cells can be transferred into NOD/SCID mice, which are then immunized in the presence of soluble T cell co-stimulators, followed by in vitro co-activation with IL-21, and optionally with additional stimulatory agents, such as anti-CD40 and/or anti-IgM. Following in vitro or in vivo priming, the human b cells can be fused with partners, such as those selected form the cell lines listed above, to generate human B cell hybridomas of known specificities. In addition, screening of libraries of hybridomas produced by fusing memory B cells co-activated with IL-21

(and optionally with anti-CD40) can be used to identify human B cell hybridomas of know specificities.

EXAMPLES

The disclosure is illustrated by the following non-limiting Examples.

Example 1

Materials and Methods

Mouse Splenic B cell preparation and proliferation assays. C57BL/6 mice were obtained from Jackson Laboratory and (C57BL/6×129) F1 mice were generated at NIH. Splenic B cells were isolated using B220- or CD43-magnetic beads (Miltenyi) and were >95% pure as assessed by flow cytometry using B220-PE and TCRβ-APC. B cells isolated from $\gamma_c$ KO mice (which have diminished B cell numbers), were approximately 90% pure. B cells were plated in 96 well plates at $10^5$ cells/well and were treated as indicated with LPS (5 µg/ml, Sigma), anti-CD40 (1 µg/ml, BD PharMingen), anti-IgM (5 µg or 2.5 µg/ml; Sigma or Jackson Immunolaboratory), murine IL-4 (200 U/ml), and murine IL-21 (50 ng/ml). For proliferation assays, cells were cultured for either two or four days and pulsed with $^3$H-thymidine (1 µCi/well) for the last 18 hours of culture.

Isolation of human B cells. Human peripheral B cells were isolated from buffy coats of anonymous healthy donors drawn at the National Institutes of Health Division of Transfusion Medicine. Umbilical cord blood samples were obtained from Advanced Bioscience Resources, Inc. (Alameda, Calif.). Generally, human cord blood and peripheral B cells were isolated by negative selection using the Rosette-sep technique following the manufacturer's instructions (Stem Cell Technology, Vancouver, British Columbia). Preparations were typically >96% $CD19^+$ from peripheral blood. Negatively-selected cord blood B cell isolations yielded more heterogeneous cell populations. Therefore, B cells were positively-selected with anti-CD19 magnetic beads (Miltenyi Biotech, Auburn, Calif.) in some of the cord blood experiments and these were typically >95% pure. For further purity of peripheral B cells, $CD20^+$ $CD27^-$ naïve B cells or $CD20^+CD27^+$ memory B cells were isolated on a MoFlo cell sorter, (Dako Cytomation, Carpinteria, Calif.). Briefly, negatively-selected B cells were incubated at $10^7$ cells/ml in staining buffer with mAbs specific for CD20 and CD27 and in some experiments anti-IgD as well. Cells were incubated for 30 min at 4° C., washed and sorted into $CD20^+$ $CD27^+$ or $CD20^+CD27^-$ subsets. Preparations were typically >98% pure.

Human B cell culture, activation and CFSE labeling. Purified B cells were cultured at $1\times10^6$ cells/ml in either 1 ml in 24 well culture plates or 100 µl in 96 well round bottom culture plates. The cells were incubated with a combination of human IL-2 (100 U/ml, Roche, Indianapolis, Ind.), human IL-4 (100 ng/ml, R&D systems, Minneapolis, Minn.), human IL-21 (100 ng/ml, R&D systems), human IL-10 (25 ng/ml, R&D systems) and either 1 µg/ml anti-human CD40 (R&D systems), 5 µg/ml anti-IgM (Jackson ImmunoResearch Laboratories, (West Grove, Pa.), or 0.01% final dilution of heat killed, formalin-fixed SAC (Calbiochem, La Jolla, Calif.). In some experiments, purified B cells were labeled with CFSE. In brief, purified B cells were washed extensively in PBS to remove all FCS, and CFSE/PBS (Molecular Probes, Eugene, Oreg.) was added at a final concentration of 2.5 µM to 2-5× $10^7$ cells/ml for 8 minutes. Labeling was quenched by addition of FCS, and cells were washed four times in medium containing 10% FCS before culture. To obtain an accurate comparison for the controls, cord blood B cells were stimulated in the presence of IL-4 which facilitated cell survival but induced neither IgD down-modulation or plasma cell differentiation.

Human B cell proliferation assays. To assess proliferative responses of cultured cells, $10^5$ purified B cells were cultured as described above in 96 well round bottom plates. After 3-5 days of culture, $^3$[H]-thymidine (37 Kbq/well) was added to the cultures for an additional 16 hours. Thymidine uptake was measured using a liquid scintillation counter.

Western blotting. Clarified whole cell lysates were subjected to SDS-PAGE and Western blotting using anti-PARP (Cell Signaling Technology, MA). For Blimp-1, whole cell extracts (20 µg) were fractionated on 8% SDS-gels (Invitrogen) and transferred to Immobilon P membranes (Millipore). After blocking in 5% milk/TBST, blots were incubated overnight in rabbit anti-Blimp-1, washed, and incubated in HRP-labeled goat anti-rabbit IgG. Blots were development with an enhanced chemiluminescent substrate (Amersham).

Staining for apoptotic cells. Apoptosis was assessed using annexin-V and 7-AAD (BD PharMingen, CA) and the TUNEL staining reagent (Roche Applied Science, IN). Staining was performed according to the manufacturer's instructions.

Transgenic and knockout mice. Murine or human IL-21 cDNA constructs containing V5 and His tags were generated by PCR and inserted into pHSE, a plasmid in which the expressed cDNA is under the control of the H-2$k^b$ promoter and IgM enhancer (Pircher, *EMBO J.* 8:719-727, 1989; Held, *J. Exp. Med.* 184:2037-2041, 1996). The plasmid was linearized with XhoI, DNA purified, and 2 ng was microinjected into the pronuclei of fertilized oocytes from superovulated female C57BL/6×CBA F1/J mice and two days later implanted into the oviducts of pseudopregnant foster mothers. The founders were interbred with wild-type littermates. IL-21R$^{-/-}$ mice were generated as previously described (Ozaki et al. *Science* 298:1630-1634, 2002).

In vivo transient expression of IL-21. The murine IL-21 cDNA was subcloned into the pORF expression vector (InvivoGen, San Diego, Calif.), and 20 µg of DNA in 2 ml saline was injected intravenously into C57BL/6 mice within 5 seconds (hydrodynamics-based transfection) (Liu et al., *Gene Therapy* 6:1258-1266, 1999; Zhang et al., *Human Gene Therapy* 10:1735-1737, 1999). At days 4 and 7, the mice were analyzed with either saline or pORF-injected mice as control.

Flow cytometric analysis of mouse B cell populations. Cell populations were stained with the following commercially obtained antibodies: FITC anti-CD21, CD23 and IgM, PE anti-CD23 and IgD, APC anti-B220 (BD Pharmingen). Staining with and AA4.1 antibodies was revealed with either PE- or Cy-conjugated streptavidin (BD Pharmingen). Analyses were conducted using a FACSCaliber flow cytometer and data was analyzed using CellQuest software (BD Immunosystems).

Flow Cytometric analysis of human B cell populations. Four color flow cytometry was performed using a FACSCalibur (Becton Dickinson, Calif.). Briefly, supernatants were collected and then all cells were harvested from 96 well cultures at the end of the incubation period and stained for 30 minutes on ice with a combination of mAb obtained from BD Biosciences (Palo Alto, Calif.). The combination of anti-IgD-FITC, CD27-PE, anti-CD19-PerCP-Cy5.5 and anti-CD38-APC (clone HB7) was routinely used. Viable cells were identified by gating on lymphocytes and cells were analyzed immediately. All samples were collected for 1 minutes, and as a result the density of the dot plots reveals relative cell numbers. In some experiments, to obtain total B cell numbers more accurately, AccuCount Particles (Spherotech, Libertyville, Ill.) were added before analyzing samples by flow cytometry and total cell numbers was determined as per manufacture's instructions. In some experiments, the combination of CFSE, anti-IgD-PE, anti-CD19 PerCP-Cy5.5, and anti-CD38-APC was used.

Determination of human Ig Levels. Secreted Ig in the culture supernatant of human B cells was quantitated by ELISA. Briefly, 96-well flat-bottom Nunc-Brand Immuno plates (Nalge Nunc International, Rochester, N.Y.) were coated with 5 μg/mL of either affinity purified goat anti-human IgM or goat anti-human IgG-Fc (Bethyl Laboratories, Montgomery, Tex.) overnight at 4° C. Wells were then washed and blocked with a 0.2% BSA/PBS, and then the culture supernatant were titered onto the treated plates and incubated overnight at 4° C. Bound Ig was detected with 0.5 μg/ml alkaline phosphatase conjugated goat anti-human IgM or IgG (Bethyl Laboratories) and developed with p-nitrophenyl phosphate tablets (Sigma-Aldrich Inc, St. Louis, Mo.). Specific absorbance was measured and optical density quantified at 410 nM by a Powerwave X 96-well plate reader (Bio-tek Instruments, Inc, Winooski, Vt.). IgE concentrations were measured with the Human IgE ELISA kit (Bethyl Laboratories). Specific IgG isotypes were differentiated using the Human IgG Subclass Profile ELISA KIT (Zymed Laboratories, Inc., San Francisco, Calif.).

Immunohistochemical staining of lymphoid follicles. Mouse spleens were removed and subdivided for analysis by either immunohistology or flow cytometry. For immunohistology, tissues were embedded in Tissue-Tek/O.C.T. compound (Sakura, Zoeterwoude, the Netherlands), frozen in liquid nitrogen, and serially sectioned. Frozen tissue sections were immediately fixed in ice-cold acetone for 5 minutes and stained for 45 minutes in a humid chamber with either biotinylated MAdCAM-1 (Southern Biotech), rat antibody supernatant specific for IgD (clone 1126C), or purified rat antibody specific for MCA 1849 (MARCO, Serotec, Raleigh, N.C.). The sections were washed and bound antibodies were revealed with either SA-conjugated or goat anti-rat conjugated Oregon Green (Molecular Probes, Eugene, Oreg.). IgM was detected with directly conjugated goat anti-mouse IgM Texas Red (Southern Biotechnology).

Electrophoretic Mobility Shift Assays. Nuclear extracts were prepared from splenic B cells cultured with anti-IgM±IL-21 for 24 hours. Five μg were used for DNA binding reactions with either a Blimp-1 binding site (MHC2TA) from the class II MHC promoter (Piskurich et al., Nature Immunol. 1:526-532, 2000) or with a Bcl-6 consensus binding site (Relijc et al., J. Exp. Med. 192:1841-1847, 2000). The double stranded oligonucleotides were as follows (only top strand is shown):

```
MHC2TA
5'-CAGTCCACAGTAAGGAAGTGAAATTAATTT-3' (SEQ ID NO: 3)

Bcl-6
5'-GAAAATTCCTAGAAAGCATA-3'         (SEQ ID NO: 4)
```

Real time PCR. Blimp-1, Bcl-6 and Pax5 mRNA levels in murine B cell populations were quantitated relative to GAPDH RNA levels by real time PCR. RNA was reverse transcribed using an Omniscript kit (Qiagen) according to the manufacturer's directions and PCR was performed using a Quantitect Probe Detection system (Qiagen). The oligonucleotides used for this study were:

```
Blimp-1
                                         (SEQ ID NO: 5)
FW 5'-ACAGAGGCCGAGTTTGAAGAGA-3'

(SEQ ID NO: 6)
RV 5'-AAGGATGCCTCGGCTTGAA-3'

(SEQ ID NO: 7)
TP 5'-[6-FAM]CCCTGGGATTCCGGCGCTG[TAMRA-6-FAM]-3'

PAX5
                                         (SEQ ID NO: 8)
FW 5'-AAACGCAAGAGGGATGAAGGT-3'

(SEQ ID NO: 9)
RV 5'-AACAGGTCTCCCCGCATCT-3'

(SEQ ID NO: 10)
TP 5'-[6-FAM]CACTTCCGGGCCGGGACTTCC[TAMRA-6-FAM]-3'

Bcl-6
                                         (SEQ ID NO: 11)
FW 5'-TCAGAGTATTCGGATTCTAGCTGTGA-3'

(SEQ ID NO: 12)
RV 5'-TGCAGCGTGTGCCTCTTG-3'

(SEQ ID NO: 13)
TP 5'-[6-FAM]TGCAACGAATGTGACTGCCGTTTCTCT[TAMRA-6-
FAM]-3'

GAPDH
                                         (SEQ ID NO 14)
FW 5'-TTCACCACCATGGAGAAGGC-3'

(SEQ ID NO: 15)
RV 5'-GGCATGGACTGTGGTCATGA-3'

(SEQ ID NO: 16)
TP 5'-[6-FAM]TGCATCCTGCACCACCAACTGCTTAG[TAMRA-6-
FAM]-3'
```

Blimp-1, Bcl6, AICDA, PAX-5 and β-2 microglobulin mRNA levels were evaluated by real time PCR in negatively or positively purified human B cells. After 3 days in culture, cells were harvested and resuspended in TRIzol (Invitrogen, Carlsbad, Calif.) and stored at −70° C. RNA was isolated using the RNeasy mini kit (Qiagen, Valencia, Calif.). Purity was measured using spectrophotometry. Reverse transcription reactions were prepared using the Superscipt One-Step PCR System with Platinum Taq Polymerase® and ROX reference dye (Invitrogen). 50 ng isolated RNA was added per reaction with 1.2 mM MgSO$_4$. Taqman Assays-on Demand Gene expression primer/probe sets (Applied Biosystems) were used for Blimp-1 (Hs00153357_m1), BC16 (Hs00153368_m1), AICDA (Hs00221068_m1), PAX-5 (Hs00277134_m1) and β-2 microglobulin (β-2M) (Hs99999907_m1). Final concentrations were 1.8 KM for primers and 0.5 μM for probes. RT PCR was performed using the ABI Prism® 7700 Sequence Detection System and cycle conditions and relative quantification were completed as described by manufacturers' instructions (Applied Bio Sysytems, Foster City, Calif.). Expression of each transcription factor was calculated using the Comparative CT method with efficiency calculations and with all mRNA levels normalized to β-2M. All reported values were then further normalized to control conditions, usually IL-2 or IL-2 and IL-4 (without any stimuli) as a value of 1.

Somatic Hypermutation: Human cord blood B cells were stimulated with IL-2 and IL-21 in the presence of anti-CD40 with or without anti-IgM for 7-12 days. Individual live CD19$^+$, IgD$^-$ CD38$^+$ class-switched B cells and IgD$^-$ CD38$^{hi}$ plasma cells were sorted and the rearranged Ig heavy chain V regions ($V_H$) from genomic DNA of single cells was amplified and directly sequenced as previously described (Sims et al., *Blood*, in press, 2005). The $V_H$ gene sequence was compared to the closest germline gene and the number of mismatches was determined. The frequency of mismatches for stimulated cord blood B cells was compared with purified cord blood B cells that were analyzed before culture.

Example 2

Induction of Apoptosis

Consistent with a pro-apoptotic effect, IL-21-induced DNA fragmentation as determined by TUNEL staining of B220+ B cells stimulated with anti-CD40 (FIG. 1A, panels ii versus i), anti-IgM+IL-4 (panels iv versus iii), or LPS (panels vi versus v). Interestingly, IL-21 could induce apoptosis of anti-CD40 stimulated B cells, even though it augmented ³H-thymidine incorporation in these cells.

IL-21 induced apoptosis can be inhibited by caspase inhibitors (Mehta et al., *J. Immunol.* 170:4111-18, 2003) and correspondingly, IL-21 induced cleavage of PARP, a caspase substrate, either alone (FIG. 1B, panel i) or when combined with LPS (panel ii) or anti-CD40 (panel iii). Although Bcl-2 mRNA was observed to decrease after treatment with IL-21 (Mehta et al., *J. Immunol.* 170:4111-18, 2003), no change was observed in Bcl-2 protein levels (FIG. 1C). In addition to its pro-apoptotic effect on B cells stimulated with mitogens, IL-21 also induced apoptosis of freshly isolated naïve splenic B cells within three days of culture. Conversely, it did not diminish the number of CD3+ T cells, and in fact increased the survival of both CD4+ and CD8+ T cells, with a greater effect on CD8+ T cells (FIG. 1D).

The pro-apoptotic effects of IL-21 on B cells in vitro were surprising given that IL-21R expression is essential for normal Ig production in vivo (Ozaki et al., *Science* 298:1630, 2002). To help explain this apparent paradox, IL-21 transgenic (TG) mice were generated using a vector (Pircher et al., *EMBO J.* 8:719, 1989; Held et al., *J. Exp. Med.* 184:2037, 1996) that drives expression in T, B, and NK cells. Founder mice expressing murine IL-21 uniformly exhibited growth retardation and died before sexual maturity. Thus, TG mice expressing human IL-21 were generated. Human IL-21 can stimulate murine cells in vitro but is likely to bind the murine IL-21R with lower affinity. Four founders of the human IL-21 TG mice also exhibited growth retardation and died before adulthood, but three viable lines were obtained (FIG. 2A). The line with the greatest IL-21 expression was lost, consistent with toxicity resulting from high expression of IL-21. All studies were performed on the remaining lines (#5 and #7).

In the normal mouse spleen, approximately 90% of B cells are mature follicular (FO) or marginal zone (MZ) cells (Martin and Kearney, *Nat. Rev. Immunol.* 2:323, 2002). Immature or newly formed (NF) B cells are produced in the bone marrow and migrate to the spleen as transitional T1 cells where they mature into T2 cells. Only 1-3% of these cells differentiate into mature B cells (Hao and Rajewsky, *J. Exp. Med.* 194:1151, 2001; Loder et al., *J. Exp. Med.* 190:75, 1999), which can develop into memory B cells and antibody forming plasma cells after antigen stimulation (Sze et al., *J. Exp. Med.* 192:813, 2000; Calame, *Nat. Immunol.* 2:1103, 2001). Staining of splenocytes from the human IL-21 transgenic mice with antibodies to IgM and CD21 (marked as "M" in FIG. 2B, panel i) and T2/MZ B cell populations were decreased, whereas T1 cells appeared to be intact or increased (FIG. 2B, panel ii versus i). Consistent with this, the percentage of $CD21^{int}CD23^{high}$ "mature" follicular (FO) B cells (FIG. 2B, panel iii) was markedly decreased in transgenic mice (panel iv), while "immature" newly formed (NF) $CD21^{low}CD23^{low}$ B cells (panel iii) were dramatically increased in the transgenic mice (panel iv), suggesting either augmented production or decreased death of these cells or a block in their differentiation to mature B cells. Similarly, an apparent increase in immature B cells (compare FIG. 2C to 2B, panel ii versus i and iv versus iii) was observed in mice injected with IL-21 DNA using hydrodynamic-based transfection (Liu et al., *Gene Ther.* 6:1258, 1999; Zhang et al., *Human Gene Ther.* 10:1735, 1999). IL-21 expression vector DNA was injected into wild type mice allowing examination of the effect of a relatively acute increase in murine IL-21 in wild type mice, again finding Consistent with this increase in "immature" B cells, staining with AA4.1 mAb, which binds to a 130-140 kDa marker of immature B cells (Allman et al., *J. Immunol.* 167:6834, 2001), also was increased in IL-21 transgenic mice (FIG. 3A, panel ii versus i) and mice injected with IL-21 DNA. Analysis of immature and mature populations as defined by AA4.1/B220 staining revealed an increase in the T1:T2 transitional cell ratio (i.e., $CD23^{low}$:$CD23^{high}$ ratio) in the $AA41^{high}B220^+$ cells in the transgenic mice (panel iv versus iii) and mice injected with IL-21 DNA. However, the mature $AA4.1^{low}B220^+$ cells showed a decrease in the relative number of $CD23^{high}$ cells as well as a corresponding increase in $CD23^{low}$ cells (panel vi versus v), which was inconsistent with the conclusions of changes in FO and MZ B cells based on CD21/IgM and CD21/CD23 staining in FIGS. 2B and 2C. IL-21 potently decreased CD23 expression on naïve B cells and also on B cells stimulated with LPS or anti-CD40 (FIG. 3B), and modestly diminished expression of CD21. Thus, the apparent decrease in FO cells induced by IL-21 (FIGS. 2B and 2C, panels iii and iv) could have at least in part reflected an IL-21-mediated decrease in expression of CD23.

Figure 3:
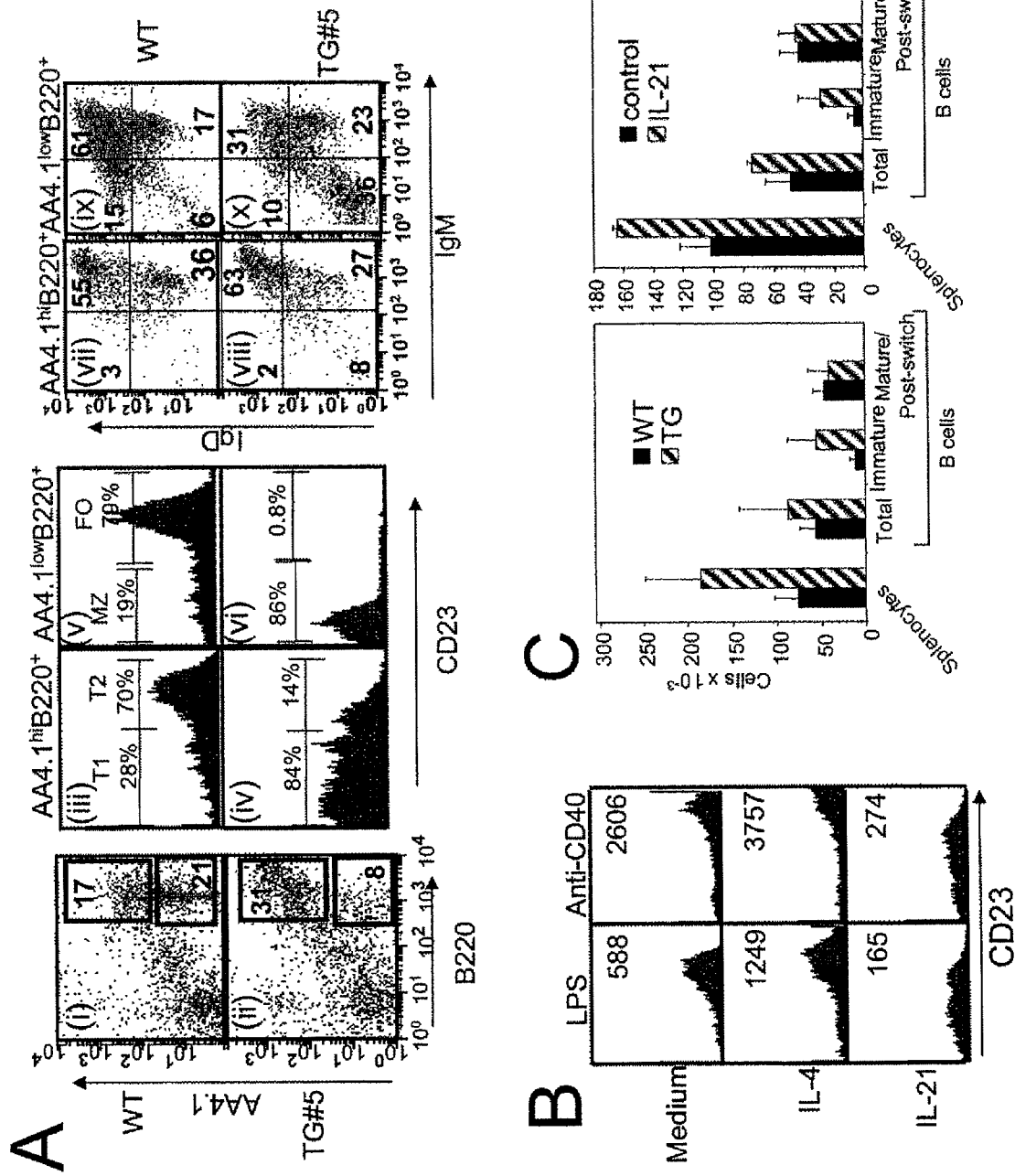
FIGS. 3A-C are sets of FACS plots and bar graphs demonstrating the effect of IL-21 on B cell populations.

Thus, surface expression of IgM and IgD was evaluated. These are not affected by IL-21. Among the $AA4.1^{high}$ immature cells, the IgM/IgD staining pattern revealed that the T1:T2 ($IgM^+IgD^{low}$:$IgM^{high}IgD^+$) ratio was not increased, and was, if anything, somewhat decreased (FIG. 3A, panel viii versus vii). The $AA4.1^{low}$ splenic population exhibited a modest decrease in the more mature FO B cell subset ($IgD^{high}IgM^{low}$) in both IL-21 TG mice (FIG. 3A, panel x versus ix, upper left quadrant) and mice injected with IL-21 DNA.

In contrast to the CD21/CD23 result, the changes in $IgD^{low}IgM^{high}$ MZ cells in either the TG (lower right quadrant) or the injected mice were modest. Interestingly, in both IL-21 TG mice (lower left quadrant) and IL-21-injected mice, there was a dramatic increase in the $IgD^{low}IgM^{low}$ population of $AA4.1^{low}$ splenocytes, which represents cells that have undergone Ig class switch recombination. Overall, based on the AA4.1 and IgM/IgD staining, IL-21 increased the total number of splenocytes and total B cells, with a marked increase in the number of immature $AA4.1^{high}$ B cells (FIG. 3C). $AA4.1^{low}$ cells, which include both mature B cells and post-switch cells, were normal in number (FIG. 3C). However, of these cells, mature B cells were diminished based on the decrease in IgD+ cells in FIG. 3A (panel x versus ix, see upper right quadrant), whereas post-switch cells (IgD−) were markedly increased (FIG. 3A, panel x versus ix, lower left quadrant). Thus, IL-21 stimulation decreases the number of mature B cells, but increases immature cells and drives the differentiation of post-switch cells.

Example 3

Effect of IL-21 on Splenic Architecture

Figure 4:
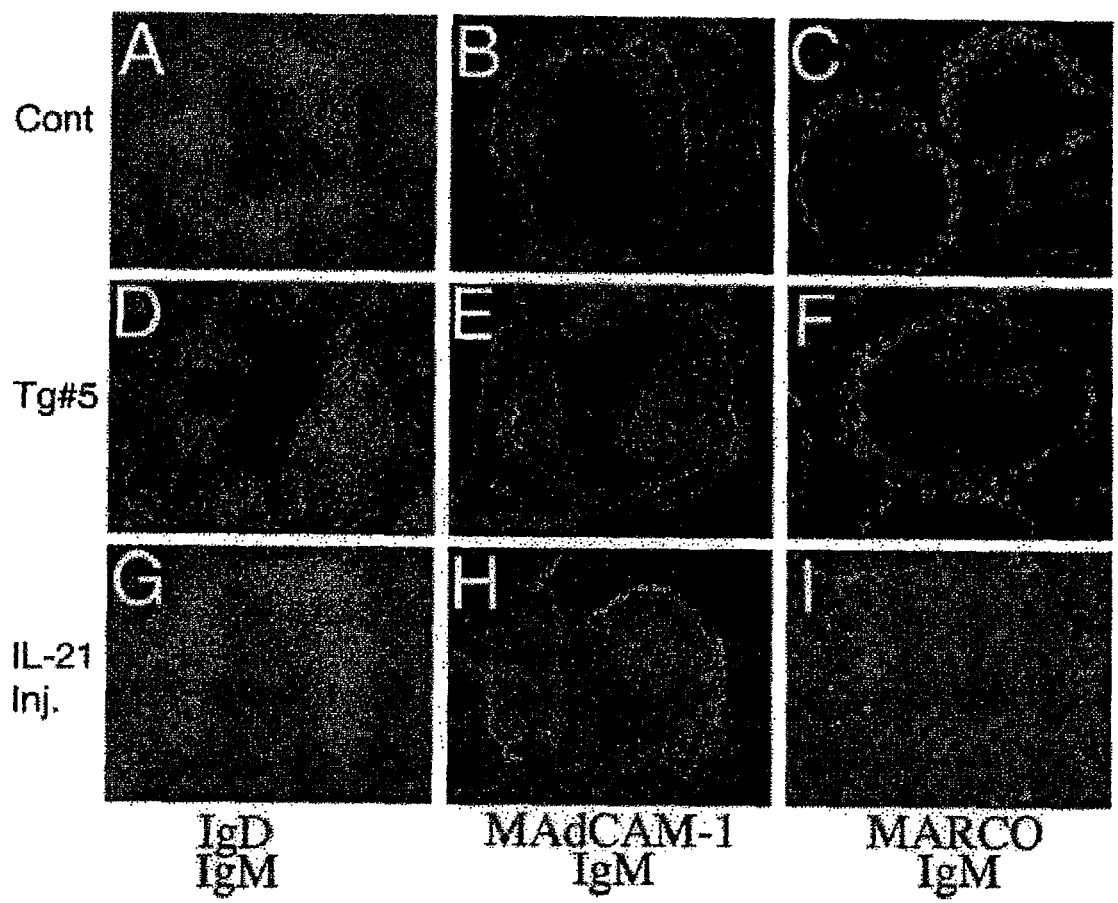
FIGS. 4A-I are a digital images of photomicrographs. Immunohistochemistry was performed on wild type control (A, B, C), Transgenic (D, E, F), and IL-21 plasmid injected (G, H, I) mice using antibodies to IgD/IgM (A, D, G), MAdCAM-1/IgM (B, E, H), and MARCO/IgM (C, F, I). Spleens were embedded in tissue-tek/O.C.T. compound (Sakura, Zoeterwoude, the Netherlands), frozen in liquid nitrogen, serially sectioned, fixed in ice-cold acetone for 5 minutes, and stained for 45 minutes in a humid chamber with either biotinylated anti-MAdCAM-1 (Southern Biotech), rat Ab supernatant specific for IgD (clone 1126C), or purified rat Ab specific for MCA 1849 (MARCO, Serotec, Raleigh, N.C.), followed by SA-conjugated or goat anti-rat conjugated Oregon Green (Molecular Probes, Eugene, Oreg.). IgM was detected with goat anti-mouse IgM Texas Red (Southern Biotechnology). Data are representative of several mice examined.

The effect of IL-21 on splenic follicular architecture was evaluated. Immunostaining with antibodies to IgM, IgD, MAdCAM-1, and MARCO showed that spleens from IL-21 transgenic mice had intact FO and MZ structures (FIGS. 4D-F versus FIGS. 4A-C). In contrast, spleens from mice injected with IL-21 DNA exhibited a loss of MZ B cells as revealed by the lack of a bright red ring of IgM$^{high}$IgD$^-$ B cells around the IgM$^+$IgD$^+$"green" follicles (FIG. 4G versus FIG. 4A). Nevertheless, the MAdCAM-1$^+$ marginal sinus (FIG. 4H versus FIG. 4B) and the MARCO$^+$ MZ macrophages (FIG. 4I versus FIG. 4C) were still present in these mice, indicating a loss of B cells from this region rather than a loss of the MZ structure. The follicular dendritic cell, CD4$^+$, and CD8$^+$ areas were normal in both IL-21 injected and transgenic mice. Thus, overall, the results revealed that chronic human IL-21 signaling in the TG mice did not affect the overall MZ structure, but led to increased immature B cells and accumulation of Ig class-switched B cells. Exposure to the more acute levels of murine IL-21 in the injected mice led to similar changes in splenic B cell populations, including that MZ B cells are retained as evaluated by CD1d and CD9, but these cells had apparently migrated out of the MZ (FIG. 4G versus FIG. 4A).

To evaluate the contribution of apoptosis to the effects of IL-21, annexin V staining was examined. Immunostaining with antibodies to IgM, IgD, MAdCAM-1, and MARCO showed that spleens from IL-21 transgenic mice had intact FO and MZ structures (FIGS. 4D-F versus FIGS. 4A-C). In contrast, spleens from mice injected with IL-21 DNA exhibited a loss of MZ B cells as revealed by the lack of a bright red ring of IgM$^{high}$IgD$^-$ B cells around the IgM$^+$IgD$^+$ "green" follicles (FIG. 4G versus FIG. 4A). Nevertheless, the MAdCAM-1$^+$ marginal sinus (FIG. 4H versus FIG. 4B) and the MARCO$^+$ MZ macrophages (FIG. 4I versus FIG. 4C) were still present in these mice, indicating a loss of B cells from this region rather than a loss of the MZ structure. The follicular dendritic cell, CD4$^+$, and CD8$^+$ areas were normal in both IL-21 injected and transgenic mice. Thus, overall, the results revealed that chronic human IL-21 signaling in the TG mice did not affect the overall MZ structure, but led to increased immature B cells and accumulation of Ig class-switched B cells. Exposure to the more acute levels of murine IL-21 in the injected mice led to similar changes in splenic B cell populations, including that MZ B cells are retained as evaluated by CD1d and CD9, but these cells had apparently migrated out of the MZ (FIG. 4G versus FIG. 4A).

Figure 5:
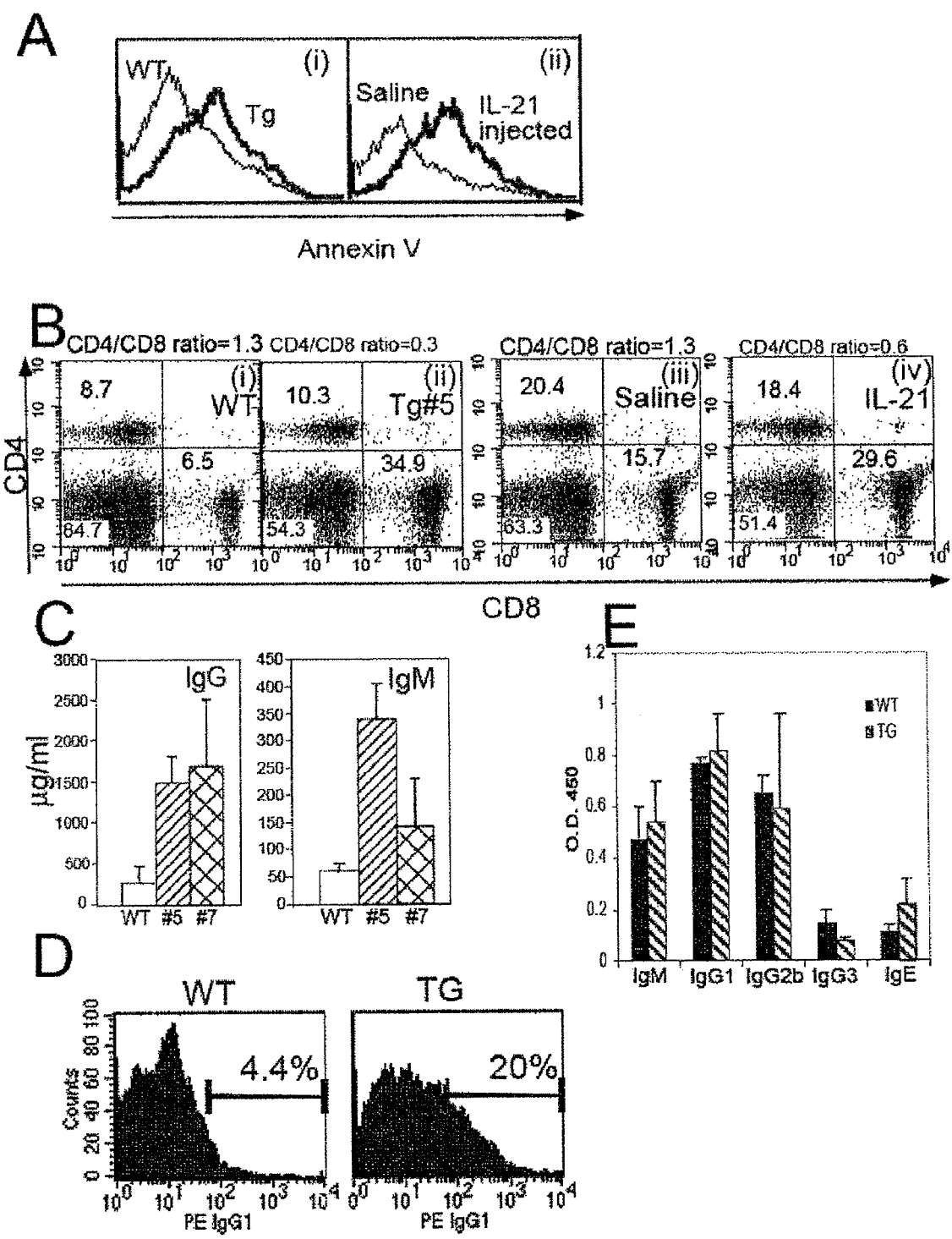
FIGS. 5A-E are graphs and digital images showing the effect of IL-21 on cell viability and Ig production in IL-21 TG mice.

To evaluate the contribution of apoptosis to the effects of IL-21, annexin V staining was examined. Higher annexin V staining of B220+B cells was seen in IL-21 TG mice than in WT littermates (FIG. 5A, panel i), and similarly, injection of mice with the IL-21 plasmid increased annexin V staining (FIG. 5A, panel ii). Thus, the reduction in mature FO B cells was, at least in part, caused by apoptotic death in vivo.

In contrast to the pro-apoptotic effect of IL-21 on mature B cells, IL-21 did not induce death of CD3$^+$ T cells, and in fact was potently anti-apoptotic for CD8$^+$ T cells (FIG. 1D). Consistent with this, IL-21 transgenic mice had a markedly decreased CD4/CD8 T cell ratio in thymus, spleen, and lymph nodes (FIG. 5B, panel ii versus i), resulting from a selective increase in CD8$^+$ T cells. Injection of the IL-21 plasmid in WT mice also decreased the CD4/CD8 splenic T cell ratio (FIG. 5B panel iv versus iii), with a marked increase in CD8$^+$ T cells at day 7 (approximately 41 million CD8$^+$ splenic T cells in IL-21 injected versus 13 million in the control). The ability of IL-21 to expand CD8$^+$ T cells in vivo could represent a redundant, rather than distinctive effect of IL-21, as IL-21R$^{-/-}$ mice do not exhibit an increased CD4/CD8 T cell ratio (Ozaki et al., *Science* 298:1630-1634, 2002), presumably because signaling in response to other $\gamma_c$-dependent cytokines that are important for CD8$^+$ T cell homeostasis, such as IL-7 and IL-15 (Schluns et al., *Nat Rev Immunol.* 3:269-279, 2003), is still intact. The data establish that IL-21 is a third $\gamma_c$-dependent cytokine that contributes to CD8$^+$ T cell homeostasis.

Although IL-21 increased B cell apoptosis in vivo, it also clearly induced an increase in Ig class-switched B cells (see above and FIG. 3A). Indeed, IL-21 TG mice had increased levels of serum IgG and IgM (FIG. 5C), and increased surface IgG1$^+$ B cells in the spleen (FIG. 5D). Moreover, mice injected with IL-21 DNA exhibited increased IgG$^+$ B cells by immunohistology. Thus, the effects of IL-21 on the primary antibody response to ovalbumin, a T cell dependent antigen, were analyzed. The concentrations of antigen-specific IgM and IgG were similar in WT and TG mice (FIG. 5E), demonstrating that "extra" IL-21 did not interfere with effective Ig production and thus was not apoptotic for the Ig producing cells. Thus, the data collectively indicate that IL-21 promotes maturation of B cells, accompanied by class switching and plasma cell formation.

Example 4

Effect of IL-21 on B Cell Maturation

To determine whether these maturation effects resulted from direct stimulation of B cells by IL-21, B cells cultured for 48 hours were analyzed in the presence of anti-IgM in combination with either IL-4, anti-CD40, or both stimuli (FIG. 6A) and IL-21. IL-21 stimulated B cell proliferation induced by anti-IgM, especially in the presence of anti-CD40, but it inhibited proliferation to anti-IgM plus IL-4 (FIG. 6A); however, costimulation of anti-IgM+IL-4-activated B cells with anti-CD40 restored the ability of IL-21 to augment proliferation (FIG. 6A). Consistent with the effect of IL-21 on antibody production (FIG. 5C), IL-21-induced expression of syndecan-1 (CD138), a plasma cell marker (FIG. 6B), and surface IgG1 (FIG. 6C) (see panels ii versus i and iv versus iii) in B cells stimulated with anti-IgM with or without IL-4. The surface IgG1$^+$ cells shown in FIG. 6C did not all express Syndecan-1, indicating that IL21 was increasing memory cells as well as plasma cells. Thus, culture conditions that allow IL-21 apoptotic effects also allow IL-21 induced B cell differentiation. Overall, IL-21 has pro-apoptotic effects for mature FO B cells, induces an increase in immature B cells, alters the B cell phenotype, and is a potent inducer of B cell maturation to memory B/post-switch cells and plasma cells. IL-21 also induces differentiation of human B cells into plasma cells and memory B cells.

Example 5

Blimp-1 and Bcl-6

As noted above, IL-21 is pro-apoptotic based on a caspase dependent mechanism, but its role related to B cell maturation and plasma cell differentiation was unclear. Blimp-1 is a transcription factor that has been identified as a master regulator of plasma cell differentiation (Turner et al., *Cell* 77:297-306, 1994), whereas Bcl-6 and Pax5 are required for germinal center formation (reviewed in Calame et al., *Annu. Rev.*

Immunol. 21:205-230, 2003). Interestingly, Blimp-1 and Bcl-6 have been shown to each inhibit expression of the other protein, and Blimp-1 additionally is an inhibitor of the expression of Pax5 (Shaffer et al., *Immunity* 17:51-62, 2002; Calame et al., *Annu. Rev. Immunol.* 21:205-230, 2003).

Figure 7:
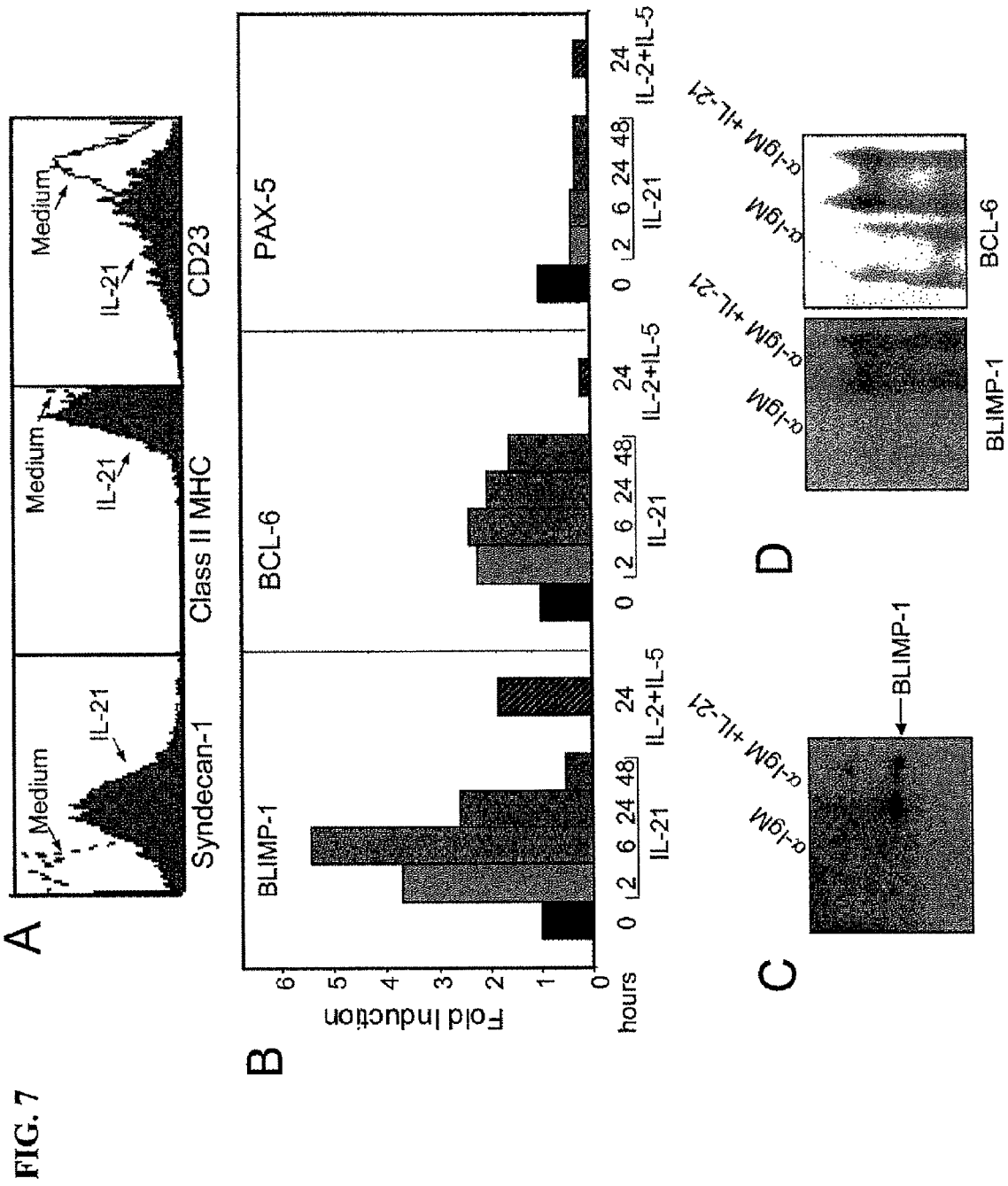
FIGS. 7A-D are graphs and digital images showing that IL-21 treatment increases Blimp-1 and Bcl-6 expression while diminishing Pax5.

Expression of these proteins was examined in Bcl-1 3B3 cells, a B cell lymphoma cell line in which treatment with IL-2 and IL-5 can induce plasmacytic differentiation into immunoglobulin-secreting cells (Messika et al., *J. Exp. Med.* 188: 515-525, 1998). The effect of IL-21 on these cells was examined, and it was found that IL-21 induced expression of syndecan-1, while it decreased expression of MHC class II, consistent with plasma cell differentiation and Blimp-1 induction (Turner et al., *Cell* 77:297-306, 1994; Piskurich et al., *Nature Immunol.* 1:526-532, 2000) (FIG. 7A). Consistent with the effect of IL21 on CD23 expression in splenic B cells (FIG. 3B), IL-21 also decreased CD23 expression in Bcl-1 cells (FIG. 7A).

Correlation of these findings with the expression of Blimp-1, Bcl-6 and Pax5 was sought. Based on real-time PCR analysis, IL-21 induced expression of mRNA for both Blimp-1 and Bcl-6, whereas it inhibited expression of Pax5 mRNA (FIG. 7B). The induction of Blimp-1 was at least as potent as that seen with the combination of IL-2 and IL-5; as expected, the combination of IL-2 and IL-5 inhibited expression of Bcl-6. The induction of both Blimp-1 and Bcl-6 was further confirmed by examining B cells purified from the spleen. Induction was not seen in cells treated with anti-IgM alone, but the addition of IL-21 induced Blimp-1 protein expression (FIG. 7C) as well as Blimp-1 and Bcl-6 DNA binding activity as evaluated by electrophoretic mobility shift assays (FIG. 7D).

IL-21 is the only type I cytokine that can induce apoptosis of resting naïve B cells, whereas other $\gamma_c$ family cytokines are typically anti-apoptotic. In the context of antigen activation, IL-2 can promote T cell death via a process known as activation-induced cell death (AICD) (Lenardo et al., *Annu. Rev. Immunol.* 17:221, 1999). However, IL-21 is different in that it is pro-apoptotic for B and NK cells instead of T cells (Kasaian et al., *Immunity* 16:559, 2002), and whereas AICD requires a prior activation signal, IL-21-induced apoptosis does not. In addition to apoptotic effects on mature B cells, IL-21 induced the accumulation of transitional B cells in the periphery. This could reflect homeostatic compensation for the reduction in peripheral mature B cells, the ability of IL-21 to promote maturation and/or survival of immature B cells from the bone marrow, and/or an ability of IL-21 to interfere with signals that promote differentiation from transitional to mature B cells. Strikingly, in mice injected with the IL-21 plasmid, the MZ was depleted of B cells, but the marginal sinus and associated MZ macrophages were left intact. It is possible that the MZ B cells migrated out of the MZ, as is found following exposure to particulate antigens such as bacteria (Martin et al., *Immunity* 14:617, 2001), where MZ B cells migrate to the T-B border, followed by the accumulation of Ag-specific plasmablasts in the red pulp. The extrafollicular foci of plasma cells are expanded in IL-21-treated mice and this might reflect this pattern of migration and differentiation. The MZ B cell population appeared intact in IL-21 TG mice.

IL-21 TG mice exhibited elevated serum IgM and IgG and had increased surface $IgG1^+$ B cells in the spleen, suggesting that IL-21 promoted Ig isotype switching in vivo. These mice could mount productive primary Ig responses (involving all isotypes) to a T cell dependent antigen. IL-21 downregulated CD23 expression on mature B cells and promoted differentiation to Ig secreting plasma cells both in vivo and in vitro, whereas IL-4 inhibits plasma cell differentiation (Knodel et al., *Eur. J. Immunol.* 31:1972-1980, 2001) and induces CD23 expression on mature B cells (Nelms et al., *Annu. Rev. Immunol* 17:701-738, 1999). Interestingly, accumulation of surface $IgG1^+$ cells in response to IL-21 is reduced in the presence of IL-4, whereas the induction of syndecan-$1^+$ cells was not altered. Thus, some but not all of the effects of IL-21 on the B cell immune response can be modulated by IL-4. The observation that IL-21 has anti-apoptotic effects on some myeloma cell lines (Brenne et al., *Blood* 99:3756, 2002) is consistent with the observations presented herein that IL-21 is an inducing factor for plasma cells. Its effect on plasma cell differentiation could result from induction of Blimp-1, whereas the induction of Bcl-6 is likely to be important for subsequent differentiation of germinal center cells into memory cells. It is noteworthy that IL-21 induced both Blimp-1 and Bcl-6, considering that these are usually mutually antagonistic (Shaffer et al., *Immunity* 17:51-62, 2002; Calame et al., *Annu Rev Immunol.* 21:205-230, 2003). This is another indication of the overall potency of IL-21 in stimulating various aspects of the differentiation of B cells, and having differential effects in a context-regulated manner.

IL-21 has pleiotropic effects on lymphoid lineages. Whereas IL21 is pro-apoptotic for mature B cells, and anti-apoptotic actions for T cells, IL-21 has complex actions for B cells, as demonstrated herein. The degree of IL-21-induced apoptosis depends on the nature of other signals to the B cell. Early in the B cell response, IL-21 can function as an apoptotic signal. When bystander B cells are stimulated in an antigen-non-specific manner by activated T cells mediated by CD40 engagement, but in the absence of B cell receptor signaling, IL-21 leads to apoptosis. Following the initiation of a B cell immune response, IL-21 can eliminate "bystander" B cells responsible for the non-specific hypergammaglobulinemia that is initially observed.

However, in B cells fully activated by B cell receptor signaling and an appropriate T cell signal (e.g., CD40L) (Lee et al., *Proc. Natl. Acad. Sci. USA* 96:9136-9141, 1999), IL-21 enhances Ig production, isotype switching, and memory cell and plasma cell production. In this regard it is demonstrated herein that IL-21 upregulates both Blimp-1 and Bcl-6. Moreover, it is unprecedented that both Blimp-1 and Bcl-6 would are induced. Thus, IL-21 is a major regulator of the B cell immune response. This finding explains how IL-21 can drive differentiation of B cells both into post-switch memory cells as well as to plasma cells, establishing IL-21 as a global regulator of B cell differentiation and function.

Example 6

IL-21 Induces Human Plasma Cell Differentiation

The capacity of IL-21 to co-stimulate responses of purified human B cells was evaluated. Plasma cells were identified phenotypically as $CD19^{lo/+}IgD^-CD38^{hi}$ cells. Freshly obtained B cells or those retrieved from cultures were stained with anti-CD19, anti-IgD and anti-CD38. $CD19^+$ cells were assessed for expression of IgD and CD38. *Staphylococcus aureus* Cowan I (SAC) is a polyclonal B cell activator that induces rapid activation, differentiation and Ig production of B cells in the presence of IL-2. However, in the absence of IL-2, little plasma cell differentiation occurs. In contrast, costimulation of purified peripheral blood B cells with both SAC and IL-21 resulted in marked down-modulation of IgD and substantial differentiation of plasma cells that were phenotypically identified as CD19lo/+IgD–CD38hi cells.

Figure 8:
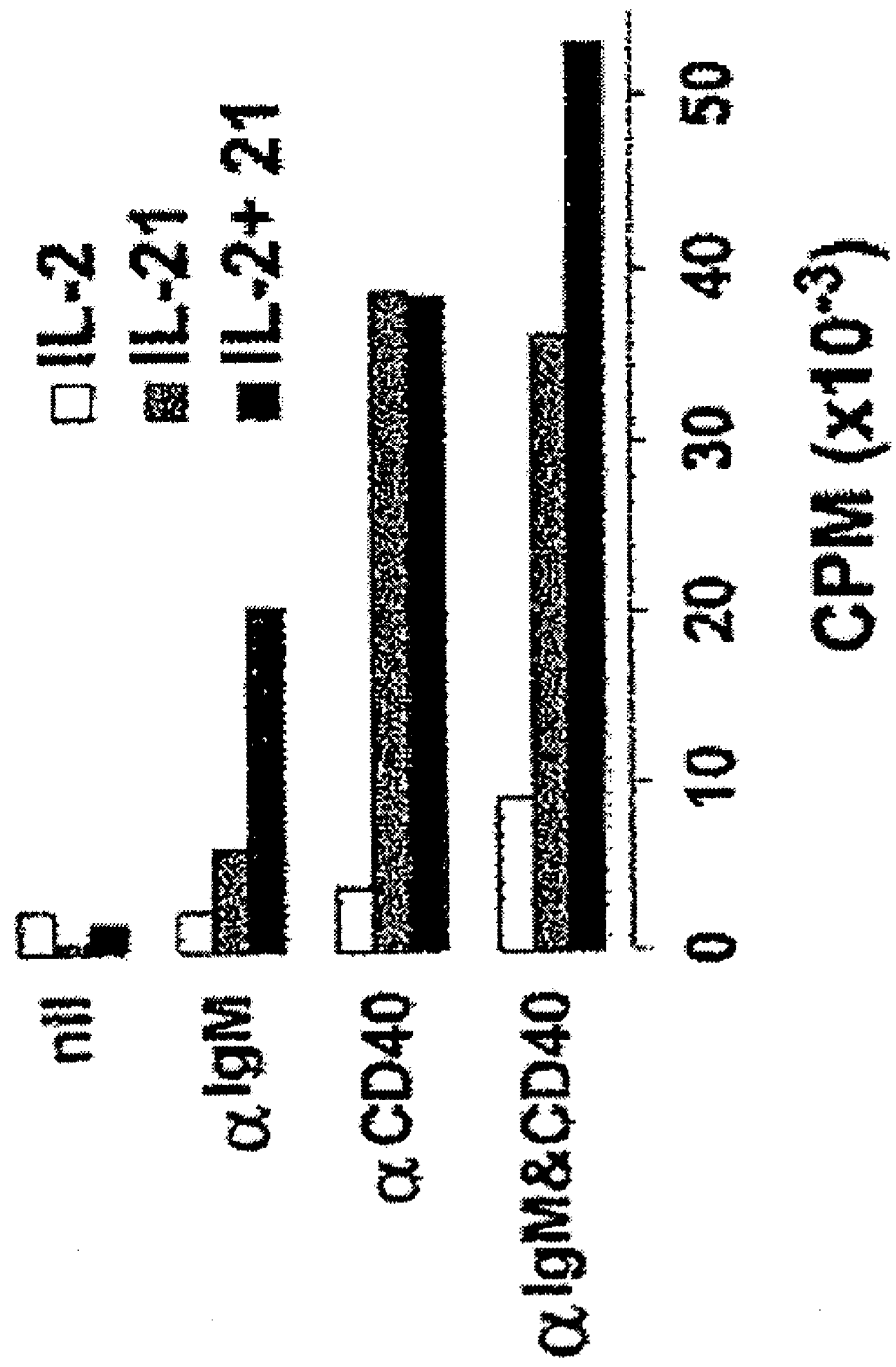
FIG. 8 is a bar graph illustrating the ability of IL-21 to induce plasma cell differentiation. Purified peripheral blood B cells stained with anti-IgD and anti-IgM contain few (1.3%) IgD⁻ CD38$^{hi}$ plasma cells. Purified peripheral blood B cells were stimulated with anti-IgM, anti-CD40, both stimuli, or neither in the presence or absence of IL-2 and/or IL-21 as indicated. After 3 days of culture, proliferation was determined by incubating the cells for 16 hrs with ³[H]-thymidine (FIG. 8). After 6 days of culture, the cells were stained and analyzed for surface expression of IgD and CD38 by CD19⁺ cells. Results from a representative experiment of six similar experiments are shown. Purified B cells were first labeled with CFSE before being cultured. Following 7 days of culture, CD19⁺ B cells were analyzed for CD38 expression and CFSE dilution.

We next examined whether IL-21 would co-stimulate B cells activated specifically through the B cell receptor and/or CD40. Only a small fraction (1.3%) of freshly isolated human peripheral B cells are IgD$^-$CD38$^{hi}$ plasma cells; the majority are IgD$^+$CD38$^{lo/Int}$ naïve B cells and a smaller percentage are IgD$^-$CD38$^{-/low}$ post-switched memory B cells. In the presence of anti-CD40 (which can stimulate both naïve and memory B cells), IL-21 induced maximal proliferation of B cells, whereas IL-2 had little effect (FIG. 8). In contrast, in the presence of anti-IgM (which stimulates IgD$^+$/IgM$^+$ B cells only), IL-21 induced only minimal proliferation. Notably, IL-2 enhanced the proliferation of B cells stimulated with anti-IgM and IL-21, whereas it had little effect on B cells stimulated with anti-CD40 and IL-21. When B cells were triggered through both CD40 and IgM, IL-21 induced a proliferative response that was comparable to that noted with anti-CD40 and IL-21. As with the anti-IgM and IL-21 costimulation, IL-2 also increased the magnitude of the response when cells were stimulated with the combination of IL-21, anti-IgM and anti-CD40.

Flow cytometric evaluation was carried out to assess the impact of IL-21 on human B cells. When negatively selected peripheral B cells were cultured with cytokines alone, modest changes in B cell phenotype were noted as determined by IgD and CD38 expression. However, IL-21 in the absence of any other stimulus increased the percentage of IgD$^-$CD38$^{hi}$ plasma cells modestly and this effect was augmented by IL-2. The ability of IL-21 to induce moderate plasma cell differentiation was also observed with anti-IgM-stimulated B cells, and again there was an increase in the presence of IL-2. In addition, IL-21 induced a striking loss in the numbers of B cells in anti-IgM stimulated cultures, that was largely reversed by the addition of IL-2. Moreover, IL-21 or the combination of IL-2 and IL-21 induced marked down-regulation of surface IgD by anti-IgM stimulated B cells and this was noted by day 4 of culture. IL-21 also induced IgD down-modulation by anti-CD40-stimulated B cells, as well as a dramatic increase in cellular expansion and plasma cell differentiation that was observed as early as day 4 of culture. T cell-dependent B cell responses involve engagement of both surface Ig as well as CD40 by CD154 expressed by activated T cells (Defrance et al., *J. Exp. Med.* 175:671-682, 1992).

The impact of IL-21 on B cells stimulated through both the B cell receptor (BCR) and CD40 was therefore examined. The combination of anti-IgM and anti-CD40 in the presence of IL-21 resulted in down-modulation of IgD by nearly all B cells. Moreover, the largest percentage of plasma cells was generated when both surface IgM and CD40 were engaged and the cells were co-stimulated with IL-21 in the presence or absence of IL-2. Evaluation of CFSE dilution revealed that IL-21 induced the differentiation of plasma cells from a dividing B cell precursor that had diluted CFSE with or without costimulation. Numeric calculation in repetitive experiments demonstrated the significant increase in both the percentage (FIG. 9A) and absolute cell number (FIG. 9B) of plasma cells in cultures co-stimulated with IL-21. The majority of the IL-21-driven plasma cells expressed conventional plasma cell antigens and were CD19$^{lo}$, CD20$^{lo}$, CD22$^{lo}$, CD21$^{lo}$, IgD$^-$, CD38$^{hi}$, BCMA$^+$, IL-6R$^+$ and CD27$^{hi}$.

Figure 9:
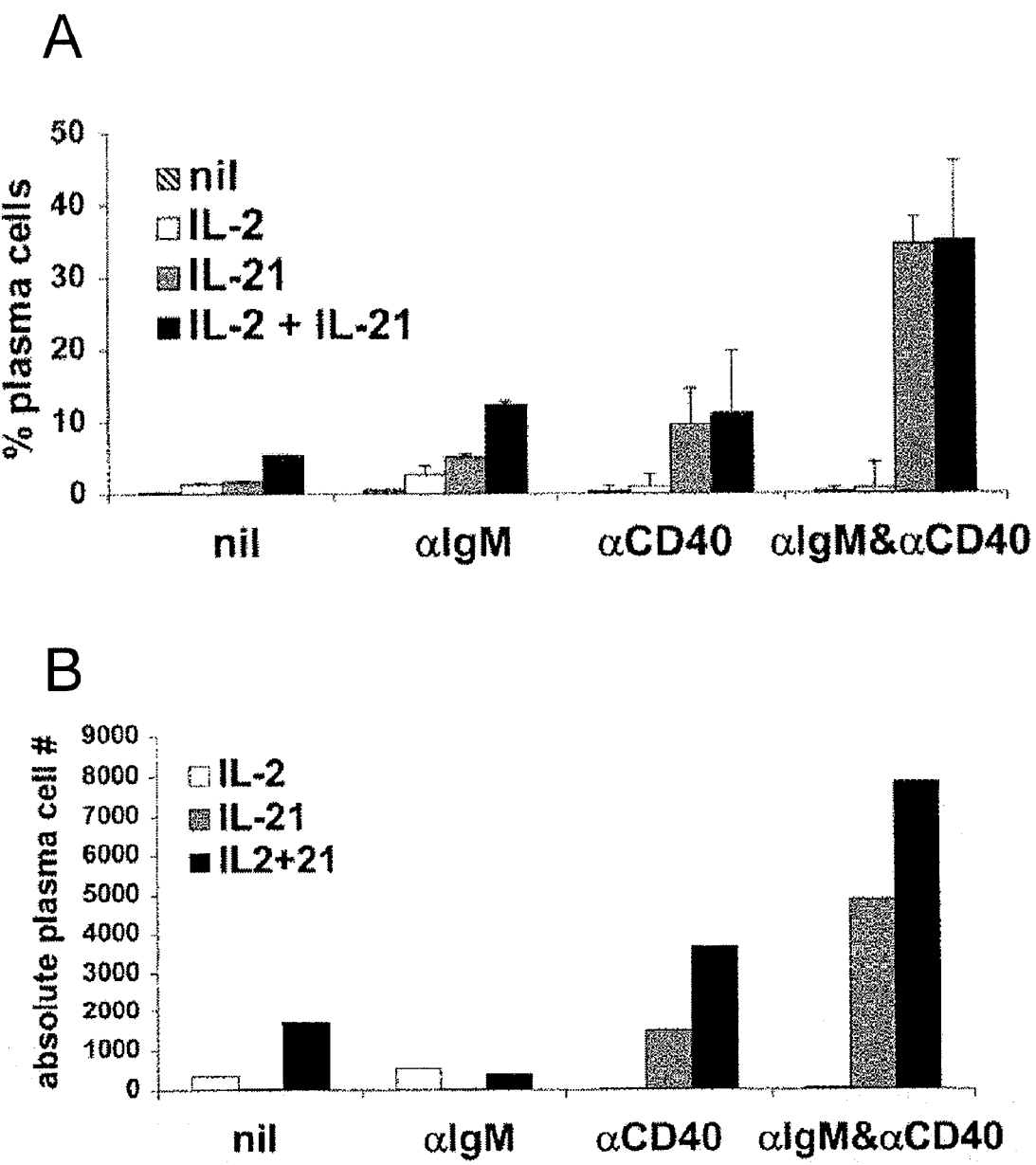
FIGS. 9A and B are bar graphs illustrating induction of plasma cells are induced following co-culture with IL-21. Purified peripheral blood B cells were cultured as described for FIG. 8, and the mean percentage (±SEM) of plasma cells from seven independent experiments is shown (FIG. 9A). The mean ³[H]-thymidine incorporation following 3 days of culture as CPM (±SEM) for these experiments was: IL-2, 4,300 (±1,200); anti-IgM+IL-2, 7,700 (±1,800); anti-CD40+IL-2, 7,600 (±1,100); and anti-IgM and anti-CD40+ IL-2, 19,700 (±10,400); IL-2+IL-21, 3,900 (±1,300); anti-IgM+IL-2+IL-21, 22,300 (±3,200); anti-CD40+IL-2+IL-21, 63,700 (±7,600); and anti-IgM and anti-CD40+IL-2+IL-21, 60,002 (±3,600). The absolute plasma cell number following 7 days in culture from one representative experiment is also shown (B). There were approximately 500 plasma cells/well in the initial population of cells.

CD27 expression indicates that human B cells have somatically mutated Ig genes, and therefore are considered to be memory B cells. These include both IgD$^+$CD27$^+$ B cells as well as IgD$^-$ CD27$^+$ post-switched B cells. To address whether IL-21 had the capability to drive plasma cell differentiation from both naïve and memory B cells, cord blood B cells were used as a natural source of naïve CD27$^-$IgD$^+$ B cells, and CD27$^+$ (IgD$^-$ and IgD$^+$) memory B cells were isolated from peripheral blood by cell sorting. As shown in FIGS. 9A and B, IL-21 co-stimulated considerable proliferation of both naïve cord blood and memory B cells. Although cord blood B cells co-stimulated with IL-21 proliferated less well than adult CD27$^+$ memory B cells (FIGS. 10A and B), the capacity of IL-21 to down-modulate IgD and induce differentiation of plasma cells was dramatic in both populations. Nearly all surviving IL-21-stimulated cord blood B cells activated with either anti-CD40 or anti-IgM and anti-CD40 had down-modulated IgD and/or differentiated into plasma cells. neither anti-CD40 nor anti-IgM and anti-CD40 stimulation of cord blood B cells alone led to the generation of any plasma cells in the absence of IL-21. However, IL-21 induced the down-modulation of IgD on stimulated cord blood B cells within 3 days of culture, and by day 6 many plasma cells were observed. In contrast, IL-21-induced differentiation of plasma cells from adult peripheral blood B cells could be observed within 4 days of culture.

IL-21 is a powerful co-stimulator of human plasma cell differentiation from human naïve as well as memory B cells. In contrast, a variety of other cytokines, including IL-2, IL-4, IL-6, and IL-10, have minimal ability to support the generation of plasma cells from comparably stimulated B cells. The combination of anti-IgM and anti-CD40, which most closely mimics B cell activation via antigen and T cell interaction, is the most effective signal in promoting the maximal differentiation of plasma cells driven by IL-21. Isolated BCR cross-linking, which mimics the "antigen-only" signal, primes B cells for IL-21-mediated death. These results indicate that IL-21 is involved in cell fate decisions by activated B cells and can function to eliminate B cells that have been activated by antigens or autoantigens in the absence of T cell signals.

Example 7

IL-21 Induces Ig Secretion from Human Naïve and Memory B Cells

Figure 11:
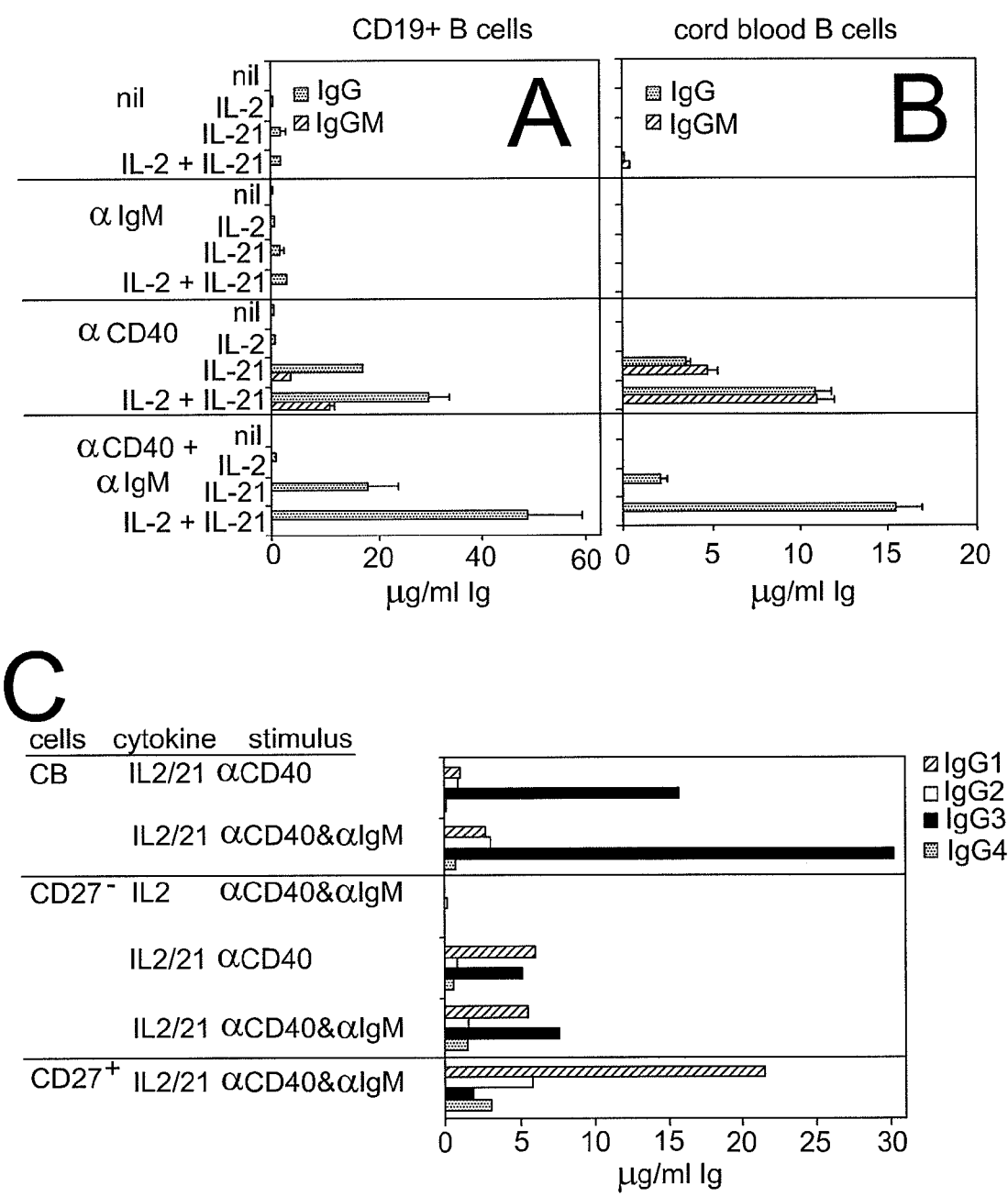
FIGS. 11A-C are bar graphs illustrating that IL-21 induces secretion of IgG and IgM. Purified B cells were cultured with either anti-IgM, anti-CD40, both stimuli, or neither in the presence or absence of IL-2, IL-21, or both IL-2 and IL-21. Cell supernatants were removed following (FIGS. 11A and B) 10-11 days of culture or (FIG. 11C) following 6 days (or 8 days, data not shown) for cord blood and 12 days for CD27⁻ & CD27⁺ B cells. Production of total IgG or IgM from purified total peripheral B cells (FIG. 11A) or cord blood B cells (FIG. 11B) and secretion of specific Ig isotypes from naïve cord blood B cells (CB), naïve (CD27⁻) adult B cells or memory (CD27⁺) B cells (FIG. 11C) were quantitated.

Analysis of culture supernatants confirmed that IL-21 induced the secretion of Ig. Unlike IL-2, or cultures with no added cytokines, IL-21 co-stimulated considerable production of both IgG and IgM from total adult peripheral B cells, as well as naïve cord blood B cells activated with anti-CD40 or anti-IgM and anti-CD40 (FIGS. 11A and B). The amount of Ig produced generally correlated with the frequency of plasma cells in the cultures. IgM and IgG could be assayed in the culture supernatants as early as day 4 of culture. IL-21 induced large amounts of IgG from both naïve CD27$^-$ adult and cord blood B cells (FIGS. 11B and C), consistent with its capability to function as a switch recombination factor for human B cells. All IgG isotypes were produced from adult CD27$^+$ memory B cells, as is expected from a population of post-switched memory B cells (FIG. 11C). Although all IgG isotypes were produced from naïve cord blood B cells stimulated with the combination of IL-2, IL-21, anti-CD40 or anti-IgM and anti-CD40, IgG3 predominated (FIG. 11C). In contrast, both IgG1 and IgG3 were the dominant IgG isotypes produced by IL-21 co-stimulated CD27$^-$ adult naïve B cells (FIG. 11C). In addition, stimulation with of IL-21 and anti-CD40 or IL-21, anti-CD40 and anti-IgM of peripheral blood B cells had no effect on IgE production, but did costimulate IgA production without or with IL-2 (1-2 µg/ml vs. 4-6 µg/ml of IgA respectively).

Example 8

IL-21 Induces Expression of Blimp-1, AID and Bcl-6 in Human B Cells

Figure 12:
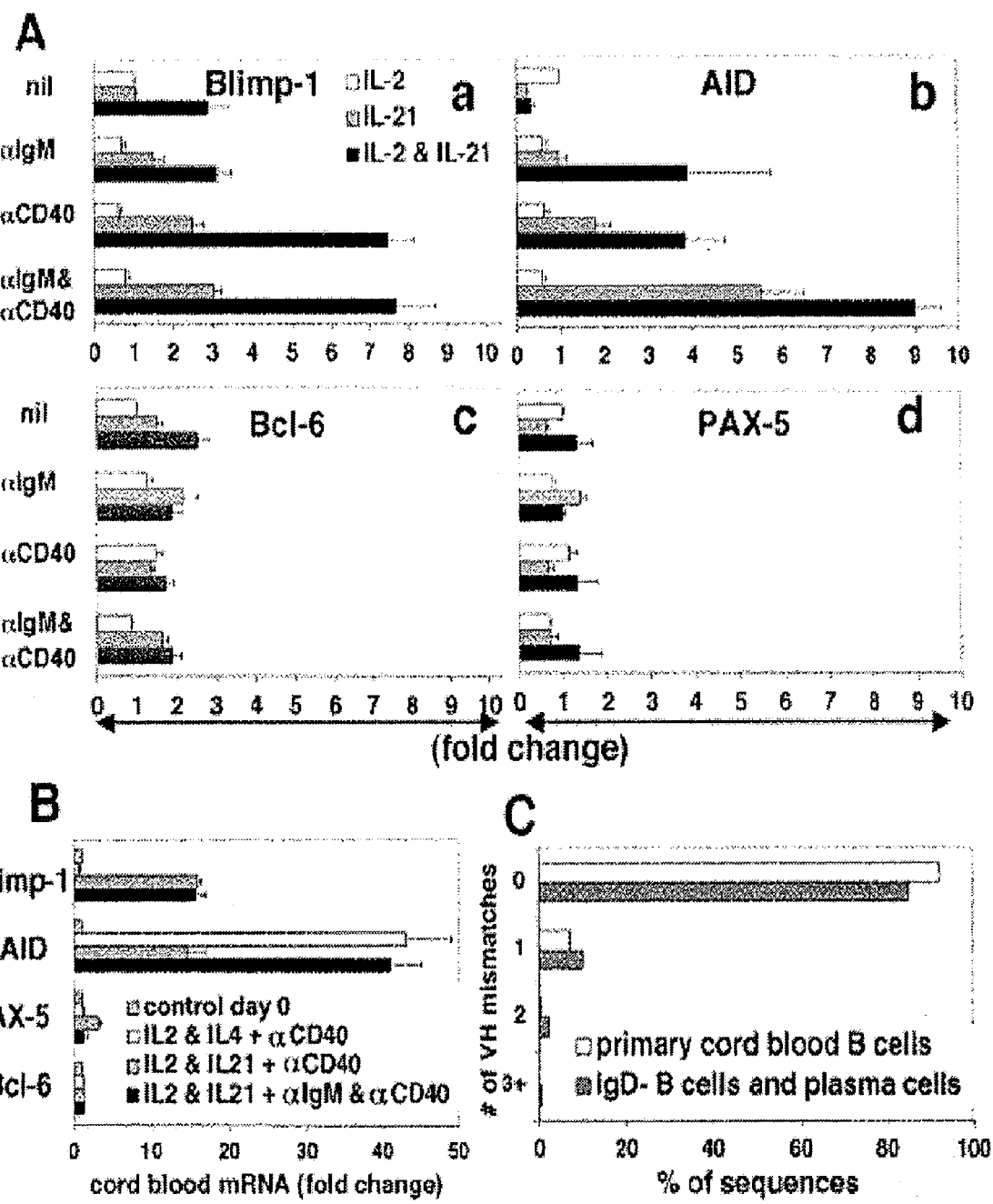
FIGS. 12A-C are bar graphs showing that IL-21 induces both BLIMP and AID expression, but not somatic hypermutation. Purified peripheral B cells (FIG. 12A) or cord blood B cells (FIGS. 12B and C) were cultured with the stimuli and cytokines indicated. After 3 days of culture, cells were harvested, verified for cell surface phenotype, RNA isolated and quantitative RT-PCR was carried out to identify Blimp-1, AID, Bcl-6 and PAX-5 mRNA. All data were normalized to β-2M mRNA and data shown represent fold change compared to samples that were incubated with IL-2 with no other stimuli (FIG. 12A), or to primary cord blood B cells (FIG. 12A). Data are representative of results from six similar experiments for peripheral blood B cells, and two for cord blood B cells. Mean fold change (±SEM) of triplicate mRNA samples from one representative experiment is shown. Negatively-selected cord blood B cells were examined for mutations of rearranged heavy chain genes before and after 7-12 days of in vitro stimulation with IL-2, IL-21 and anti-CD40 with or without anti-IgM (FIG. 12C). After stimulation, IgD⁻ CD38$^{hi}$ plasma cells (n=189) or post-switched IgD⁻ CD38$^{-/low}$ B cells (n=79) were isolated by cell sorting and the Ig V$_H$ genes were amplified from genomic DNA by single cell PCR, sequenced, and the frequency of Ig V$_H$ mismatches was compared to that found in cord blood B cells before culture (n=141). Combined results from four experiments are shown.

A variety of transcription factors are known to regulate specific stages of B cell maturation. Therefore, it was determined whether IL-21 costimulation upregulated expression of Blimp-1, which is essential for plasma cell differentiation (Turner et al., *Cell* 77:297-306, 1994), AID, which is involved in CSR (Durandy, *Eur. J. Immunol.* 33:2069-2073, 2003), Bcl-6, which is involved in germinal center reactions (Ye et al., *Nat. Genet.* 16:161-170, 1997), or PAX-5, which is required for the generation of B cells (Rolink et al., *Immunol. Rev.* 187:87-95, 2002). IL-21 induced expression of both Blimp-1 (FIG. 12A panel a) and AID (FIG. 12A panel b) mRNA. Blimp-1 was induced by IL-21 co-stimulated B cells activated with anti-CD40 or anti-IgM and anti-CD40, and less so with anti-IgM only (FIG. 12A panel a). However, in the presence of IL-2, IL-21 also induced Blimp-1 expression without additional costimulation. Furthermore, IL-2 enhanced the IL-21-mediated Blimp-1 expression in B cells activated by anti-CD40 or anti-CD40 and anti-IgM (FIG. 12A panel a). AID mRNA was induced by IL-21 only when B cells were activated with anti-CD40 or both anti-IgM and anti-CD40, and was enhanced by the presence of IL-2, especially when B cells were stimulated with anti-IgM (FIG. 12A panel b). Bcl-6 mRNA was induced to a lesser degree by IL-21 (FIG. 12A panel c), whereas IL-21 had little effect on PAX-5 mRNA (FIG. 12A panel d). To determine whether IL-21 had the ability to induce these transcription factors in naïve B cells, experiments using cord blood B cells were undertaken. IL-21 co-stimulated a significant increase in Blimp-1 mRNA in naïve cord blood B cells, whereas the combination of IL-2 and IL-4 exhibited no such activity (FIG. 12B). IL-21 also co-stimulated AID mRNA expression, but no more effectively then the combination of IL-2 and IL-4 (FIG. 12B). In contrast, IL-21 had little effect on Bcl-6 or PAX-5 mRNA levels.

IL-21 costimulation increased AID mRNA levels, differentiation of IgD$^+$ and IgD$^-$ B cells, class switch recombination, generation of plasma cells, and Ig production, but it could not induce somatic hypermutation. No increase in mutation of V$_H$ genes was detected in IgD$^-$ CD38$^{+/-}$ B cells or IgD$^-$CD38$^{hi}$ plasma cells isolated from cultures of cord blood B cells stimulated with anti-CD40 with or without anti-IgM in the presence of IL-2 and IL-21 (FIG. 12C).

Blimp-1 is a transcriptional repressor that is necessary/sufficient for plasma cell differentiation in the mouse, and in human B cell lines (Turner et al., *Cell* 77:297-306; Shapiro-Shelef et al., *Immunity* 19:607-620, 2003; Shaffer et al., *Immunity* 17:51-62, 2002). Consistent with this, IL-21-driven plasma cell differentiation from both naïve cord blood B cells as well as CD27+ memory B cells was preceded by the induction of Blimp-1 up-regulation. Other cytokines examined in this study did not induce Blimp-1 expression, although IL-2 enhanced the effects of IL-21. As indicated in Example 5, IL-21 induced Blimp-1 expression in murine splenic B cells. The capacity of IL-21 to upregulate Blimp-1 explains its ability to drive plasma cell differentiation. In addition, IL-21 costimulation induced AID expression which is normally down-modulated by Blimp-1 (Shaffer et al., *Immunity* 17:51-62, 2002). Although, AID is a B cell-specific factor that is sufficient for both CSR and SHM (Honjo et al., *Immunity* 20:659-668, 2004), IL-21 costimulation induced CSR, but not SHM. Similar findings have been reported with CD27− B cells stimulated with the combination of SAC, IL-2, IL-10, and cross-linked anti-CD40 (Nagumo et al., *Blood* 99:567-575, 2002). IL-4 and CD40 stimulation induced AID in cord blood B cells, but neither CSR nor plasma cell differentiation. Previously, AID has been shown to be induced by IL-4, anti-CD40 or the combination of both IL-4 and anti-CD40 in adult B cells (Pene et al., *J. Immunol.* 172:5154-5157, 2004; Zhou et al., *J. Immunol.* 170:1887-1893; Dedeoglu et al., *Intl. Immunol.* 16:395-404, 2004). Although AID was induced to comparable levels by IL-4 and IL-21, although only the latter induced CSR. In this regard, engagement of CD40 induced both AID and SHM in human Ramos B cell lines (Zan et al., *Immunity* 18:727-738, 2003; Faili et al., *Nat. Immunol.* 3:815-821, 2002). These results indicate that up-regulation of AID has different effects on B cells at different stages of differentiation. Moreover, our data indicate that the induction of AID mRNA is not sufficient to induce CSR or SHM in all circumstances. Without being bound by theory, it is likely that IL-21 can induce CSR, the activity of AID that is governed by the C-terminal portion of the molecule and involves the capacity to bind DNA-PKcs Wu et al., *J. Immunol.* 174:934-941, 2005), whereas it is not able to induce SHM that is regulated by the N-terminal of the protein by unknown molecules (Shinkura et al., *Nat. Immunol.* 7:707-712, 2004).

Example 9

Effect of Cytokines on Plasma Cell Generation Promoted by IL-21

The effects of IL-21 can be modulated by other cytokines. IL-4 partially inhibited the down-modulation of surface IgD induced by IL-21 in cells stimulated with *Staphylococcus aureus* Cowan I (SAC), which is a polyclonal B cell activator that induces rapid activation, differentiation and Ig production of purified B cells in the presence of IL-2 (Teranishi et al., *J. Immunol.* 133:3062-3067, 1984). Moreover, IL-4 also inhibited IgD down-modulation induced by IL-21 and anti-IgM or the combination of anti-IgM and anti-CD40, but not by anti-CD40 alone. Importantly, IL-21-induced generation of plasma cells was also inhibited by IL-4 in cultures co-stimulated by SAC, or in cultures containing the combination of IL-21, anti-IgM and anti-CD40—but not in cultures of IL-21 and anti-CD40. This was reflected in the quantity of secreted Ig (FIG. 13A), as well as the levels of AID or Blimp-1 mRNA (FIG. 13B). The effect on AID mRNA was only observed in cultures stimulated by anti-IgM and anti-CD40. The addition of IL-2 did not rescue IgG production in IL-4 suppressed cultures (FIG. 13A), but did allow for the differentiation of IgM-producing plasma cells.

The next experiments compared the impact of IL-21 with IL-10 which is known to support plasma cell differentiation (Briere et al., *J. Exp. Med.* 179:757-762, 1994; Rousset et al., *Proc. Natl. Acad. of Sci. USA* 89:1890-1893, 1992). IL-10 induced minimal B cell responses compared to IL-21 when added in the same culture conditions. IL-10 co-stimulated neither Ig-production nor differentiation (FIG. 14A) of naïve cord blood B cells under any condition, but did induce low levels of Ig and small numbers of cells to differentiate into plasma cells upon culture of purified CD27$^+$ memory B with anti-CD40 or anti-IgM and anti-CD40. Moreover, IL-10 had no effect on B cell responses supported by IL-21 in contrast to the effects of IL-4.

Figure 15:
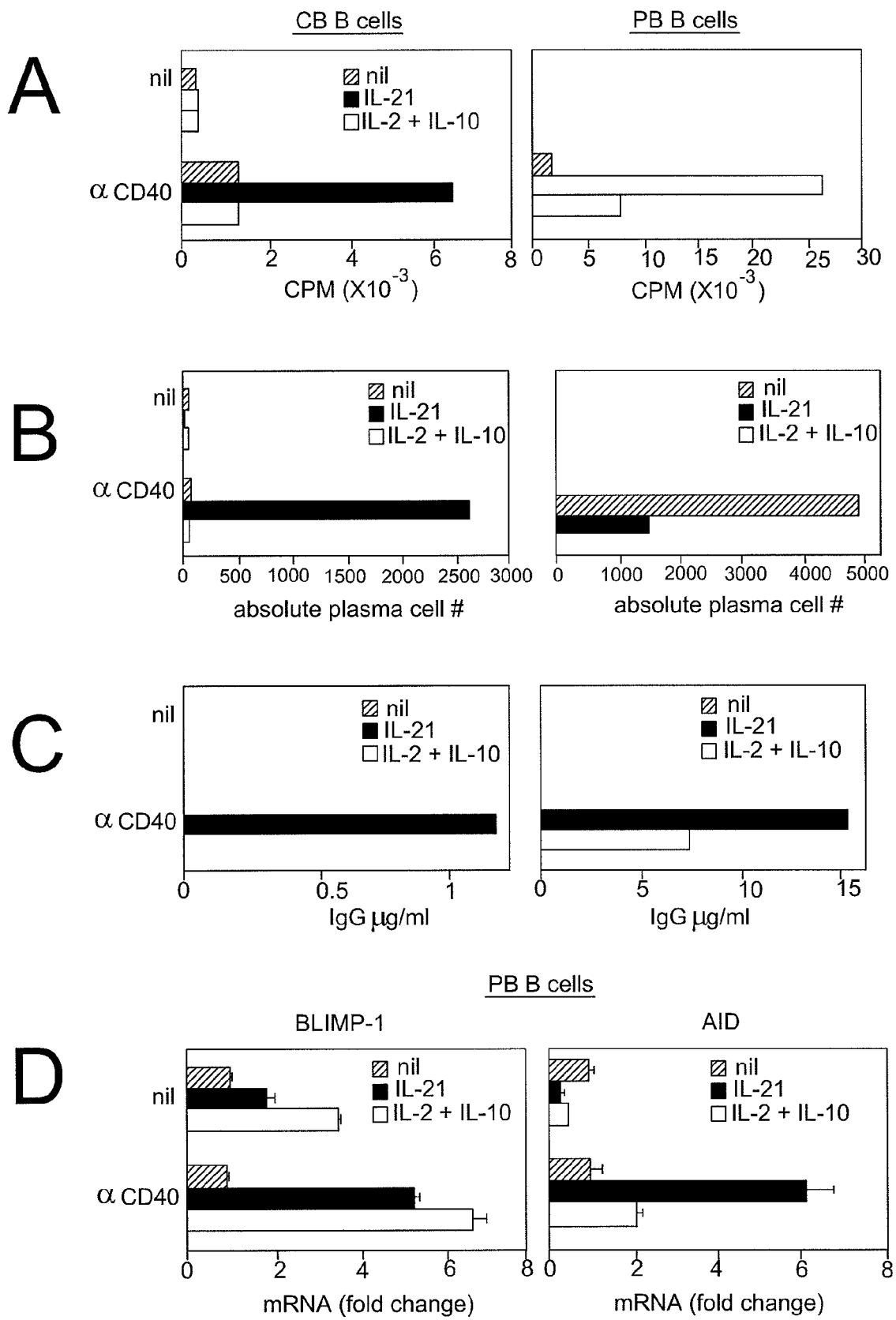
FIGS. 15A-D are bar graphs illustrating proliferative responses and immunoglobulin secretion induced by IL-21 or IL-2 plus IL-10. IL-21 induces greater proliferation, plasma cell differentiation, and IgG production from anti-CD40-stimulated peripheral blood and cord blood B cells than does IL-2 and IL-10. (A-C) Purified naïve cord blood B cells (CB) or (A-D) peripheral blood B cells (PB) were cultured with the stimuli and cytokines indicated for (A) 3 days, (B) 7 days, (C) 9 days for CB B cells and 10 days for PB B cells and (D) 3 days. At the end of the incubation period (A) $^3$[H]-thymidine incorporation, (B) absolute plasma cell number, and (C) IgG secretion were determined. In (D) relative fold change of mRNA was determined for BLIMP-1 and AID. All samples were first normalized to β-2M mRNA and then to mRNA of samples that were not stimulated and did not contain cytokine (nil, nil). Data are shown as mean fold change (±SEM). Data shown are representative results.

The effect of IL-21 was then compared to that of the combination of IL-2 and IL-10, which has been shown to support plasma cell differentiation under some circumstances. As shown in FIG. 15, stimulation of purified peripheral blood B cells with anti-CD40 and the combination of IL-2 and IL-10 induced proliferation (FIG. 15A), as well as the differentiation of plasma cells (FIG. 15B) and IgG secretion (FIG. 15C), although the responses were not as robust as those induced by anti-CD40 and IL-21. In contrast, stimulation of naïve cord blood B cells with anti-CD40 and the combination of IL-2 and IL-10 failed to stimulate any of these responses, although IL-21 induced proliferation, plasma cell generation and IgG secretion from anti-CD40-stimulated cord blood B cells (FIG. 15A-C). Notably, however, the combination of IL-2 and IL-10 induced upregulation of both BLIMP-1 and AID mRNA, although AID mRNA was induced substantially more effectively by IL-21 (FIG. 15D).

IL-2 has previously been shown to drive plasma cell differentiation when B cells are activated with SAC (Teranishi et al., *J. Immunol.* 133:3062-3067, 1984), as well as co-stimulate plasma cell differentiation in the presence of anti-CD40 and IL-10 (Arpin et al., *J. Exp. Med.* 186:931-940, 1997; Splawski et al., *Eur. J. Immunol.* 28:4248-4256, 1998) or IL-6 (Jego et al., *Blood* 97:1817-1822, 2001; Vernino et al., *J. Immunol.* 148:404-410, 1992). IL-4, on the other hand, has been shown to both promote and inhibit B cell responsiveness to various stimuli (Arpin et al., *J. Exp. Med.* 186:931-940, 1997; Splawski et al., *J. Immunol.* 150:1276-1285, 1993; Jelinek et al., *J. Immunol.* 141:164-173, 1988; Fujieda et al., *J. Immunol.* 155:2318-2328, 1995; Splawski et al., *J. Immunol.* 142:1569-1575, 1989; Jabara et al., *J. Exp. Med.* 172:1861-1864, 1990). IL-2 enhanced the effect of IL-21 on plasma cell differentiation induced by the combination of anti-IgM and anti-CD40, whereas IL-4 inhibited it. Moreover, IL-4 blocked IL-21-induced death of naïve B cells stimulated with anti-IgM. These results indicate an antagonistic effect of IL-4 on the actions of IL-21 in B cells stimulated by anti-IgM or the combination of anti-IgM and anti-CD40. Antagonism between IL-4 and IL-21 was not consistently observed when cells were stimulated with anti-CD40 alone, indicating that the nature of the stimulus influences the ability of B cells to respond to the combination of IL-4 and IL-21. Consistent with this, IL-4 has been shown to enhance Ig production by IL-21 and anti-CD40 activated CD27+ human splenic memory B cells (Pene et al., *J. Immunol.* 172:5154-5157, 2004). This finding makes it unlikely that receptor competition can explain these results, owing to the fact that both IL-21 and IL-4 utilize the $\equiv_c$ for signaling (Zhang et al., *Biochem. Biophys. Res. Comms.* 300:291-296, 2003). In addition, IL-2, which also signals through a receptor containing $\gamma_c$, reversed the IL-4 mediated-inhibition of IgM-producing plasma cell generation, making the idea of receptor competition more remote. Furthermore, IL-2 synergized with IL-21 in fostering growth of anti-IgM and anti-CD40 stimulated B cells. Thus, stimulus dependent inhibition of IL-21 responses by IL-4 relates to the down stream signals generated by engagement of the IL-4 receptor. In this regard, IL-4 is known to co-stimulate IgE synthesis by human B cells (Jabara et al., *J. Exp. Med.* 172:1861-1864, 1990), and also induce the expression of CD23 on mature B cells (Nelms et al., *Ann. Rev. Immunol.* 17:701-738, 1999). However, IL-4 also has been reported to repress human B cells responses (Jelinek et al., *J. Immunol.* 141:164-173, 1988; Splawski et al., *J. Immunol.* 142:1569-1575, 1989), and inhibit Blimp-1 induction as well as plasma cell differentiation in mice (Knodel et al., *Eur. J. Immunol.* 31:1972-1980, 2001). With the appropriate costimulation, IL-4 repressed Blimp-1 expression, and inhibited plasma cell differentiation, whereas IL-21 induced both Blimp-1 and plasma cell differentiation. In the appropriate signaling context, the actions of the two cytokines appear to be mutually inhibitory of one another. In this regard, IL-21 has been reported to inhibit proliferation of both murine and human B cells stimulated with anti-IgM and IL-4 (Parrish-Novak et al., *Nature* 408:57-63, 2000; Ozaki et al., *Science* 298:1630-1634, 2002; Ozaki et al., *J. Immunol.* 173: 5361-5371, 2004) and to inhibit IL-4 induced IgE transcription (Suto et al., *Blood* 100:4565-4573, 2002).

As discussed above, IL-4 repressed IL-21-driven plasma cell differentiation following either SAC or anti-IgM and anti-CD40 stimulation. IL-4R ligation induces primarily STAT6, which is essential for IL-4 signaling, including IL-4-induced up-regulation of AID in both mice and humans (Zhou et al., *J. Immunol.* 170:1887-1893, 2003; Dedeoglu et al., *Intl. Immunol.* 16:395-404, 2004), whereas IL-21R engagement activates primarily STAT1 and 3 and more weakly 5 (Ozaki et al., *Proc. Natl. Acad. Sci.* 97:11439-11444, 2000; Habib et al., *Biochem.* 41:8725-8731, 2002; Habib et al., *J Allergy & Clin. Immunol.* 112:1033-1045, 2003). The data suggest that IL-21 and IL-4 inhibit one another's actions after receptor engagement. Biologically, T cell-dependent B cell responses may be regulated by T cells that either produce IL-21, IL-4 or other cytokines at different times during an immune response or different subsets of T cells that express different cytokine profiles. In support of this, IL-21 has been described to be produced by a restricted subset of follicular T helper cells that express CXCR5 in humans (Chtanova et al., *J. Immunol.* 173:68-78, 2004).

Example 10

Figure 16:
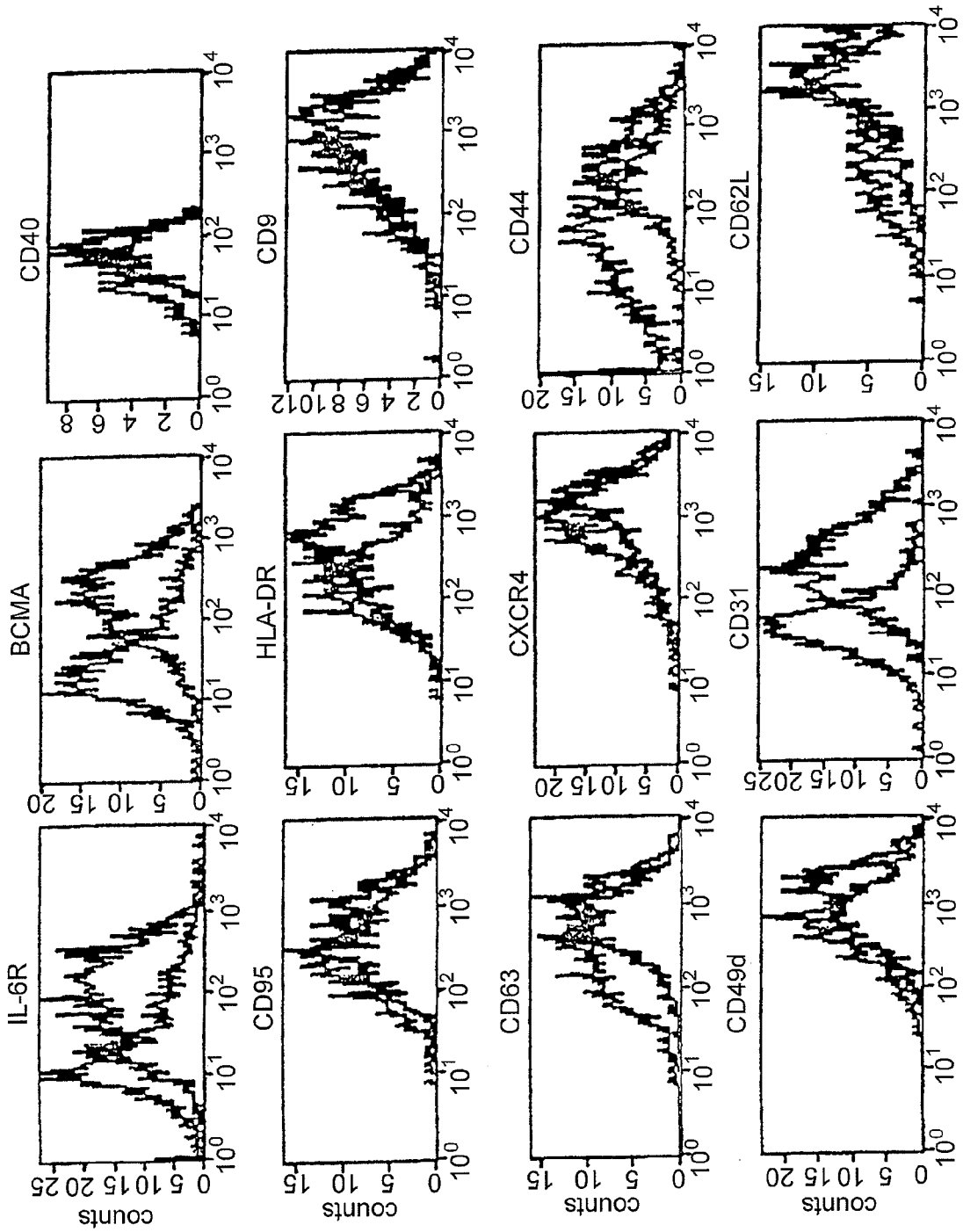
FIG. 16 is a set of histograms illustrating the cell surface phenotype of IL-21-induced plasma cells. Purified peripheral blood B cells were isolated and cultured with IL-21, anti-IgM and anti-CD40. Following 7 or 8 days of culture, CD19+ cells were subdivided into IgD-CD38$^{lo}$ cells and IgD-CD38$^{hi}$ plasma cells and further analyzed for expression of the markers indicated. The data reflect representative results.

IL-21-Induces Differentiation of Non-Dividing, Terminally Differentiated Plasma Cells The status of IL-21-induced plasma cells was examined by cell surface phenotype and cell cycle analysis. In addition to being $CD19^{lo/+}IgD-CD38^{hi}$, the majority of IL-21, anti-CD40 and anti-IgM-induced plasma cells were also found to express other typical plasma cells markers such as IL-6R and BCMA (FIG. 16). Furthermore, when compared to IgD-$CD38^{lo}$ cells, these plasma cells were $CD40^+$, $CD95^{lo}$, HLA-$DR^{lo}$, $CD9^{hi}$, $CD63^{hi}$, $CXCR4^{lo/+}$, $CD44^{hi}$, $CD49d^{lo}$, $CD31^{hi}$ and $CD62L^{hi}$ (FIG. 16). The majority of the IL-21-driven plasma cells were also $CD19^{lo}$, $CD20^{lo}$, $CD22^{lo}$, $CD21^{lo}$ and $CD27^{hi}$.

Figure 17:
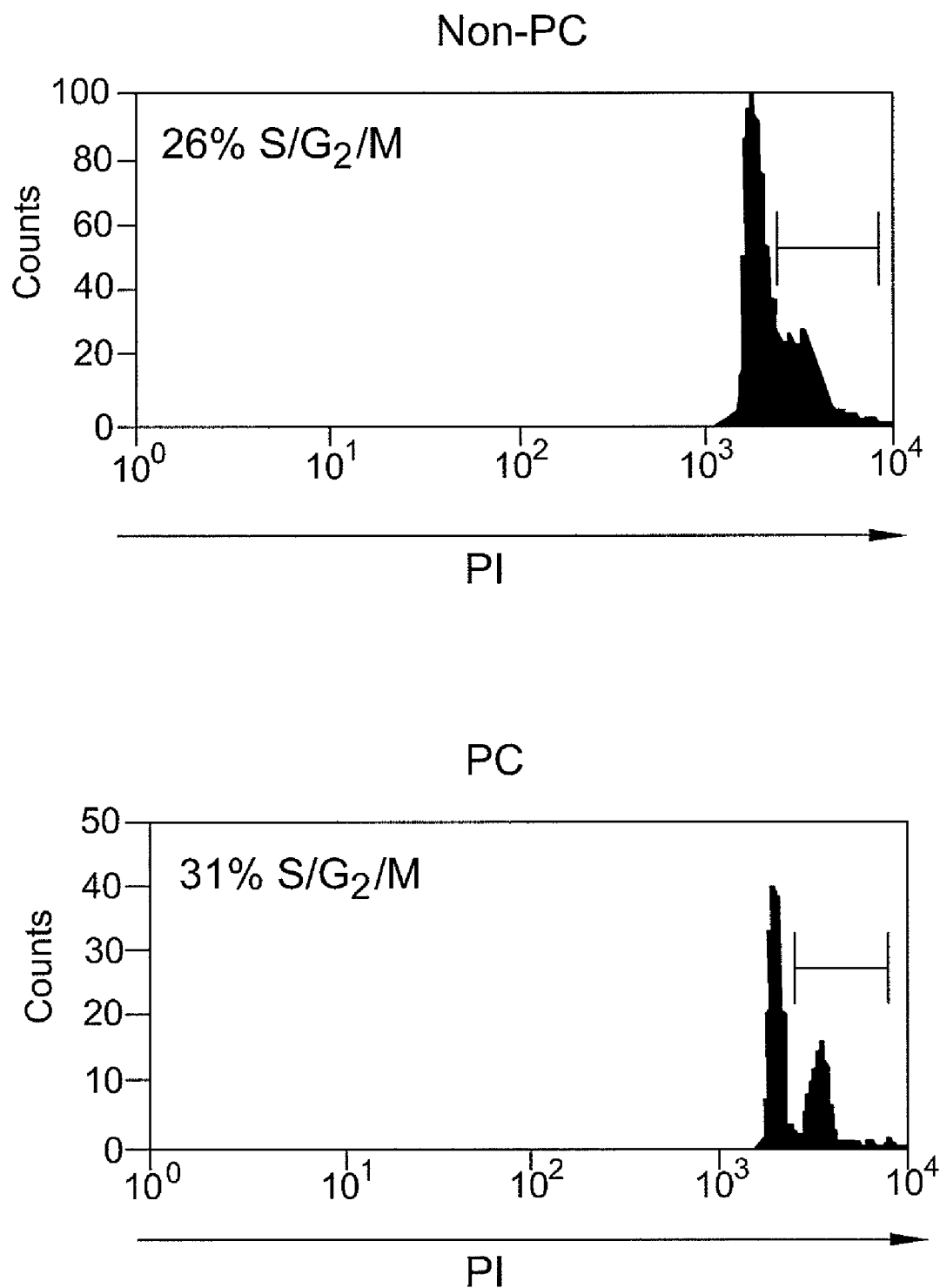
FIG. 17 is a histogram showing that the majority of IL-21-induced plasma cells are not in cell cycle. Purified peripheral blood B cells were isolated and cultured with IL-21, anti-IgM and anti-CD40. Following 7 days of culture, cells were stained with the combination of either anti-IgD, anti-CD27, anti-CD19 and anti-CD38 or anti-CD27, anti-CD38 and PI. For the latter, cells were subdivided into either CD27− & +, CD38$^{lo}$ non-plasma cells (non-PC) or CD27$^{hi}$, CD38$^{hi}$ plasma cells (PC) and cell cycle was determined. Cell surface phenotype of cells before culture is shown.

To evaluate whether IL-21-induced plasma cells were terminally differentiated nondividing cells, cell cycle analysis was also carried out. To assess cell cycle position, B cells were stimulated with IL-21, anti-IgM and anti-CD40 and after 7 days of culture the resultant plasma cells were identified either as $IgD-CD38^{hi}$ or $CD27^{hi}CD38^{hi}$ cells that were differentiated from $CD27^{lo}CD38^{lo}$ non-plasma cells. Both populations were analyzed for cell cycle progression by PI staining (FIG. 17). As shown in FIG. 17, the majority of IL-21-induced plasma cells as well as non-plasma cells were not cycling as evidenced by the finding that they were not in the S, G2 or M phase of the cell cycle, although 46% of the non-plasma cells were found to be in S/G2/M on day 3, before plasma cell differentiation.

Whether IL-21-induced plasma cells had differentiated to non-dividing Ig secreting cells, Ig production was examined in the presence of the inhibitor of proliferation, hydroxyurea. The addition of hyrdoxyurea at the initiation of culture IL-21 drives human plasma cell differentiation resulted in a complete block of IL-21-induced proliferation and plasma cell differentiation (FIG. 18A). However, when hydroxyurea was added to the cultures at day 8 after differentiation of plasma cells, persistence of these cells was noted over the next three days of culture. The amount of Ig doubled during the last 3 days of culture which was not blocked by hydroxyurea, indicating that the ongoing production of Ig by plasma cells was not dependent on ongoing proliferation. These data demonstrate that the production of Ig by IL-21-induced plasma cells reflects secretory activity of terminally differentiated, nondividing cells (FIG. 18B).

It will be apparent that the precise details of the methods or compositions described can be varied or modified without departing from the spirit of the described invention. We claim all such modifications and variations that fall within the scope and spirit of the claims below.

We claim:

1. A method for promoting differentiation of at least one mature naïve B cell and/or B cell progenitor into one or more memory B cells and/or plasma cells, the method comprising:
   (a) contacting a population of cells comprising mature naïve B cells and/or B cell progenitors with an IL-21 polypeptide comprising the amino acid sequence of SEQ ID NO: 1, wherein the population of cells is contacted with an antigen, thereby promoting differentiation of at least one mature naïve B cell and/or B cell progenitor in the population of cells into one or more memory B cells and/or plasma cells; and
   (b) isolating memory B cells and/or plasma cells from the population of cells.

2. The method of claim 1, wherein the memory B cells and/or plasma cells are isolated from the population of cell by flow cytometry, magnetic separation, or affinity chromatography.

3. The method of claim 2, wherein the flow cytometry is fluorescence activated cell sorting.

4. The method of claim 2, wherein the magnetic separation includes the use of magnetic beads.

5. A method for promoting differentiation of at least one mature B cell and/or B cell progenitor into one or more memory B cells and/or plasma cells, the method comprising:
   (a) contacting a population of cells comprising mature B cells and/or B cell progenitors with an IL-21 polypeptide comprising the amino acid sequence of SEQ ID NO: 1, wherein the population of cells is contacted with an antigen, thereby promoting differentiation of at least one mature B cell and/or B cell progenitor in the population of cells into one or more memory B cells and/or plasma cells; and
   (b) isolating memory B cells and/or plasma cells from the population of cells.

6. The method of claim 5, wherein the memory B cells and/or plasma cells are isolated from the population of cell by flow cytometry, magnetic separation, or affinity chromatography.

7. The method of claim 6, wherein the flow cytometry is fluorescence activated cell sorting.

8. The method of claim 6, wherein the magnetic separation includes the use of magnetic beads.

* * * * *